United States Patent
Alabed et al.

(10) Patent No.: US 11,946,057 B2
(45) Date of Patent: Apr. 2, 2024

(54) PRE-CONDITIONING TREATMENTS TO IMPROVE PLANT TRANSFORMATION

(71) Applicant: Benson Hill, Inc., St. Louis, MO (US)

(72) Inventors: Diaa Alabed, Creve Coeur, MO (US); Lorena Beatriz Moeller, Wildwood, MO (US)

(73) Assignee: Benson Hill, Inc., St. Louis, MO (US)

( * ) Notice: Subject to any disclaimer, the term of this patent is extended or adjusted under 35 U.S.C. 154(b) by 0 days.

(21) Appl. No.: 17/416,223

(22) PCT Filed: Dec. 19, 2019

(86) PCT No.: PCT/IB2019/061126
§ 371 (c)(1),
(2) Date: Jun. 18, 2021

(87) PCT Pub. No.: WO2020/128968
PCT Pub. Date: Jun. 25, 2020

(65) Prior Publication Data
US 2022/0073936 A1    Mar. 10, 2022

Related U.S. Application Data

(60) Provisional application No. 62/807,056, filed on Feb. 18, 2019, provisional application No. 62/782,602, filed on Dec. 20, 2018.

(51) Int. Cl.
*C12N 15/82* (2006.01)
(52) U.S. Cl.
CPC ..... *C12N 15/8207* (2013.01); *C12N 15/8213* (2013.01)
(58) Field of Classification Search
CPC .................................................. C12N 15/8202
See application file for complete search history.

(56) References Cited

FOREIGN PATENT DOCUMENTS

| WO | WO2013/090734 A1 * | 6/2013 | |
| WO | WO 2013/090734 A1 | 6/2013 | |
| WO | WO-2013090734 A1 * | 6/2013 | ......... C12N 15/8205 |

OTHER PUBLICATIONS

Mano H, Fujii T, Sumikawa N, Hiwatashi Y, Hasebe M (2014) Development of an Agrobacterium-Mediated Stable Transformation Method for the Sensitive Plant Mimosa pudica. PLoS One 9(2): e88611. doi:10.1371/journal.pone.0088611.*
Naegeli et al. (2017). Scientific opinion on an application by Monsanto (EFSA-GMO-NL-2013-114) for the placing on the market of a herbicide-tolerant genetically modified cotton MON 88701 for food and feeds uses, impart and processing under regulation (EC) No. 1829/2003. EFSA Journal, 15(3);4746.*
Sanford (Sanford, J. C, 1990. Biolistic plant transformation.—Physiol. Plant. 79: 206-209).*
Klimel-Chodacka (Klimel-Chodacka, M. et al. (2018). Efficient CRISPR/Cas9-based genome editing in carrot cells. Plant Cell Report. 37: 575-586.).*
Asande et al. (2020). Plant Methods,16:141.*
Lacroix B and Citovsky V. Annu. Rev. Phytopahtol. Aug. 25, 2019; 57:231-251.*
Mano H, Fujii T, Sumikawa N, Hiwatashi Y, Hasebe M (2014). PLoS One 9(2): e88611.*
Naegeli et al. 2017. EFSA Journal 2017;15(3):4746.*
Klimel-Chodacka, M. et al. (2018). Efficient CRISPR/Cas9-based genome editing in carrot cells. Plant Cell Report. 37: 575-586.*
Curtis, I., et anan., "Transgenic rash (*Raphanus sativus* L. *longipinnatur* Bailey) by floral-dip method—plant development and surfactant are important in optimizing transformation efficiency," *Transgenic Research*, 2001, vol. 10(4), pp. 363-371.
Mano, H., et al., "Development of an Agrobacterium-Mediated Stable Transformation Method for the Sensitive Plant *Mimosa prudica*," *PLOS One*, 2014, vol. 9(2), p. 388611 (pp. 1-11).

* cited by examiner

*Primary Examiner* — David H Kruse
(74) *Attorney, Agent, or Firm* — Womble Bond Dickinson (US) LLP

(57) ABSTRACT

Provided herein are methods for increasing plant cell transformation efficiency. These methods include exposing the plant cells to a liquid medium containing a surfactant. Following exposure to the surfactant-containing medium, the cells can become more amenable to transformation and may be genetically transformed using methods known in the art. Exposure of the cells to the surfactant-containing medium prior to transformation can increase plant transformation efficiency when compared to transformation efficiency of cells not exposed to the surfactant-containing medium.

19 Claims, No Drawings
Specification includes a Sequence Listing.

SEQUENCE LISTING

```
<160> NUMBER OF SEQ ID NOS: 20

<210> SEQ ID NO 1
<211> LENGTH: 720
<212> TYPE: DNA
<213> ORGANISM: Aequorea victoria
<220> FEATURE:
<221> NAME/KEY: misc_feature
<222> LOCATION: (1)..(720)
<223> OTHER INFORMATION: GFP

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 2
<211> LENGTH: 239
<212> TYPE: PRT
<213> ORGANISM: Aequorea victoria
<220> FEATURE:
```

<221> NAME/KEY: MISC_FEATURE
<222> LOCATION: (1)..(239)
<223> OTHER INFORMATION: GFP

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 3
<211> LENGTH: 798
<212> TYPE: DNA
<213> ORGANISM: Escherichia coli
<220> FEATURE:
<221> NAME/KEY: misc_feature
<222> LOCATION: (1)..(795)
<223> OTHER INFORMATION: NPTII

<400> SEQUENCE: 3
atggggattg aacaagatgg attgcacgca ggttctccgg ccgcttgggt ggagaggcta      60
ttcggctatg actgggcaca acagacaatc ggctgctctg atgccgccgt gttccggctg     120
tcagcgcagg ggcgcccggt tctttttgtc aagaccgacc tgtccggtgc cctgaatgaa     180
ctccaggacg aggcagcgcg gctatcgtgg ctggccacga cgggcgttcc ttgcgcagct     240
gtgctcgacg ttgtcactga agcgggaagg gactggctgc tattgggcga agtgccgggg     300
caggatctcc tgtcatctca ccttgctcct gccgagaaag tatccatcat ggctgatgca     360
atgcggcggc tgcatacgct tgatccggct acctgcccat tcgaccacca agcgaaacat     420
cgcatcgagc gagcacgtac tcggatggaa gccggtcttg tcgatcagga tgatctggac     480

```
gaagagcatc agggctcgc gccagccgaa ctgttcgcca ggctcaaggc gcgcatgccc      540
gacggcgagg atctcgtcgt gacacatggc gatgcctgct tgccgaatat catggtggaa      600
aatggccgct tttctggatt catcgactgt ggccggctgg gtgtggcgga ccgctatcag      660
gacatagcgt tggctacccg tgatattgct gaagagcttg gcggcgaatg ggctgaccgc      720
ttcctcgtgc tttacggtat cgccgctccc gattcgcagc gcatcgcctt ctatcgcctt      780
cttgacgagt tcttctga                                                    798
```

<210> SEQ ID NO 4
<211> LENGTH: 265
<212> TYPE: PRT
<213> ORGANISM: Escherichia coli
<220> FEATURE:
<221> NAME/KEY: MISC_FEATURE
<222> LOCATION: (1)..(265)
<223> OTHER INFORMATION: NPTII

<400> SEQUENCE: 4

```
Met Gly Ile Glu Gln Asp Gly Leu His Ala Gly Ser Pro Ala Ala Trp
1               5                   10                  15

Val Glu Arg Leu Phe Gly Tyr Asp Trp Ala Gln Gln Thr Ile Gly Cys
            20                  25                  30

Ser Asp Ala Ala Val Phe Arg Leu Ser Ala Gln Gly Arg Pro Val Leu
        35                  40                  45

Phe Val Lys Thr Asp Leu Ser Gly Ala Leu Asn Glu Leu Gln Asp Glu
    50                  55                  60

Ala Ala Arg Leu Ser Trp Leu Ala Thr Thr Gly Val Pro Cys Ala Ala
65                  70                  75                  80

Val Leu Asp Val Val Thr Glu Ala Gly Arg Asp Trp Leu Leu Leu Gly
                85                  90                  95

Glu Val Pro Gly Gln Asp Leu Leu Ser Ser His Leu Ala Pro Ala Glu
            100                 105                 110

Lys Val Ser Ile Met Ala Asp Ala Met Arg Arg Leu His Thr Leu Asp
        115                 120                 125

Pro Ala Thr Cys Pro Phe Asp His Gln Ala Lys His Arg Ile Glu Arg
    130                 135                 140

Ala Arg Thr Arg Met Glu Ala Gly Leu Val Asp Gln Asp Asp Leu Asp
145                 150                 155                 160

Glu Glu His Gln Gly Leu Ala Pro Ala Glu Leu Phe Ala Arg Leu Lys
                165                 170                 175

Ala Arg Met Pro Asp Gly Glu Asp Leu Val Val Thr His Gly Asp Ala
            180                 185                 190

Cys Leu Pro Asn Ile Met Val Glu Asn Gly Arg Phe Ser Gly Phe Ile
        195                 200                 205

Asp Cys Gly Arg Leu Gly Val Ala Asp Arg Tyr Gln Asp Ile Ala Leu
    210                 215                 220

Ala Thr Arg Asp Ile Ala Glu Glu Leu Gly Gly Glu Trp Ala Asp Arg
225                 230                 235                 240

Phe Leu Val Leu Tyr Gly Ile Ala Ala Pro Asp Ser Gln Arg Ile Ala
                245                 250                 255

Phe Tyr Arg Leu Leu Asp Glu Phe Phe
            260                 265
```

<210> SEQ ID NO 5
<211> LENGTH: 552
<212> TYPE: DNA

<213> ORGANISM: Streptomyces viridochromogenes
<220> FEATURE:
<221> NAME/KEY: misc_feature
<222> LOCATION: (1)..(552)
<223> OTHER INFORMATION: pat gene

<400> SEQUENCE: 5

```
atgagcccag aacgacgccc ggtcgagatc cgtcccgcca ccgccgccga catggcggcg      60
gtctgcgaca tcgtcaatca ctacatcgag acgagcacgg tcaacttccg tacgagccg     120
cagactccgc aggagtggat cgacgacctg gagcgcctcc aggaccgcta ccctggctc     180
gtcgccgagg tggagggcgt cgtcgccggc atcgcctacg ccggcccctg gaaggcccgc     240
aacgcctacg actggaccgt cgagtcgacg gtgtacgtct ccaccggca ccagcggctc     300
ggactgggct ccaccctcta cacccacctg ctgaagtcca tggaggccca gggcttcaag     360
agcgtggtcg ccgtcatcgg actgcccaac gacccgagcg tgcgcctgca cgaggcgctc     420
ggatacaccg cgcgcgggac gctgcgggca gccggctaca agcacggggg ctggcacgac     480
gtggggttct ggcagcgcga cttcgagctg ccggccccgc ccgcccgt ccggcccgtc     540
acacagatct ga                                                         552
```

<210> SEQ ID NO 6
<211> LENGTH: 183
<212> TYPE: PRT
<213> ORGANISM: Streptomyces viridochromogenes
<220> FEATURE:
<221> NAME/KEY: MISC_FEATURE
<222> LOCATION: (1)..(183)
<223> OTHER INFORMATION: pat

<400> SEQUENCE: 6

```
Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
            20                  25                  30

Thr Val Asn Phe Arg Thr Glu Pro Gln Thr Pro Gln Glu Trp Ile Asp
        35                  40                  45

Asp Leu Glu Arg Leu Gln Asp Arg Tyr Pro Trp Leu Val Ala Glu Val
    50                  55                  60

Glu Gly Val Val Ala Gly Ile Ala Tyr Ala Gly Pro Trp Lys Ala Arg
65                  70                  75                  80

Asn Ala Tyr Asp Trp Thr Val Glu Ser Thr Val Tyr Val Ser His Arg
                85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
        115                 120                 125

Pro Asn Asp Pro Ser Val Arg Leu His Glu Ala Leu Gly Tyr Thr Ala
    130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
            180
```

<210> SEQ ID NO 7
<211> LENGTH: 1026

```
<212> TYPE: DNA
<213> ORGANISM: Escherichia coli
<220> FEATURE:
<221> NAME/KEY: misc_feature
<222> LOCATION: (1)..(1026)
<223> OTHER INFORMATION: hptII

<400> SEQUENCE: 7
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggagttta gcgagagcct gacctattgc atctcccgcc gtgcacaggg tgtcacgttg     300
caagacctgc ctgaaaccga actgcccgct gttctacaac cggtcgcgga ggctatggat     360
gcgatcgctg cggccgatct tagccagacg agcgggttcg cccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg gagcgaggcg     660
atgttcgggg attcccaata cgaggtcgcc aacatcttct tctggaggcc gtggttggct     720
tgtatggagc agcagacgcg ctacttcgag cggaggcatc cggagcttgc aggatcgcca     780
cgactccggg cgtatatgct ccgcattggt cttgaccaac tctatcagag cttggttgac     840
ggcaatttcg atgatgcagc ttgggcgcag gtcgatgcg acgcaatcgt ccgatccgga     900
gccgggactg tcgggcgtac acaaatcgcc cgcagaagcg cggccgtctg gaccgatggc     960
tgtgtagaag tactcgccga tagtggaaac cgacgcccca gcactcgtcc gagggcaaag    1020
aaatag                                                               1026
```

```
<210> SEQ ID NO 8
<211> LENGTH: 341
<212> TYPE: PRT
<213> ORGANISM: Escherichia coli
<220> FEATURE:
<221> NAME/KEY: MISC_FEATURE
<222> LOCATION: (1)..(341)
<223> OTHER INFORMATION: hptII

<400> SEQUENCE: 8

Met Lys Lys Pro Glu Leu Thr Ala Thr Ser Val Glu Lys Phe Leu Ile
1               5                  10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
```

```
                    115                 120                 125
Gln Thr Ser Gly Phe Gly Pro Phe Gly Pro Gln Gly Ile Gly Gln Tyr
            130                 135                 140
Thr Thr Trp Arg Asp Phe Ile Cys Ala Ile Ala Asp Pro His Val Tyr
145                 150                 155                 160
His Trp Gln Thr Val Met Asp Asp Thr Val Ser Ala Ser Val Ala Gln
                165                 170                 175
Ala Leu Asp Glu Leu Met Leu Trp Ala Glu Asp Cys Pro Glu Val Arg
            180                 185                 190
His Leu Val His Ala Asp Phe Gly Ser Asn Asn Val Leu Thr Asp Asn
        195                 200                 205
Gly Arg Ile Thr Ala Val Ile Asp Trp Ser Glu Ala Met Phe Gly Asp
    210                 215                 220
Ser Gln Tyr Glu Val Ala Asn Ile Phe Phe Trp Arg Pro Trp Leu Ala
225                 230                 235                 240
Cys Met Glu Gln Gln Thr Arg Tyr Phe Glu Arg Arg His Pro Glu Leu
                245                 250                 255
Ala Gly Ser Pro Arg Leu Arg Ala Tyr Met Leu Arg Ile Gly Leu Asp
            260                 265                 270
Gln Leu Tyr Gln Ser Leu Val Asp Gly Asn Phe Asp Asp Ala Ala Trp
        275                 280                 285
Ala Gln Gly Arg Cys Asp Ala Ile Val Arg Ser Gly Ala Gly Thr Val
    290                 295                 300
Gly Arg Thr Gln Ile Ala Arg Arg Ser Ala Ala Val Trp Thr Asp Gly
305                 310                 315                 320
Cys Val Glu Val Leu Ala Asp Ser Gly Asn Arg Arg Pro Ser Thr Arg
                325                 330                 335
Pro Arg Ala Lys Lys
            340

<210> SEQ ID NO 9
<211> LENGTH: 10711
<212> TYPE: DNA
<213> ORGANISM: artificial
<220> FEATURE:
<223> OTHER INFORMATION: synthetic sequence
<220> FEATURE:
<221> NAME/KEY: misc_feature
<222> LOCATION: (1)..(10711)
<223> OTHER INFORMATION: 131440 plant transformation vector

<400> SEQUENCE: 9
catgccaacc acagggttcc cctcgggatc aaagtacttt gatccaaccc ctccgctgct    60
atagtgcagt cggcttctga cgttcagtgc agccgtcttc tgaaaacgac atgtcgcaca   120
agtcctaagt tacgcgacag gctgccgccc tgccctttc ctggcgtttt cttgtcgcgt    180
gttttagtcg cataaagtag aatacttgcg actagaaccg agacattac gccatgaaca    240 agagcgccgc cgctggcctg ctgggctatg cccgcgtcag caccgacgac caggacttga    300
ccaaccaacg ggccgaactg cacgcggccg gctgcaccaa gctgttttcc gagaagatca    360
ccggcaccag gcgcgaccgc ccggagctgg ccaggatgct tgaccaccta cgccctggcg    420
acgttgtgac agtgaccagg ctagaccgcc tggcccgcag cacccgcgac tactggaca    480 ttgccgagcg catccaggag gccggcgcgg gcctgcgtag cctggcagag ccgtgggccg    540
acaccaccac gccggccggc cgcatggtgt tgaccgtgtt cgccggcatt gccgagttcg    600
agcgttccct aatcatcgac cgcacccgga gcgggcgcga ggccgccaag gcccgaggcg    660
```

```
tgaagtttgg cccccgccct accctcaccc cggcacagat cgcgcacgcc cgcgagctga    720
tcgaccagga aggccgcacc gtgaaagagg cggctgcact gcttggcgtg catcgctcga    780
ccctgtaccg cgcacttgag cgcagcgagg aagtgacgcc caccgaggcc aggcggcgcg    840
gtgccttccg tgaggacgca ttgaccgagg ccgacgccct ggcggccgcc gagaatgaac    900
gccaagagga acaagcatga aaccgcacca ggacggccag gacgaaccgt ttttcattac    960
cgaagagatc gaggcggaga tgatcgcggc cgggtacgtg ttcgagccgc ccgcgcacgt   1020
ctcaaccgtg cggctgcatg aaatcctggc cggtttgtct gatgccaagc tggcggcctg   1080 gccgccagce ttggccgctg aagaaaccga gcgccgccgt ctaaaaaggt gatgtgtatt   1140
tgagtaaaac agcttgcgtc atgcggtcgc tgcgtatatg atgcgatgag taaataaaca   1200
aatacgcaag gggaacgcat gaaggttatc gctgtactta accagaaagg cgggtcaggc   1260
aagacgacca tcgcaaccca tctagcccgc gccctgcaac tcgccggggc cgatgttctg   1320
ttagtcgatt ccgatcccca gggcagtgcc cgcgattggg cggccgtgcg ggaagatcaa   1380
ccgctaaccg ttgtcggcat cgaccgcccg acgattgacc gcgacgtgaa ggccatcggc   1440
cggcgcgact tcgtagtgat cgacggagcg ccccaggcgg cggacttggc tgtgtccgcg   1500
atcaaggcag ccgacttcgt gctgattccg gtgcagccaa gcccttacga catatgggcc   1560
accgccgacc tggtggagct ggttaagcag cgcattgagg tcacggatgg aaggctacaa   1620
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca gcccgagga atcggcgtga   2280 cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacagcttc cagacgggca   2640 cgtagaggtt tccgcagggc cggccggcat ggccagtgtg tgggattacg acctggtact   2700
gatggcggtt tccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccagggtga   2940 agccttgatt agccgctaca agatcgtaaa gagcgaaacc gggcggccgg agtacatcga   3000
```

```
gatcgagcta gctgattgga tgtaccgcga gatcacagaa ggcaagaacc cggacgtgct    3060
gacggttcac cccgattact ttttgatcga tcccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240
aaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaggtcga aaaggtctct ttcctgtgga     3420
tagcacgtac attgggaacc caaagccgta cattgggaac cggaacccgt acattgggaa    3480
cccaaagccg tacattggga accggtcaca catgtaagtg actgatataa aagagaaaaa    3540
aggcgatttt tccgcctaaa actctttaaa acttattaaa actcttaaaa cccgcctggc    3600
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accaggcgc ggacaagccg cgccgtcgcc     3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca agcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt ttttgtttg caagcagcag attacgcgca gaaaaaaagg     4860
atctcaagaa gatcctttga tcttttctac ggggtctgac gctcagtgga acgaaaactc    4920
acgttaaggg attttggtca tgcattctag gtactaaaac aattcatcca gtaaatata     4980 atattttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat ctttcacaaa    5160
gatgttgctg tctcccaggt cgccgtggga aaagacaagt tcctcttcgg cttttccgt     5220 ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
```

```
cgcatacagc tcgataatct tttcagggct tgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtccttt cccgttccac    5580 atcataggtg gtcccttat accggctgtc cgtcattttt aaatataggt tttcatttc    5640 tcccaccagc ttatatacct tagcaggaga cattccttcc gtatctttta cgcagcggta    5700
tttttcgatc agtttttca attccggtga tattctcatt ttagccattt attatttcct    5760
tcctcttttc tacagtattt aaagataccc caagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cgggagctg ttggctggct ggtgacagga    6180
tatattgttg tgttaacaaa ttgacgctta gacaacttaa taacacattg cggacgtttt    6240
taatgtactg aattaacgcc gaattaattc gggggatctg gattttagta ctggattttg    6300
gttttaggaa ttagaaattt tattgataga agtattttac aaatacaaat acatactaag    6360
ggtttcttat atgctcaaca catgagcgaa accctatagg aaccctaatt cccttatctg    6420
ggaactactc acacattatt atggagaaac tcgagcttgt cgatcgactc tagctagagg    6480
atcgatccga accccagagt cccgctcaga agaactcgtc aagaaggcga tagaaggcga    6540
tgcgctgcga atcgggagcg gcgataccgt aaagcacgag gaagcggtca gcccattcgc    6600
cgccaagctc ttcagcaata tcacgggtag ccaacgctat gtcctgatag cggtccgcca    6660
cacccagccg gccacagtcg atgaatccag aaaagcggcc attttccacc atgatattcg    6720
gcaagcaggc atcgccatgt gtcacgacga gatcctcgcc gtcgggcatg cgcgccttga    6780
gcctggcgaa cagttcggct ggcgcgagcc cctgatgctc ttcgtccaga tcatcctgat    6840
cgacaagacc ggcttccatc cgagtacgtg ctcgctcgat gcgatgtttc gcttggtggt    6900
cgaatgggca ggtagccgga tcaagcgtat gcagccgccg cattgcatca gccatgatgg    6960
atactttctc ggcaggagca aggtgagatg acaggagatc ctgccccggc acttcgccca    7020
atagcagcca gtcccttccc gcttcagtga caacgtcgag cacagctgcg caaggaacgc    7080
ccgtcgtggc cagccacgat agccgcgctg cctcgtcctg gagttcattc agggcaccgg    7140
acaggtcggt cttgacaaaa agaaccgggc gcccctgcgc tgacagccgg aacacggcgg    7200
catcagagca gccgattgtc tgttgtgccc agtcatagcc gaatagcctc tccacccaag    7260
cggccggaga acctgcgtgc aatccatctt gttcaatccc catggtcgat cgacagatct    7320 gcgaagctc gagagagata gatttgtaga gagagactgg tgatttcagc gtgtcctctc    7380
caaatgaaat gaacttcctt atatagagga aggtcttgcg aaggatagtg ggattgtgcg    7440 tcatcccta cgtcagtgga gatatcacat caatccactt gctttgaaga cgtggttgga    7500
acgtcttctt tttccacgat gctcctcgtg ggtgggggtc catctttggg accactgtcg    7560
gcagaggcat cttgaacgat agcctttcct ttatcgcaat gatggcattt gtaggtgcca    7620
ccttcctttt ctactgtcct tttgatgaag tgacagatag ctgggcaatg gaatccgagg    7680
aggtttcccg atattaccct tgttgaaaaa gtctcaatag ccctttggtc ttctgagact    7740
```

-continued

```
gtatctttga tattcttgga gtagacgaga gtgtcgtgct ccaccatgtt atcacatcaa    7800
tccacttgct ttgaagacgt ggttggaacg tcttctttttt ccacgatgct cctcgtgggt    7860
gggggtccat ctttgggacc actgtcggca gaggcatctt gaacgatagc ctttcctttta   7920 tcgcaatgat ggcatttgta ggtgccacct ccttttcta ctgtccttttt gatgaagtga    7980 cagatagctg ggcaatggaa tccgaggagg tttcccgata ttacccttttg ttgaaaagtc   8040 tcaatagccc tttggtcttc tgagactgta tcttttgatat tcttggagta acgagagtg    8100 tcgtgctcca ccatgttggc aagctgctct agccaatacg caaaccgcct ctccccgcgc    8160
gttggccgat tcattaatgc agctggcacg acaggtttcc cgactggaaa gcggcagtg    8220 agcgcaacgc aattaatgtg agttagctca ctcattaggc accccaggct ttacacttta   8280
tgcttccggc tcgtatgttg tgtggaattg tgagcggata caatttcac acaggaaaca    8340 gctatgacca tgattacgaa ttcgagctct aactataacg gtcctaaggt agcgagcgat    8400
cgcgcgtatt ggctagagca gcttgccaac atggtggagc acgacactct cgtctactcc    8460
aagaatatca aagatacagt ctcagaagac caaagggcta ttgagacttt tcaacaaagg    8520
gtaatatcgg gaaacctcct cggattccat tgcccagcta tctgtcactt catcaaaagg    8580
acagtagaaa aggaaggtgg cacctacaaa tgccatcatt gcgataaagg aaaggctatc    8640
gttcaagatg cctctgccga cagtggtccc aaagatggac ccccacccac gaggagcatc    8700
gtggaaaaag aagacgttcc aaccacgtct tcaaagcaag tggattgatg tgaacatggt    8760
ggagcacgac actctcgtct actccaagaa tatcaaagat acagtctcag aagaccaaag    8820
ggctattgag acttttcaac aaagggtaat atcgggaaac ctcctcggat tccattgccc    8880
agctatctgt cacttcatca aaaggacagt agaaaaggaa ggtggcacct acaaatgcca    8940
tcattgcgat aaaggaaagg ctatcgttca agatgcctct gccgacagtg gtcccaaaga    9000
tggaccccca cccacgagga gcatcgtgga aaaagaagac gttccaacca cgtcttcaaa    9060
gcaagtggat tgatgtgata tctccactga cgtaagggat gacgcacaat cccactatcc    9120
ttcgcaagac ccttcctcta tataaggaag ttcatttcat ttggagagga cacgctgaaa    9180
tcaccagtct ctctctacaa atctatctct gtttaaacat ggtgagcaag ggcgaggagc    9240
tgttcaccgg ggtggtgccc atcctggtcg agctggacgg cgacgtaaac ggccacaagt    9300
tcagcgtgtc cggcgagggc gagggcgatg ccacctacgg caagctgacc ctgaagttca    9360
tctgcaccac cggcaagctg cccgtgccct ggcccaccct cgtgaccacc ctgacctacg    9420
gcgtgcagtg cttcagccgc taccccgacc acatgaagca gcacgacttc ttcaagtccg    9480
ccatgcccga aggctacgtc caggagcgca ccatcttctt caaggacgac ggcaactaca    9540
agacccgcgc cgaggtgaag ttcgagggcg acacccctggt gaaccgcatc gagctgaagg    9600
gcatcgactt caaggaggac ggcaacatcc tggggcacaa gctggagtac aactacaaca    9660
gccacaacgt ctatatcatg gccgacaagc agaagaacgg catcaaggtg aacttcaaga    9720
tccgccacaa catcgaggac ggcagcgtgc agctcgccga ccactaccag cagaacaccc    9780
ccatcggcga cggccccgtg ctgctgcccg acaaccacta cctgagcacc cagtccgccc    9840
tgagcaaaga cccaacgag aagcgcgatc acatggtcct gctggagttc gtgaccgccg    9900
ccgggatcac tctcggcatg gacgagctgt acaagtaacg gaccggatct gtcgatcgac    9960
aagctcgagt ttctccataa taatgtgtga gtagttccca gataagggaa ttagggttcc   10020
tatagggttt cgctcatgtg ttgagcatat aagaaaccct tagtatgtat ttgtatttgt   10080
aaaatacttc tatcaataaa atttctaatt cctaaaacca aaatccagta ctaaaatcca   10140
```

```
gatccccga attagcggcc gcattaccct gttatccta ctttcggatt ataacatcac    10200
atctatgtcg ggtgcggaga aagaggtaat gaaatggcat gacgatcaac cataccagat    10260
aactatgact ctcttaaggt agccaaataa tacccggtct gaacgaggtg gcaaacagct    10320
attatgggta ttatgggtgg tacccgggga tcctctagag tcgacctgca ggcatgcaag    10380
cttggcactg gccgtcgttt tacaacgtcg tgactgggaa aaccctggcg ttacccaact    10440
taatcgcctt gcagcacatc cccctttcgc cagctggcgt aatagcgaag aggcccgcac    10500
cgatcgccct tcccaacagt tgcgcagcct gaatggcgaa tgctagagca gcttgagctt    10560
ggatcagatt gtcgtttccc gccttcagtt taaactatca gtgtttgaca ggatatattg    10620
gcgggtaaac ctaagagaaa agagcgttta ttagaataac ggatatttaa agggcgtga    10680 aaaggtttat ccgttcgtcc atttgtatgt g                                  10711

<210> SEQ ID NO 10
<211> LENGTH: 13247
<212> TYPE: DNA
<213> ORGANISM: artificial
<220> FEATURE:
<223> OTHER INFORMATION: synthetic vector sequence
<220> FEATURE:
<221> NAME/KEY: misc_feature
<222> LOCATION: (1)..(13247)
<223> OTHER INFORMATION: 130571 plant transformation vector

<400> SEQUENCE: 10
ttatccctac tttcggatta taacatcaca tctatgtcgg gtgcggagaa agaggtaatg      60
aaatggcatg acgatcaacc ataccagata actatgactc tcttaaggta gccaaataat     120
acccggtctg aacgaggtgg caaacagcta ttatgggtat tatgggtggt acccggggat     180
cctctagagt cgacctgcag gcatgcaagc ttggcactgg ccgtcgtttt acaacgtcgt     240
gactgggaaa accctggcgt tacccaactt aatcgcttg cagcacatcc cctttcgcc       300 agctggcgta atagcgaaga ggcccgcacc gatcgccctt cccaacagtt gcgcagcctg     360
aatggcgaat gctagagcag cttgagcttg atcagattg tcgtttccg ccttcagttt      420 aaactatcag tgtttgacag gatatattgg cgggtaaacc taagagaaaa gagcgttat      480 tagaataatc ggatatttaa agggcgtga aaaggtttat ccgttcgtcc atttgtatgt     540
gcatgccaac cacagggttc ccctcgggag tgcttggcat tccgtgcgat aatgacttct     600
gttcaaccac ccaaacgtcg gaaagcctga cgacggagca gcattccaaa aagatccctt     660
ggctcgtctg ggtcggctag aaggtcgagt gggctgctgt ggcttgatcc ctcaacgcgg     720
tcgcggacgt agcgcagcgc cgaaaaatcc tcgatcgcaa atccgacgct gtcgaaaagc     780
gtgatctgct tgtcgctctt tcggccgacg tcctggccag tcatcacgcg ccaaagttcc     840
gtcacaggat gatctggcgc gagttgctgg atctcgcctt caatccgggt ctgtggcggg     900
aactccacga aaatatccga acgcagcaag atcgtcgacc aattcttgaa gacgaaaggg     960
cctcgtgata cgcctatttt tataggttaa tgtcatgata ataatggttt cttagacgtc    1020
aggtggcact tttcgggaa atgtgcgcgg aaccccctatt tgtttatttt tctaaataca    1080
ttcaaatatg tatccgctca tgagacaata accctgataa atgcttcaat aatattgaaa    1140
aaggaagagt atgagtattc aacatttccg tgtcgccctt attcccttttt tgcggcatt    1200 ttgccttcct gttttttgctc acccagaaac gctggtgaaa gtaaaagatg ctgaagatca    1260
gttgggtgca cgagtgggtt acatcgaact ggatctcaac agcggtaaga tccttgagag    1320
```

```
tttcgcccc gaagaacgtt ttccaatgat gagcactttt aaagttctgc tatgtggcgc    1380
ggtattatcc cgtgttgacg ccgggcaaga gcaactcggt cgccgcatac actattctca    1440
gaatgacttg gttgagtact caccagtcac agaaaagcat cttacggatg gcatgacagt    1500
aagagaatta tgcagtgctg ccataaccat gagtgataac actgcggcca acttacttct    1560
gacaacgatc ggaggaccga aggagctaac cgcttttttg cacaacatgg gggatcatgt    1620
aactcgcctt gatcgttggg aaccggagct gaatgaagcc ataccaaacg acgagcgtga    1680
caccacgatg cctgcagggg ggggggggg gggacatgag gttgcccgt attcagtgtc    1740
gctgatttgt attgtctgaa gttgttttta cgttaagttg atgcagatca attaatacga    1800
tacctgcgtc ataattgatt atttgacgtg gtttgatggc ctccacgcac gttgtgatat    1860
gtagatgata atcattatca ctttacgggt ccttttccggt gatccgacag gttacggggc    1920
ggcgacctcg cgggttttcg ctatttatga aaattttccg gtttaaggcg tttccgttct    1980
tcttcgtcat aacttaatgt ttttatttaa aataccctct gaaaagaaag gaaacgacag    2040
gtgctgaaag cgagcttttt ggcctctgtc gtttcctttc tctgtttttg tccgtggaat    2100
gaacaatgga accccccccc cccccccct gcagcaatgg caacaacgtt gcgcaaacta    2160
ttaactggcg aactacttac tctagcttcc cggcaacaat taatagactg gatggaggcg    2220
gataaagttg caggaccact tctgcgctcg gcccttccgg ctggctggtt tattgctgat    2280
aaatctggag ccggtgagcg tgggtctcgc ggtatcattg cagcactggg gccagatggt    2340
aagccctccc gtatcgtagt tatctacacg acggggagtc aggcaactat ggatgaacga    2400
aatagacaga tcgctgagat aggtgcctca ctgattaagc attggtaact gtcagaccaa    2460
gtttactcat atatacttta gattgattta aaacttcatt tttaatttaa aaggatctag    2520
gtgaagatcc ttttgataa tctcatgacc aaaatccctt aacgtgagtt ttcgttccac    2580
tgagcgtcag accccgtaga aaagatcaaa ggatcttctt gagatccttt ttttctgcgc    2640
gtaatctgct gcttgcaaac aaaaaaacca ccgctaccag cggtggtttg tttgccggat    2700
caagagctac caactctttt tccgaaggta actggcttca gcagagcgca gataccaaat    2760
actgtccttc tagtgtagcc gtagttaggc caccacttca agaactctgt agcaccgcct    2820
acatacctcg ctctgctaat cctgttacca gtggctgctg ccagtggcga taagtcgtgt    2880
cttaccgggt tggactcaag acgatagtta ccggataagg cgcagcggtc gggctgaacg    2940
gggggttcgt gcacacagcc cagcttggag cgaacgacct acaccgaact gagataccta    3000
cagcgtgagc tatgagaaag cgccacgctt cccgaaggga gaaaggcgga caggtatccg    3060
gtaagcggca gggtcggaac aggagagcgc acgagggagc ttccagggggg aaacgcctgg    3120
tatctttata gtcctgtcgg gtttcgccac ctctgacttg agcgtcgatt tttgtgatgc    3180
tcgtcagggg ggcggagcct atggaaaaac gccagcaacg cggccttttt acggttcctg    3240
gccttttgct ggccttttgc tcacatgttc tttcctgcgt tatcccctga ttctgtggat    3300
aaccgtatta ccgcctttga gtgagctgat accgctcgcc gcagccgaac gaccgagcgc    3360
agcgagtcag tgagcgagga agcggaagag cgcctgatgc ggtattttct ccttacgcat    3420
ctgtgcggta tttcacaccg catatggtgc actctcagta caatctgctc tgatgccgca    3480
tagttaagcc agtatacact ccgctatcgc tacgtgactg ggtcatggct gcgccccgac    3540
acccgccaac acccgctgac gcgccctgac gggcttgtct gctcccggca tccgcttaca    3600
gacaagctgt gaccgtctcc gggagctgca tgtgtcagag gttttcaccg tcatcaccga    3660
aacgcgcgag gcagcagatc ccccgatcaa gtagatacac tacatatatc tacaatagac    3720
```

```
atcgagccgg aaggtgatgt ttactttcct gaaatcccca gcaattttag gccagttttt    3780
acccaagact tcgcctctaa cataaattat agttaccaaa tctggcaaaa gggttaacaa    3840
gtggcagcaa cggattcgca aacctgtcac gccttttgtg ccaaaagccg cgccaggttt    3900
gcgatccgct gtgccaggcg ttaggcgtca tatgaagatt tcggtgatcc ctgagcaggt    3960
ggcggaaaca ttggatgctg agaaccattt cattgttcgt gaagtgttcg atgtgcacct    4020
atccgaccaa ggctttgaac tatctaccag aagtgtgagc ccctaccgga aggattacat    4080
ctcggatgat gactctgatg aagactctgc ttgctatggc gcattcatcg accaagagct    4140
tgtcgggaag attgaactca actcaacatg aacgatcta gcctctatcg aacacattgt    4200
tgtgtcgcac acgcaccgag gcaaaggagt cgcgcacagt ctcatcgaat ttgcgaaaaa    4260
gtgggcacta agcagacagc tccttggcat acgattagag acacaaacga caatgtacc    4320 tgcctgcaat ttgtacgcaa aatgtggctt tactctcggc ggcattgacc tgttcacgta    4380
taaaactaga cctcaagtct cgaacgaaac agcgatgtac tggtactggt tctcgggagc    4440
acaggatgac gcctaacaat tcattcaagc cgacaccgct tcgcggcgcg gcttaattca    4500
ggagttaaac atcatgaggg aagcggtgat cgccgaagta tcgactcaac tatcagaggt    4560
agttggcgtc atcgagcgcc atctcgaacc gacgttgctg gccgtacatt tgtacggctc    4620
cgcagtggat ggcggcctga agccacacag tgatattgat ttgctggtta cggtgaccgt    4680
aaggcttgat gaaacaacgc ggcgagcttt gatcaacgac cttttggaaa cttcggcttc    4740
ccctggagag agcgagattc tccgcgctgt agaagtcacc attgttgtgc acgacgacat    4800
cattccgtgg cgttatccag ctaagcgcga actgcaattt ggagaatggc agcgcaatga    4860
cattcttgca ggtatcttcg agccagccac gatcgacatt gatctggcta tcttgctgac    4920
aaaagcaaga gaacatagcg ttgccttggt aggtccagcg gcggaggaac tctttgatcc    4980
ggttcctgaa caggatctat ttgaggcgct aaatgaaacc ttaacgctat ggaactcgcc    5040
gcccgactgg gctggcgatg agcgaaatgt agtgcttacg ttgtcccgca tttggtacag    5100
cgcagtaacc ggcaaaatcg cgccgaagga tgtcgctgcc gactgggcaa tggagcgcct    5160
gccggcccag tatcagcccg tcatacttga agctaggcag gcttatcttg acaagaaga    5220 tcgcttggcc tcgcgcgcag atcagttgga agaatttgtt cactacgtga aaggcgagat    5280
caccaaggta gtcggcaaat aatgtctaac aattcgttca agccgacgcc gcttcgcggc    5340
gcggcttaac tcaagcgtta gagagctggg gaagactatg cgcgatctgt tgaaggtggt    5400
tctaagcctc gtacttgcga tggcatcggg gcaggcactt gctgacctgc caattgtttt    5460
agtggatgaa gctcgtcttc cctatgacta ctccccatcc aactacgaca tttctccaag    5520
caactacgac aactccataa gcaattacga caatagtcca tcaaattacg acaactctga    5580
gagcaactac gataatagtt catccaatta cgacaatagt cgcaacggaa atcgtaggct    5640
tatatatagc gcaaatgggt ctcgcacttt cgccggctac tacgtcattg ccaacaatgg    5700
gacaacgaac ttcttttcca catctggcaa aaggatgttc tacaccccaa aagggggcg    5760 cggcgtctat ggcggcaaag atgggagctt ctgcggggca ttggtcgtca taaatggcca    5820
attttcgctt gccctgacag ataacggcct gaagatcatg tatctaagca actagcctgc    5880
tctctaataa aatgttaggc ctcaacatct agtcgcaagc tgagggggaac cactagtgtc    5940 atacgaacct ccaagagacg gttacacaaa cgggtacatt gttgatgtca tgtatgacaa    6000
tcgcccaagt aagtatccag ctgtgttcag aacgtacgtc cgaattaatt catcggggta    6060
```

```
cggtcgacga tcgtcaacgt tcacttctaa agaaatagcg ccactcagct tcctcagcgg    6120
ctttatccag cgatttccta ttatgtcggc atagttctca agatcgacag cctgtcacgg    6180
ttaagcgaga atgaataag aaggctgata attcggatct ctgcgaggga gatgatattt    6240
gatcacaggc agcaacgctc tgtcatcgtt acaatcaaca tgctaccctc cgcgagatca    6300
tccgtgtttc aaacccggca gcttagttgc cgttcttccg aatagcatcg gtaacatgag    6360
caaagtctgc cgccttacaa cggctctccc gctgacgccg tcccggactg atgggctgcc    6420
tgtatcgagt ggtgattttg tgccgagctg ccggtcgggg agctgttggc tggctggtgg    6480
caggatatat tgtggtgtaa acaaattgac gcttagacaa cttaataaca cattgcggac    6540
gtttttaatg tactgaattc ccgggacttc cgattaagta gagcttcccc tgccgaagcg    6600
cgtggagcta caacccaaac ctgcagctga attaacgccg aattaattcg ggggatctgg    6660
attttagtac tggattttgg ttttaggaat tagaaatttt attgatagaa gtattttaca    6720
aatacaaata catactaagg gtttcttata tgctcaacac atgagcgaaa ccctatagga    6780
accctaattc ccttatctgg gaactactca cacattatta tggagaaact cgagtcagat    6840
ctgtgtgacg ggccggacgg ggcggggcgg ggccggcagc tcgaagtcgc gctgccagaa    6900
ccccacgtcg tgccagcccc cgtgcttgta gccggctgcc cgcagcgtcc cgcgcgcggt    6960
gtatccgagc gcctcgtgca ggcgcacgct cgggtcgttg ggcagtccga tgacggcgac    7020
cacgctcttg aagccctggg cctccatgga cttcagcagg tgggtgtaga gggtggagcc    7080
cagtccgagc cgctggtgcc ggtgggagac gtacaccgtc gactcgacgg tccagtcgta    7140
ggcgttgcgg gccttccagg ggccggcgta ggcgatgccg cgacgacgc cctccacctc    7200 ggcgacgagc caggggtagc ggtcctggag gcgctccagg tcgtcgatcc actcctgcgg    7260
agtctgcggt ccgtacgga agttgaccgt gctcgtctcg atgtagtgat tgacgatgtc    7320
gcagaccgcc gccatgtcgg cggcggtggc gggacggatc tcgaccgggc gtcgttctgg    7380
gctcataagc ttatcgtcta cctgcagaag taacaccaaa caacagggtg agcatcgaca    7440
aaagaaacag taccaagcaa ataaatagcg tatgaaggca gggctaaaaa aatccacata    7500
tagctgctgc atatgccatc atccaagtat atcaagatca aaataattat aaaacatact    7560
tgtttattat aatagatagg tactcaaggt tagagcatat gaatagatgc tgcatatgcc    7620
atcatgtata tgcatcagta aaacccacat caacatgtat acctatccta gatcgatatt    7680
tccatccatc ttaaactcgt aactatgaag atgtatgaca cacacataca gttccaaaat    7740
taataaatac accaggtagt ttgaaacagt attctactcc gatctagaac gaatgaacga    7800
ccgcccaacc acaccacatc atcacaacca agcgaacaaa aagcatctct gtatatgcat    7860
cagtaaaacc cgcatcaaca tgtataccta tcctagatcg atatttccat ccatcatctt    7920
caattcgtaa ctatgaatat gtatggcaca cacatacaga tccaaaatta ataaatccac    7980
caggtagttt gaaacagaat tctactccga tctagaacga ccgcccaacc agaccacatc    8040
atcacaacca agacaaaaaa aagcatgaaa agatgacccg acaaacaagt gcacggcata    8100
tattgaaata aaggaaaagg gcaaaccaaa ccctatgcaa cgaaacaaaa aaaatcatga    8160
aatcgatccc gtctgcggaa cggctagagc catcccagga ttccccaaag agaaacactg    8220
gcaagttagc aatcagaacg tgtctgacgt acaggtcgca tccgtgtacg aacgctagca    8280
gcacggatct aacacaaaca cggatctaac acaaacatga acagaagtag aactaccggg    8340
ccctaaccat ggaccggaac gccgatctag agaaggtaga gaggggggg ggggaggac    8400 gagcggcgta ccttgaagcg gaggtgccga cgggtggatt tggggagat ctggttgtgt    8460
```

```
gtgtgtgcgc tccgaacaac acgaggttgg ggaaagaggg tgtggagggg gtgtctattt    8520
attacggcgg gcgaggaagg gaaagcgaag gagcggtggg aaaggaatcc cccgtagctg    8580
ccgtgccgtg agaggaggag gaggccgcct gccgtgccgg ctcacgtctg ccgctccgcc    8640
acgcaatttc tggatgccga cagcggagca agtccaacgg tggagcggaa ctctcgagag    8700
gggtccagag gcagcgacag agatgccgtg ccgtctgctt cgcttggccc gacgcgacgc    8760
tgctggttcg ctggttggtg tccgttagac tcgtcgacgg cgtttaacag gctggcatta    8820
tctactcgaa acaagaaaaa tgtttcctta gttttttttaa tttcttaaag ggtatttgtt    8880
taatttttag tcactttatt ttattctatt ttatatctaa attattaaat aaaaaaacta    8940
aaatagagtt ttagttttct taatttagag gctaaaatag aataaaatag atgtactaaa    9000
aaaattagtc tataaaaacc attaccccta aaccctaaat ggatgtacta ataaaatgga    9060
tgaagtatta tataggtgaa gctatttgca aaaaaaaagg agaacacatg cacactaaaa    9120
agataaaact gtagagtcct gttgtcaaaa tactcaattg tcctttagac catgtctaac    9180
tgttcattta tatgattctc taaaacactg atattattgt agtagtatag attatattat    9240
tcgtagagta aagtttaaat atatgtataa agatagataa actgcacttc aaacaagtgt    9300
gacaaaaaaa atatgtggta atttttttata acttagacat gcaatgctca ttatctctag    9360
agaggggcac gaccgggtca cgctgcactg cagaagcttg ctgagtggct ccttcaacgt    9420
tgcggttctg tcagttccaa acgtaaaacg gcttgtcccg cgtcatcggc gggggtcata    9480
acgtgactcc cttaattctc cgctcatgat cagattgtcg tttcccgcct tcagtttaaa    9540
cgagctctaa ctataacggt cctaaggtag cgagcgatcg cctgcagtgc agcgtgaccc    9600
ggtcgtgccc ctctctagag ataatgagca ttgcatgtct aagttataaa aaattaccac    9660
atatttttt tgtcacactt gtttgaagtg cagtttatct atctttatac atatatttaa    9720
actttactct acgaataata taatctatac tactacaata atatcagtgt tttagagaat    9780
catataaatg aacagttaga catggtctaa aggacaattg agtattttga caacaggact    9840
ctacagtttt atcttttttag tgtgcatgtg ttctcctttt tttttgcaaa tagcttcacc    9900
tatataatac ttcatccatt ttattagtac atccatttag ggtttagggt taatggtttt    9960
tatagactaa tttttttagt acatctattt tattctattt tagcctctaa attaagaaaa    10020
ctaaaactct attttagttt tttttatttaa taatttagat ataaaataga ataaaataaa    10080
gtgactaaaa attaaacaaa tacccttttaa gaaattaaaa aaactaagga aacattttttc    10140
ttgtttcgag tagataatgc cagcctgtta aacgccgtcg acgagtctaa cggacaccaa    10200
ccagcgaacc agcagcgtcg cgtcgggcca agcgaagcag acggcacggc atctctgtcg    10260
ctgcctctgg acccctctcg agagttccgc tccaccgttg gacttgctcc gctgtcggca    10320
tccagaaatt gcgtggcgga gcggcagacg tgagccggca cggcaggcgg cctcctcctc    10380
ctctcacggc acggcagcta cggggggattc ctttcccacc gctccttcgc tttcccttcc    10440
tcgcccgccg taataaatag acacccccctc cacaccctct ttccccaacc tcgtgttgtt    10500
cggagcgcac acacacacaa ccagatctcc cccaaatcca cccgtcggca cctccgcttc    10560
aaggtacgcc gctcgtcctc ccccccccccc cctctctacc ttctctagat cggcgttccg    10620
gtccatggtt agggcccggt agttctactt ctgttcatgt ttgtgttaga tccgtgtttg    10680
tgttagatcc gtgctgctag cgttcgtaca cggatgcgac ctgtacgtca gacacgttct    10740
gattgctaac ttgccagtgt ttctctttgg ggaatcctgg gatggctcta gccgttccgc    10800
```

```
agacgggatc gatttcatga ttttttttgt ttcgttgcat agggtttggt ttgcccttt      10860
cctttatttc aatatatgcc gtgcacttgt ttgtcgggtc atctttttcat gctttttttt    10920
gtcttggttg tgatgatgtg gtctggttgg gcggtcgttc tagatcggag tagaattctg    10980
tttcaaacta cctggtggat ttattaattt tggatctgta tgtgtgtgcc atacatattc    11040
atagttacga attgaagatg atggatggaa atatcgatct aggataggta tacatgttga    11100
tgcgggtttt actgatgcat atacagagat gcttttttgtt cgcttggttg tgatgatgtg    11160
gtgtggttgg gcggtcgttc attcgttcta gatcggagta gaatactgtt tcaaactacc    11220
tggtgtattt attaattttg gaactgtatg tgtgtgtcat acatcttcat agttacgagt    11280
ttaagatgga tggaaatatc gatctaggat aggtatacat gttgatgtgg gttttactga    11340
tgcatataca tgatggcata tgcagcatct attcatatgc tctaaccttg agtacctatc    11400
tattataata aacaagtatg ttttataatt attttgatct tgatatactt ggatgatggc    11460
atatgcagca gctatatgtg gattttttta gccctgcctt catacgctat ttatttgctt    11520
ggtactgttt cttttgtcga tgctcaccct gttgtttggt gttacttctg caggtttaaa    11580
catggtgagc aagggcgagg agctgttcac cggggtggtg cccatcctgg tcgagctgga    11640
cggcgacgta aacggccaca agttcagcgt gtccggcgag ggcgagggcg atgccaccta    11700
cggcaagctg accctgaagt tcatctgcac caccggcaag ctgcccgtgc cctggcccac    11760
cctcgtgacc accctgacct acggcgtgca gtgcttcagc cgctacccccg accacatgaa    11820
gcagcacgac ttcttcaagt ccgccatgcc cgaaggctac gtccaggagc gcaccatctt    11880
cttcaaggac gacggcaact acaagacccg cgccgaggtg aagttcgagg gcgacaccct    11940
ggtgaaccgc atcgagctga agggcatcga cttcaaggag gacggcaaca tcctggggca    12000
caagctggag tacaactaca acagccacaa cgtctatatc atggccgaca agcagaagaa    12060
cggcatcaag gtgaacttca gatccgcca caacatcgag gacggcagcg tgcagctcgc    12120
cgaccactac cagcagaaca cccccatcgg cgacggcccc gtgctgctgc ccgacaacca    12180
ctacctgagc acccagtccg ccctgagcaa agaccccaac gagaagcgcg atcacatggt    12240
cctgctggag ttcgtgaccg ccgccgggat cactctcggc atggacgagc tgtacaagta    12300
acggaccggt catgggtcgt ttaagctgcc gatgtgcctg cgtcgtctgg tgccctctct    12360
ccatatggag gttgtcaaag tatctgctgt tcgtgtcatg agtcgtgtca gtgttggttt    12420
aataatggac cggttgtgtt gtgtgtgcgt actacccaga actatgacaa atcatgaata    12480
agtttgatgt ttgaaattaa agcctgtgct cattatgttc tgtcttttcag ttgtctccta    12540
atatttgcct gcaggtactg gctatctacc gtttcttact taggaggtgt ttgaatgcac    12600
taaaactaat agttagtggc taaaattagt taaaacatcc aaacaccata gctaatagtt    12660
gaactattag ctattttttgg aaaattagtt aatagtgagg tagttatttg ttagctagct    12720
aattcaacta acaattttta gccaactaac aattagtttc agtgcattca aacaccccct    12780
taatgttaac gtggttctat ctaccgtctc taatatatg gttgattgtt cggtttgttg    12840
ctatgctatt gggttctgat tgctgctagt tcttgctgaa tccagaagtt ctcgtagtat    12900
agctcagatt catattattt atttgagtga tggcgcgccc gagtatcgaa ttcctgcagg    12960
catgcaagcg atccccgatc gttcaaacat ttggcaataa agtttcttaa gattgaatcc    13020
tgttgccggt cttgcgatga ttatcatata atttctgttg aattacgtta agcatgtaat    13080
aattaacatg taatgcatga cgttatttat gagatgggtt tttatgatta gagtcccgca    13140
attatacatt taatacgcga tagaaaacaa aatatagcgc gcaaactagg ataaattatc    13200
```

-continued gcgcgcggtg tcatctatgt tactagatcg gcggccgcat taccctg                  13247

<210> SEQ ID NO 11
<211> LENGTH: 13728
<212> TYPE: DNA
<213> ORGANISM: artificial
<220> FEATURE:
<223> OTHER INFORMATION: synthetic vector sequence
<220> FEATURE:
<221> NAME/KEY: misc_feature
<222> LOCATION: (1)..(13728)
<223> OTHER INFORMATION: 130836 plant transformation vector

<400> SEQUENCE: 11
gagctctaac tataacggtc ctaaggtagc gagcgatcgc ctgcagtgca gcgtgacccg      60
gtcgtgcccc tctctagaga taatgagcat tgcatgtcta agttataaaa aattaccaca    120
tatttttttt gtcacacttg tttgaagtgc agtttatcta tctttataca tatatttaaa    180
ctttactcta cgaataatat aatctatact actacaataa tatcagtgtt ttagagaatc    240
atataaatga acagttagac atggtctaaa ggacaattga gtattttgac aacaggactc    300
tacagtttta tcttttagt gtgcatgtgt tctccttttt ttttgcaaat agcttcacct    360
atataatact tcatccattt tattagtaca tccatttagg gtttagggtt aatggttttt    420
atagactaat ttttttagta catctatttt attctatttt agcctctaaa ttaagaaaac    480
taaaactcta ttttagtttt tttatttaat aatttagata taaaatagaa taaaataaag    540
tgactaaaaa ttaaacaaat accctttaag aaattaaaaa aactaaggaa acattttttct   600
tgtttcgagt agataatgcc agcctgttaa acgccgtcga cgagtctaac ggacaccaac    660
cagcgaacca gcagcgtcgc gtcgggccaa gcgaagcaga cggcacggca tctctgtcgc    720
tgcctctgga cccctctcga gagttccgct ccaccgttgg acttgctccg ctgtcggcat    780
ccagaaattg cgtggcggag cggcagacgt gagccggcac ggcaggcggc ctcctcctcc    840
tctcacggca cggcagctac gggggattcc tttcccaccg ctccttcgct ttcccttcct    900
cgcccgccgt aataaataga caccccctcc acaccctctt tccccaacct cgtgttgttc    960
ggagcgcaca cacacacaac cagatctccc ccaaatccac ccgtcggcac ctccgcttca   1020
aggtacgccg ctcgtcctcc ccccccccc ctctctacct tctctagatc ggcgttccgg   1080
tccatggtta gggcccggta gttctacttc tgttcatgtt tgtgttagat ccgtgtttgt   1140
gttagatccg tgctgctagc gttcgtacac ggatgcgacc tgtacgtcag acacgttctg   1200
attgctaact tgccagtgtt tctctttggg gaatcctggg atggctctag ccgttccgca   1260
gacgggatcg atttcatgat tttttttgtt tcgttgcata gggtttggtt tgcccttttc    1320
ctttatttca atatatgccg tgcacttgtt tgtcgggtca tcttttcatg cttttttttg   1380
tcttggttgt gatgatgtgg tctggttggg cggtcgttct agatcggagt agaattctgt   1440
ttcaaactac ctggtggatt tattaatttt ggatctgtat gtgtgtgcca tacatattca   1500
tagttacgaa ttgaagatga tggatggaaa tatcgatcta ggataggtat acatgttgat   1560
gcgggtttta ctgatgcata tacagagatg cttttttgttc gcttggttgt gatgatgtgg   1620
tgtggttggg cggtcgttca ttcgttctag atcggagtag aatactgttt caaactacct   1680
ggtgtattta ttaattttgg aactgtatgt gtgtgtcata catcttcata gttacgagtt   1740
taagatggat ggaaatatcg atctaggata ggtacatg ttgatgtggg ttttactgat   1800
gcatatacat gatggcatat gcagcatcta ttcatatgct ctaaccttga gtacctatct   1860

```
attataataa acaagtatgt tttataatta ttttgatctt gatatacttg gatgatggca    1920
tatgcagcag ctatatgtgg attttttag ccctgccttc atacgctatt tatttgcttg    1980
gtactgtttc ttttgtcgat gctcaccctg ttgtttggtg ttacttctgc aggtttaaac    2040
atggtgagca agggcgagga gctgttcacc ggggtggtgc ccatcctggt cgagctggac    2100
ggcgacgtaa acggccacaa gttcagcgtg tccggcgagg gcgagggcga tgccacctac    2160
ggcaagctga ccctgaagtt catctgcacc accggcaagc tgcccgtgcc ctggcccacc    2220
ctcgtgacca ccctgaccta cggcgtgcag tgcttcagcc gctaccccga ccacatgaag    2280
cagcacgact tcttcaagtc cgccatgccc gaaggctacg tccaggagcg caccatcttc    2340
ttcaaggacg acggcaacta caagacccgc gccgaggtga agttcgaggg cgacaccctg    2400
gtgaaccgca tcgagctgaa gggcatcgac ttcaaggagg acggcaacat cctggggcac    2460
aagctggagt acaactacaa cagccacaac gtctatatca tggccgacaa gcagaagaac    2520
ggcatcaagg tgaacttcaa gatccgccac aacatcgagg acggcagcgt gcagctcgcc    2580
gaccactacc agcagaacac ccccatcggc gacggccccg tgctgctgcc cgacaaccac    2640
tacctgagca cccagtccgc cctgagcaaa gaccccaacg agaagcgcga tcacatggtc    2700
ctgctggagt tcgtgaccgc cgccgggatc actctcggca tggacgagct gtacaagtaa    2760
cggaccggtc atgggtcgtt taagctgccg atgtgcctgc gtcgtctggt gccctctctc    2820
catatggagg ttgtcaaagt atctgctgtt cgtgtcatga gtcgtgtcag tgttggttta    2880
ataatggacc ggttgtgttg tgtgtgcgta ctacccagaa ctatgacaaa tcatgaataa    2940
gtttgatgtt tgaaattaaa gcctgtgctc attatgttct gtctttcagt tgtctcctaa    3000
tatttgcctg caggtactgg ctatctaccg tttcttactt aggaggtgtt tgaatgcact    3060
aaaactaata gttagtggct aaaattagtt aaaacatcca acaccatag ctaatagttg    3120
aactattagc tattttttgga aaattagtta atagtgaggt agttatttgt tagctagcta    3180
attcaactaa caattttag ccaactaaca attagtttca gtgcattcaa acaccccctt    3240
aatgttaacg tggttctatc taccgtctcc taatatatgg ttgattgttc ggtttgttgc    3300
tatgctattg ggttctgatt gctgctagtt cttgctgaat ccagaagttc tcgtagtata    3360
gctcagattc atattattta tttgagtgat ggcgcgcccg agtatcgaat tcctgcaggc    3420
atgcaagcga tccccgatcg ttcaaacatt tggcaataaa gtttcttaag attgaatcct    3480
gttgccggtc ttgcgatgat tatcatataa tttctgttga attacgttaa gcatgtaata    3540
attaacatgt aatgcatgac gttatttatg agatgggttt ttatgattag agtcccgcaa    3600
ttatacattt aatacgcgat agaaaacaaa atatagcgcg caaactagga taaattatcg    3660
cgcgcggtgt catctatgtt actagatcgg cggccgcatt accctgttat ccctactttc    3720
ggattataac atcacatcta tgtcgggtgc ggagaaagag gtaatgaaat ggcatgacga    3780
tcaaccatac cagataacta tgactctctt aaggtagcca ataataccc ggtctgaacg    3840
aggtggcaaa cagctattat gggtattatg ggtggtaccc ggggatcctc tagagtcgac    3900
ctgcaggcat gcaagcttgg cactggccgt cgttttacaa cgtcgtgact gggaaaaccc    3960
tggcgttacc caacttaatc gccttgcagc acatccccct ttcgccagct ggcgtaatag    4020
cgaagaggcc cgcaccgatc gcccttccca acagttgcgc agcctgaatg gcgaatgcta    4080
gagcagcttg agcttggatc agattgtcgt ttcccgcctt cagtttaaac tatcagtgtt    4140
tgacaggata tattggcggg taaacctaag agaaaagagc gtttattaga ataatcggat    4200
atttaaaagg gcgtgaaaag gtttatccgt tcgtccattt gtatgtgcat gccaaccaca    4260
```

```
gggttcccct cgggagtgct tggcattccg tgcgataatg acttctgttc aaccacccaa      4320
acgtcggaaa gcctgacgac ggagcagcat tccaaaaaga tcccttggct cgtctgggtc      4380
ggctagaagg tcgagtgggc tgctgtggct tgatccctca acgcggtcgc ggacgtagcg      4440
cagcgccgaa aaatcctcga tcgcaaatcc gacgctgtcg aaaagcgtga tctgcttgtc      4500
gctctttcgg ccgacgtcct ggccagtcat cacgcgccaa agttccgtca caggatgatc      4560
tggcgcgagt tgctggatct cgccttcaat ccgggtctgt ggcgggaact ccacgaaaat      4620
atccgaacgc agcaagatcg tcgaccaatt cttgaagacg aaagggcctc gtgatacgcc      4680
tatttttata ggttaatgtc atgataataa tggtttctta gacgtcaggt ggcacttttc      4740
ggggaaatgt gcgcggaacc cctatttgtt tattttccta aatacattca aatatgtatc      4800
cgctcatgag acaataaccc tgataaatgc ttcaataata ttgaaaaagg aagagtatga      4860
gtattcaaca tttccgtgtc gcccttattc cctttttgc ggcattttgc cttcctgttt      4920
ttgctcaccc agaaacgctg gtgaaagtaa aagatgctga agatcagttg ggtgcacgag      4980
tgggttacat cgaactggat ctcaacagcg gtaagatcct tgagagtttt cgccccgaag      5040
aacgttttcc aatgatgagc acttttaaag ttctgctatg tggcgcggta ttatcccgtg      5100
ttgacgccgg gcaagagcaa ctcggtcgcc gcatacacta ttctcagaat gacttggttg      5160
agtactcacc agtcacagaa aagcatctta cggatggcat gacagtaaga gaattatgca      5220
gtgctgccat aaccatgagt gataacactg cggccaactt acttctgaca acgatcggag      5280
gaccgaagga gctaaccgct tttttgcaca acatggggga tcatgtaact cgccttgatc      5340
gttgggaacc ggagctgaat gaagccatac caaacgacga gcgtgacacc acgatgcctg      5400 caggggggg ggggggggga catgaggttg ccccgtattc agtgtcgctg atttgtattg      5460
tctgaagttg ttttacgtt aagttgatgc agatcaatta atacgatacc tgcgtcataa      5520
ttgattattt gacgtggttt gatggcctcc acgcacgttg tgatatgtag atgataatca      5580
ttatcacttt acgggtcctt tccggtgatc cgacaggtta cggggcggcg acctcgcggg      5640
ttttcgctat ttatgaaaat tttccggttt aaggcgtttc cgttcttctt cgtcataact      5700
taatgttttt atttaaaata ccctctgaaa agaaaggaaa cgacaggtgc tgaaagcgag      5760
ctttttggcc tctgtcgttt cctttctctg tttttgtccg tggaatgaac aatggaaccc      5820
cccccccccc ccccctgcag caatggcaac aacgttgcgc aaactattaa ctggcgaact      5880
acttactcta gcttcccggc aacaattaat agactggatg gaggcggata agttgcagg      5940 accacttctg cgctcggccc ttccggctgg ctggtttatt gctgataaat ctggagccgg      6000
tgagcgtggg tctcgcggta tcattgcagc actggggcca gatggtaagc cctcccgtat      6060
cgtagttatc tacacgacgg ggagtcaggc aactatggat gaacgaaata gacagatcgc      6120
tgagataggt gcctcactga ttaagcattg gtaactgtca gaccaagttt actcatatat      6180
actttagatt gatttaaaac ttcatttta atttaaaagg atctaggtga agatcctttt      6240
tgataatctc atgaccaaaa tcccttaacg tgagttttcg ttccactgag cgtcagaccc      6300
cgtagaaaag atcaaaggat cttcttgaga tcctttttt ctgcgcgtaa tctgctgctt      6360
gcaaacaaaa aaaccaccgc taccagcggt ggtttgtttg ccggatcaag agctaccaac      6420 tcttttccg aaggtaactg gcttcagcag agcgcagata ccaaatactg tccttctagt      6480
gtagccgtag ttaggccacc acttcaagaa ctctgtagca ccgcctacat acctcgctct      6540
gctaatcctg ttaccagtgg ctgctgccag tggcgataag tcgtgtctta ccgggttgga      6600
```

| | |
|---|---|
| ctcaagacga tagttaccgg ataaggcgca gcggtcgggc tgaacggggg gttcgtgcac | 6660 |
| acagcccagc ttggagcgaa cgacctacac cgaactgaga tacctacagc gtgagctatg | 6720 |
| agaaagcgcc acgcttcccg aagggagaaa ggcggacagg tatccggtaa gcggcagggt | 6780 |
| cggaacagga gagcgcacga gggagcttcc aggggggaaac gcctggtatc tttatagtcc | 6840 |
| tgtcgggttt cgccacctct gacttgagcg tcgattttg tgatgctcgt caggggggcg | 6900 |
| gagcctatgg aaaaacgcca gcaacgcggc ctttttacgg ttcctggcct tttgctggcc | 6960 |
| ttttgctcac atgttctttc ctgcgttatc ccctgattct gtggataacc gtattaccgc | 7020 |
| ctttgagtga gctgataccg ctcgccgcag ccgaacgacc gagcgcagcg agtcagtgag | 7080 |
| cgaggaagcg gaagagcgcc tgatgcggta ttttctcctt acgcatctgt gcggtatttc | 7140 |
| acaccgcata tggtgcactc tcagtacaat ctgctctgat gccgcatagt taagccagta | 7200 |
| tacactccgc tatcgctacg tgactgggtc atggctgcgc cccgacaccc gccaacaccc | 7260 |
| gctgacgcgc cctgacgggc ttgtctgctc ccggcatccg cttacagaca agctgtgacc | 7320 |
| gtctccggga gctgcatgtg tcagaggttt tcaccgtcat caccgaaacg cgcgaggcag | 7380 |
| cagatccccc gatcaagtag atacactaca tatatctaca atagacatcg agccggaagg | 7440 |
| tgatgtttac tttcctgaaa tccccagcaa ttttaggcca gttttaccc aagacttcgc | 7500 |
| ctctaacata aattatagtt accaaatctg gcaaagggt taacaagtgg cagcaacgga | 7560 |
| ttcgcaaacc tgtcacgcct tttgtgccaa agccgcgcc aggtttgcga tccgctgtgc | 7620 |
| caggcgttag gcgtcatatg aagatttcgg tgatccctga gcaggtggcg gaaacattgg | 7680 |
| atgctgagaa ccatttcatt gttcgtgaag tgttcgatgt gcacctatcc gaccaaggct | 7740 |
| ttgaactatc taccagaagt gtgagcccct accggaagga ttacatctcg gatgatgact | 7800 |
| ctgatgaaga ctctgcttgc tatggcgcat tcatcgacca agagcttgtc gggaagattg | 7860 |
| aactcaactc aacatggaac gatctagcct ctatcgaaca cattgttgtg tcgcacacgc | 7920 |
| accgaggcaa aggagtcgcg cacagtctca tcgaatttgc gaaaaagtgg gcactaagca | 7980 |
| gacagctcct tggcatacga ttagagacac aaacgaacaa tgtacctgcc tgcaatttgt | 8040 |
| acgcaaaatg tggctttact ctcggcggca ttgacctgtt cacgtataaa actagacctc | 8100 |
| aagtctcgaa cgaaacagcg atgtactggt actggttctc gggagcacag gatgacgcct | 8160 |
| aacaattcat tcaagccgac accgcttcgc ggcgcggctt aattcaggag ttaaacatca | 8220 |
| tgagggaagc ggtgatcgcc gaagtatcga ctcaactatc agaggtagtt ggcgtcatcg | 8280 |
| agcgccatct cgaaccgacg ttgctggccg tacatttgta cggctccgca gtggatggcg | 8340 |
| gcctgaagcc acacagtgat attgatttgc tggttacggt gaccgtaagg cttgatgaaa | 8400 |
| caacgcggcg agctttgatc aacgaccttt tggaaacttc ggcttcccct ggagagagcg | 8460 |
| agattctccg cgctgtagaa gtcaccattg ttgtgcacga cgacatcatt ccgtggcgtt | 8520 |
| atccagctaa gcgcgaactg caatttggag aatggcagcg caatgacatt cttgcaggta | 8580 |
| tcttcgagcc agccacgatc gacattgatc tggctatctt gctgacaaaa gcaagagaac | 8640 |
| atagcgttgc cttggtaggt ccagcggcgg aggaactctt tgatccggtt cctgaacagg | 8700 |
| atctatttga ggcgctaaat gaaaccttaa cgctatggaa ctcgccgccc gactgggctg | 8760 |
| gcgatgagcg aaatgtagtg cttacgttgt cccgcatttg gtacagcgca gtaaccggca | 8820 |
| aaatcgcgcc gaaggatgtc gctgccgact gggcaatgga gcgcctgccg gcccagtatc | 8880 |
| agcccgtcat acttgaagct aggcaggctt atccttggaca agaagatcgc ttggcctcgc | 8940 |
| gcgcagatca gttggaagaa tttgttcact acgtgaaagg cgagatcacc aaggtagtcg | 9000 |

```
gcaaataatg tctaacaatt cgttcaagcc gacgccgctt cgcggcgcgg cttaactcaa   9060
gcgttagaga gctggggaag actatgcgcg atctgttgaa ggtggttcta agcctcgtac   9120
ttgcgatggc atcggggcag gcacttgctg acctgccaat tgttttagtg gatgaagctc   9180
gtcttcccta tgactactcc ccatccaact acgacatttc tccaagcaac tacgacaact   9240
ccataagcaa ttacgacaat agtccatcaa attacgacaa ctctgagagc aactacgata   9300
atagttcatc caattacgac aatagtcgca acggaaatcg taggcttata tatagcgcaa   9360
atgggtctcg cactttcgcc ggctactacg tcattgccaa caatgggaca acgaacttct   9420
tttccacatc tggcaaaagg atgttctaca ccccaaaagg ggggcgcggc gtctatggcg   9480
gcaaagatgg gagcttctgc ggggcattgg tcgtcataaa tggccaattt tcgcttgccc   9540
tgacagataa cggcctgaag atcatgtatc taagcaacta gcctgctctc taataaaatg   9600
ttaggcctca acatctagtc gcaagctgag gggaaccact agtgtcatac gaacctccaa   9660
gagacggtta cacaaacggg tacattgttg atgtcatgta tgacaatcgc ccaagtaagt   9720
atccagctgt gttcagaacg tacgtccgaa ttaattcatc ggggtacggt cgacgatcgt   9780
caacgttcac ttctaaagaa atagcgccac tcagcttcct cagcggcttt atccagcgat   9840
ttcctattat gtcggcatag ttctcaagat cgacagcctg tcacggttaa gcgagaaatg   9900
aataagaagg ctgataattc ggatctctgc gagggagatg atatttgatc acaggcagca   9960
acgctctgtc atcgttacaa tcaacatgct accctccgcg agatcatccg tgtttcaaac  10020
ccggcagctt agttgccgtt cttccgaata gcatcggtaa catgagcaaa gtctgccgcc  10080
ttacaacggc tctcccgctg acgccgtccc ggactgatgg gctgcctgta tcgagtggtg  10140
attttgtgcc gagctgccgg tcggggagct gttggctggc tggtggcagg atatattgtg  10200
gtgtaaacaa attgacgctt agacaactta ataacacatt gcggacgttt ttaatgtact  10260
gaattcccgg gacttccgat taagtagagc ttccctgcc gaagcgcgtg gagctacaac  10320
ccaaacctgc agctgaatta acgccgaatt aattcggggg atctggattt tagtactgga  10380
ttttggtttt aggaattaga aattttattg atagaagtat tttacaaata caaatacata  10440
ctaagggttt cttatatgct caacacatga gcgaaaccct ataggaaccc taattcccTT  10500
atctgggaac tactcacaca ttattatgga gaaactcgag tcagatctgt ctatttcttt  10560
gccctcggac gagtgctggg gcgtcggttt ccactatcgg cgagtacttc tacacagcca  10620
tcggtccaga cggccgcgct tctgcgggcg atttgtgtac gcccgacagt cccggctccg  10680
gatcggacga ttgcgtcgca tcgaccctgc gcccaagctg catcatcgaa attgccgtca  10740
accaagctct gatagagttg gtcaagacca atgcggagca tatacgcccg gagtcgtggc  10800
gatcctgcaa gctccggatg cctccgctcg aagtagcgcg tctgctgctc catacaagcc  10860
aaccacggcc tccagaagaa gatgttggcg acctcgtatt gggaatcccc gaacatcgcc  10920
tcgctccagt caatgaccgc tgttatgcgg ccattgtccg tcaggacatt gttggagccg  10980
aaatccgcgt gcacgaggtg ccggacttcg gggcagtcct cggcccaaag catcagctca  11040
tcgagagcct gcgcgacgga cgcactgacg gtgtcgtcca tcacagtttg ccagtgatac  11100
acatggggat cagcaatcgc gcatatgaaa tcacgccatg tagtgtattg accgattcct  11160
tgcggtccga atgggccgaa cccgctcgtc tggctaagat cggccgcagc gatcgcatcc  11220
atagcctccg cgaccggttg tagaacagcg ggcagttcgg tttcaggcag gtcttgcaac  11280
gtgacaccct gtgcacggcg ggagatgcaa taggtcaggc tctcgctaaa ctccccaatg  11340
```

```
tcaagcactt ccggaatcgg gagcgcggcc gatgcaaagt gccgataaac ataacgatct   11400
ttgtagaaac catcggcgca gctatttacc cgcaggacat atccacgccc tcctacatcg   11460
aagctgaaag cacgagattc ttcgccctcc gagagctgca tcaggtcgga gacgctgtcg   11520 aactttcga tcagaaactt ctcgacagac gtcgcggtga gttcaggctt tttcatatct   11580
cattctacct gcagaagtaa caccaaacaa cagggtgagc atcgacaaaa gaaacagtac   11640
caagcaaata aatagcgtat gaaggcaggg ctaaaaaaat ccacatatag ctgctgcata   11700
tgccatcatc caagtatatc aagatcaaaa taattataaa acatacttgt ttattataat   11760
agataggtac tcaaggttag agcatatgaa tagatgctgc atatgccatc atgtatatgc   11820
atcagtaaaa cccacatcaa catgtatacc tatcctagat cgatatttcc atccatctta   11880
aactcgtaac tatgaagatg tatgacacac atacagtt ccaaaattaa taaatacacc   11940
aggtagtttg aaacagtatt ctactccgat ctagaacgaa tgaacgaccg cccaaccaca   12000
ccacatcatc acaaccaagc gaacaaaaag catctctgta tatgcatcag taaaacccgc   12060
atcaacatgt atacctatcc tagatcgata tttccatcca tcatcttcaa ttcgtaacta   12120
tgaatatgta tggcacacac atacagatcc aaaattaata aatccaccag gtagtttgaa   12180
acagaattct actccgatct agaacgaccg cccaaccaga ccacatcatc acaaccaaga   12240 caaaaaaag catgaaaaga tgacccgaca aacaagtgca cggcatatat tgaaataaag   12300
gaaaagggca aaccaaaccc tatgcaacga aacaaaaaaa atcatgaaat cgatcccgtc   12360
tgcggaacgg ctagagccat cccaggattc cccaaagaga aacactggca agttagcaat   12420
cagaacgtgt ctgacgtaca ggtcgcatcc gtgtacgaac gctagcagca cggatctaac   12480
acaaacacgg atctaacaca aacatgaaca gaagtagaac taccgggccc taaccatgga   12540
ccggaacgcc gatctagaga aggtagagag ggggggggg ggaggacgag cggcgtacct   12600
tgaagcggag gtgccgacgg gtggatttgg gggagatctg gttgtgtgtg tgtgcgctcc   12660
gaacaacacg aggttgggga aagagggtgt ggaggggtg tctatttatt acggcgggcg   12720
aggaagggaa agcgaaggag cggtgggaaa ggaatccccc gtagctgccg tgccgtgaga   12780
ggaggaggag gccgcctgcc gtgccggctc acgtctgccg ctccgccacg caatttctgg   12840
atgccgacag cggagcaagt ccaacggtgg agcggaactc tcgagagggg tccagaggca   12900
gcgacagaga tgccgtgccg tctgcttcgc ttggcccgac gcgacgctgc tggttcgctg   12960
gttggtgtcc gttagactcg tcgacggcgt ttaacaggct ggcattatct actcgaaaca   13020
agaaaaatgt ttccttagtt ttttaattt cttaaagggt atttgtttaa tttttagtca   13080
ctttatttta ttctatttta tatctaaatt attaaataaa aaaactaaaa tagagttta   13140 gttttcttaa tttagaggct aaaatagaat aaaatagatg tactaaaaaa attagtctat   13200
aaaaaccatt aaccctaaac cctaaatgga tgtactaata aaatggatga agtattatat   13260
aggtgaagct atttgcaaaa aaaaaggaga acacatgcac actaaaaaga taaaactgta   13320
gagtcctgtt gtcaaaatac tcaattgtcc tttagaccat gtctaactgt tcatttatat   13380
gattctctaa aacactgata ttattgtagt agtatagatt atattattcg tagagtaaag   13440
tttaaatata tgtataaaga tagataaact gcacttcaaa caagtgtgac aaaaaaaata   13500
tgtggtaatt ttttataact tagacatgca atgctcatta tctctagaga ggggcacgac   13560
cgggtcacgc tgcactgcag aagcttgctg agtggctcct tcaacgttgc ggttctgtca   13620
gttccaaacg taaacggct tgtcccgcgt catcggcggg ggtcataacg tgactcccctt   13680 aattctccgc tcatgatcag attgtcgttt cccgccttca gtttaaac   13728
```

<210> SEQ ID NO 12
<211> LENGTH: 12103
<212> TYPE: DNA
<213> ORGANISM: Artificial
<220> FEATURE:
<223> OTHER INFORMATION: synthetic vector sequence
<220> FEATURE:
<221> NAME/KEY: misc_feature
<222> LOCATION: (1)..(12103)
<223> OTHER INFORMATION: 133337 vector

<400> SEQUENCE: 12

```
catgccaacc acagggttcc cctcgggatc aaagtacttt gatccaaccc ctccgctgct     60
atagtgcagt cggcttctga cgttcagtgc agccgtcttc tgaaaacgac atgtcgcaca    120
agtcctaagt tacgcgacag gctgccgccc tgccttttc ctggcgtttt cttgtcgcgt    180
gttttagtcg cataaagtag aatacttgcg actagaaccg agacattac gccatgaaca    240
agagcgccgc cgctggcctg ctgggctatg cccgcgtcag caccgacgac caggacttga    300
ccaaccaacg ggccgaactg cacgcggccg gctgcaccaa gctgttttcc gagaagatca    360
ccggcaccag gcgcgaccgc ccggagctgg ccaggatgct tgaccaccta cgccctggcg    420
acgttgtgac agtgaccagg ctagaccgcc tggcccgcag cacccgcgac ctactggaca    480
ttgccgagcg catccaggag gccgcgcgg gcctgcgtag cctggcagag ccgtgggccg    540
acaccaccac gccggccggc cgcatggtgt tgaccgtgtt cgccggcatt gccgagttcg    600
agcgttccct aatcatcgac cgcacccgga gcgggcgcga ggccgccaag gcccgaggcg    660
tgaagtttgg ccccgccct accctcaccc cggcacagat cgcgcacgcc cgcgagctga    720
tcgaccagga aggccgcacc gtgaaagagg cggctgcact gcttggcgtg catcgctcga    780
ccctgtaccg cgcacttgag cgcagcgagg aagtgacgcc caccgaggcc aggcggcgcg    840
gtgccttccg tgaggacgca ttgaccgagg ccgacgccct ggcggccgcc gagaatgaac    900
gccaagagga caagcatga accgcacca ggacggccag gacgaaccgt ttttcattac    960
cgaagagatc gaggcggaga tgatcgcggc cgggtacgtg ttcgagccgc ccgcgcacgt   1020
ctcaaccgtg cggctgcatg aaatcctggc cggtttgtct gatgccaagc tggcggcctg   1080
gccggccagc ttggccgctg aagaaaccga gcgccgccgt ctaaaaaggt gatgtgtatt   1140
tgagtaaaac agcttgcgtc atgcggtcgc tgcgtatatg atgcgatgag taaataaaca   1200
aatacgcaag gggaacgcat gaaggttatc gctgtactta accagaaagg cgggtcaggc   1260
aagacgacca tcgcaaccca tctagcccgc gccctgcaac tcgccggggc cgatgttctg   1320
ttagtcgatt ccgatcccca gggcagtgcc cgcgattggg cggccgtgcg gaagatcaa   1380
ccgctaaccg ttgtcggcat cgaccgcccg acgattgacc gcgacgtgaa ggccatcggc   1440
cggcgcgact tcgtagtgat cgacggagcg ccccaggcgg cggacttggc tgtgtccgcg   1500
atcaaggcag ccgacttcgt gctgattccg gtgcagccaa gcccttacga catatgggcc   1560
accgccgacc tggtggagct ggttaagcag cgcattgagg tcacggatgg aaggctacaa   1620
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
```

```
gcaaggctgc aacgttggcc agcctggcag acacgccagc catgaagcgg gtcaactttc    1980
agttgccggc ggaggatcac accaagctga agatgtacgc ggtacgccaa ggcaagacca    2040
ttaccgagct gctatctgaa tacatcgcgc agctaccaga gtaaatgagc aaatgaataa    2100
atgagtagat gaattttagc ggctaaagga ggcggcatgg aaaatcaaga acaaccaggc    2160
accgacgccg tggaatgccc catgtgtgga ggaacgggcg gttggccagg cgtaagcggc    2220
tgggttgtct gccggccctg caatggcact ggaaccccca agcccgagga atcgcgtga     2280
cggtcgcaaa ccatccggcc cggtacaaat cggcgcggcg ctgggtgatg acctggtgga    2340
gaagttgaag gccgcgcagg ccgcccagcg gcaacgcatc gaggcagaag cacgccccgg    2400
tgaatcgtgg caagcggccg ctgatcgaat ccgcaaagaa tcccggcaac cgccggcagc    2460
cggtgcgccg tcgattagga agccgcccaa gggcgacgag caaccagatt ttttcgttcc    2520
gatgctctat gacgtgggca cccgcgatag tcgcagcatc atggacgtgg ccgttttccg    2580
tctgtcgaag cgtgaccgac gagctggcga ggtgatccgc tacgagcttc agacgggca    2640
cgtagaggtt tccgcagggc cggccggcat ggccagtgtg tgggattacg acctggtact    2700
gatggcggtt tcccatctaa ccgaatccat gaaccgatac cgggaaggga agggagacaa    2760
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccgagggtga    2940
agccttgatt agccgctaca agatcgtaaa gagcgaaacc gggcggccgg agtacatcga    3000
gatcgagcta gctgattgga tgtaccgcga gatcacagaa ggcaagaacc cggacgtgct    3060
gacggttcac cccgattact ttttgatcga tcccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240
aaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaaggtcga aaaggtctct ttcctgtgga    3420
tagcacgtac attgggaacc caaagccgta cattgggaac cggaacccgt acattgggaa    3480
cccaaagccg tacattggga accggtcaca catgtaagtg actgatataa agagaaaaa    3540
aggcgatttt tccgcctaaa actctttaaa acttattaaa actcttaaaa cccgcctggc    3600
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accaggcgc ggacaagccg cgccgtcgcc     3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca agcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
```

```
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt ttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaaatata    4980
atattttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat ctttcacaaa    5160
gatgttgctg tctcccaggt cgccgtggga aaagacaagt tcctcttcgg cttttccgt    5220
ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct tgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtcctttt cccgttccac    5580
atcataggtg gtcccttat accggctgtc cgtcattttt aaatataggt tttcattttc    5640
tcccaccagc ttatatacct tagcaggaga cattccttcc gtatctttta cgcagcggta    5700
ttttcgatc agttttttca attccggtga tattctcatt ttagccattt attatttcct    5760
tcctcttttc tacagtattt aaagataccc caagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctg ttggctggct ggtgacagga    6180
tatattgttg tgttaacaaa ttgacgctta gacaacttaa taacacattg cggacgtttt    6240
taatgtagat ctagtaacat agatgacacc gcgcgcgata atttatccta gtttgcgcgc    6300
tatattttgt tttctatcgc gtattaaatg tataattgcg ggactctaat cataaaaacc    6360
catctcataa ataacgtcat gcattacatg ttaattatta catgcttaac gtaattcaac    6420
agaaattata tgataatcat cgcaagaccg gcaacaggat tcaatcttaa gaaactttat    6480
tgccaaatgt ttgaacgatc tcgactctag ctagaggatc gatccgaacc ccagagtccc    6540
gctcatcagg cagccttcgt atcggagagt tcgatcttcg cgcccagccc ggccatcagg    6600
tccatgaact ccgggaagct cgtggcgatc atcgtggcat cgtccaccgt gacagggttt    6660
```

```
tccgacacga ggcccatgac gaggaagctc atggcgatgc ggtgatcgag atgggtggcg    6720
acggcggcgc ccgaggcgtt gccgagcccc ttgccgtcag gcggccgcg cacgacgagc     6780 gacgtctcgc cctcatcgca atccacgcca ttgagcttga ggccattggc gacggccgag    6840
aggcggtcgc tttccttgac gcggagttct tccagaccgt tcatcacggt cgccccttcc    6900
gcgaaggcgg cggcgacagc gagaatcgga tattcgtcga tcatcgaagg cgcgcggtct    6960
tccggcaccg tgacgccctt cagcgtggag gagcgaacgc gcaggtccgc cacgtcttcg    7020
ccgccggcaa ggcgcgggtt gatgacttcg atgtcggcgc ccatttcctg cagcgtcagg    7080
atgaggccgg tgcgggtggg gttcatcagc acgttgagga tggtgacgtc ggagcccgga    7140
acaagcaggg ccgcaaccag cgggaaggcc gtcgaggacg ggtcgcccgg cacgtcgatg    7200
acttggccgg tgagcttgcc gcggccttcc aggcggatgg tgcgcacgcc gtccgcatcc    7260
gtctcgacgg taaggttggc gccaaagccc tgcagcatct tttccgtatg atcgcgcgtc    7320
atgatcggct cgatgaccgt cgtgatgccg ggcgtgttga ggccggcgag cagcacggcg    7380
gacttcacct gtgcggaggc catcggcacg cggtaggtga tcggcgtcgg cgtcttcggc    7440
ccgcgcaagg taacgggaag acggtcaccg tcttccgatt tcacctgcac gcccatttcg    7500
cgcagcgggt tcaacacgcg gcccatcggg cgctttgtga gcgaggcgtc gccgatgaag    7560
gtgctgtcga aatcgtagac cccgacgagg cccatggtca gcggcagcc cgtggcggca     7620 ttgccgaaat cgagcggcgc ctcaggcgcc aggaggccgc cattgccgac gccatcgatg    7680
atccaggtgt cgccttcctt acggatcctg gcgcccatgg cctgcatggc cttgcccgta    7740
ttgatgacgt cctcgccttc cagaaggccg gtgatgcgcg tttcaccgct cgcgagaccg    7800
ccgaacatga aggaccggtg ggagatcgac ttgtcgccgg gaatgcggac ggttccggaa    7860
aggccagagg atttgcgggc ggttgcgggc cggctgcttg caccgtgaag catgcacgcc    7920
gtggaaacag aagacatgac cttaagagga cgaagctcag agccaattaa cgtcatccca    7980
ctcttcttca atccccacga cgacgaaatc ggataagctc gtggatgctg ctgcgtcttc    8040
agagaaaccg ataagggaga tttgcgttga ctggatttcg agagattgga gataagagat    8100
gggttctgca caccattgca gattctgcta acttgcgcca tggtcgatcg acagatctgc    8160
gaaagctcga gctgttaatc agaaaaactc agattaatcg acaaattcga tcgcacaaac    8220
tagaaactaa caccagatct agatagaaat cacaaatcga agagtaatta ttcgacaaaa    8280
ctcaaattat ttgaacaaat cggatgatat ctatgaaacc ctaatcgaga attaagatga    8340
tatctaacga tcaaacccag aaaatcgtct tcgatctaag attaacagaa tctaaaccaa    8400
agaacatata cgaaattggg atcgaacgaa aacaaaatcg aagattttga gagaataagg    8460
aacacagaaa tttaccttga tcacggtaga gagaattgag agaaagtttt taagattttg    8520
agaaattgaa atctgaattg tgaagaagaa gagctctttg ggtattgttt tatagaagaa    8580
gaagaagaaa agacgaggac gactaggtca cgagaaagct aaggcggtga agcaatagct    8640
aataataaaa tgacacgtgt attgagcgtt gtttacacgc aaagttgttt ttggctaatt    8700
gccttatttt taggttgagg aaaagtattt gtgctttgag ttgataaaca cgactcgtgt    8760
gtgccggctg caaccacttt gacgccgttt attactgact cgtcgacaac cacaatttct    8820
aacggtcgtc ataagatcca gccgttgaga tttaacgatc gttacgattt atattttttt    8880
agcattatcg tttatttttt taaatatacg gtggagctga aaattggcaa taattgaacc    8940
gtgggtccca ctgcattgaa gcgtatttcg tattttctag aattcttcgt gctttatttc    9000
ttttcctttt tgttttttttt tgccatttat ctaatgcaag tgggcttata aaatcagtga   9060
```

```
atttcttgga aaagtaactt ctttatcgta taacatattg tgaaattatc catttctttt   9120
aattttttag tgttattgga tatttttgta tgattattga tttgcatagg ataatgactt   9180
ttgtatcaag ttggtgaaca agtctcgtta aaaaaggcaa gtggtttggt gactcgattt   9240
attcttgtta tttaattcat atatcaatgg atcttatttg gggcctggtc catatttaac   9300
actcgtgttc agtccaatga ccaataatat tttttcatta ataacaatgt aacaagaatg   9360
atacacaaaa cattctttga ataagttcgc tatgaagaag ggaacttatc cggtcctaga   9420
tcatcagttc atacaaacct ccatagagtt caacatctta aacaagaata tcctgattgc   9480
tccaccatgt tggcaagctg ctctagccaa tacgcaaacc gcctctcccc gcgcgttggc   9540
cgattcatta atgcagctgg cacgacaggt ttcccgactg gaaagcgggc agtgagcgca   9600
acgcaattaa tgtgagttag ctcactcatt aggcacccca ggctttacac tttatgcttc   9660
cggctcgtat gttgtgtgga attgtgagcg ataacaatt tcacacagga acagctatg    9720 accatgatta cgaattcgag ctctaactat aacggtccta aggtagcgag cgatcgcgcg   9780
tattggctag agcagcttgc caacatggtg gagcacgaca ctctcgtcta ctccaagaat   9840
atcaaagata cagtctcaga agaccaaagg gctattgaga cttttcaaca aagggtaata   9900
tcgggaaacc tcctcggatt ccattgccca gctatctgtc acttcatcaa aaggacagta   9960 gaaaggaag gtggcaccta caaatgccat cattgcgata aggaaaggc tatcgttcaa    10020 gatgcctctg ccgacagtgg tcccaaagat ggaccccac ccacgaggag catcgtggaa    10080
aaagaagacg ttccaaccac gtcttcaaag caagtggatt gatgtgaaca tggtggagca   10140
cgacactctc gtctactcca agaatatcaa agatacagtc tcagaagacc aaagggctat   10200
tgagactttt caacaaaggg taatatcggg aaacctcctc ggattccatt gcccagctat   10260
ctgtcacttc atcaaaagga cagtagaaaa ggaaggtggc acctacaaat gccatcattg   10320
cgataaagga aaggctatcg ttcaagatgc ctctgccgac agtggtccca agatggacc    10380 cccacccacg aggagcatcg tggaaaaaga agacgttcca accacgtctt caaagcaagt   10440
ggattgatgt gatatctcca ctgacgtaag ggatgacgca caatcccact atccttcgca   10500
agacccttcc tctatataag gaagttcatt tcatttggag aggacacgct gaaatcacca   10560
gtctctctct acaaatctat ctctgtttaa acatggtgag caagggcgag gagctgttca   10620
ccggggtggt gcccatcctg gtcgagctgg acggcgacgt aaacggccac aagttcagcg   10680
tgtccggcga gggcgagggc gatgccacct acggcaagct gaccctgaag ttcatctgca   10740
ccaccggcaa gctgcccgtg ccctggccca cctcgtgac caccctgacc tacggcgtgc    10800
agtgcttcag ccgctacccc gaccacatga gcagcacga cttcttcaag tccgccatgc    10860
ccgaaggcta cgtccaggag cgcaccatct tcttcaagga cgacggcaac tacaagaccc   10920
gcgccgaggt gaagttcgag ggcgacaccc tggtgaaccg catcgagctg aagggcatcg   10980
acttcaagga ggacggcaac atcctggggc acaagctgga gtacaactac aacagccaca   11040
acgtctatat catggccgac aagcagaaga acggcatcaa ggtgaacttc aagatccgcc   11100
acaacatcga ggacggcagc gtgcagctcg ccgaccacta ccagcagaac acccccatcg   11160
gcgacggccc cgtgctgctg cccgacaacc actacctgag cacccagtcc gccctgagca   11220
aagaccccaa cgagaagcgc gatcacatgg tcctgctgga gttcgtgacc gccgccggga   11280
tcactctcgg catggacgag ctgtacaagt ctgagaagga tgagctctga cggaccggat   11340
ctgtcgatcg acaagctcga gtttctccat aataatgtgt gagtagttcc cagataaggg   11400
```

```
aattagggtt cctatagggt ttcgctcatg tgttgagcat ataagaaacc cttagtatgt    11460
atttgtattt gtaaaatact tctatcaata aaatttctaa ttcctaaaac caaaatccag    11520
tactaaaatc cagatccccc gaattagcgg ccgcattacc ctgttatccc tactttcgga    11580
ttataacatc acatctatgt cggggtgcgga gaaagaggta atgaaatggc atgacgatca    11640
accataccag ataactatga ctctcttaag gtagccaaat aatacccggt ctgaacgagg    11700
tggcaaacag ctattatggg tattatgggt ggtacccggg gatcctctag agtcgacctg    11760
caggcatgca agcttggcac tggccgtcgt tttacaacgt cgtgactggg aaaaccctgg    11820
cgttacccaa cttaatcgcc ttgcagcaca tccccctttc gccagctggc gtaatagcga    11880
agaggcccgc accgatcgcc cttcccaaca gttgcgcagc ctgaatggcg aatgctagag    11940
cagcttgagc ttggatcaga ttgtcgtttc ccgccttcag tttaaactat cagtgtttga    12000
caggatatat tggcgggtaa acctaagaga aaagagcgtt tattagaata acggatattt    12060
aaaagggcgt gaaaggtttt atccgttcgt ccatttgtat gtg                      12103
```

<210> SEQ ID NO 13
<211> LENGTH: 1596
<212> TYPE: DNA
<213> ORGANISM: Agrobacterium sp.
<220> FEATURE:
<221> NAME/KEY: misc_feature
<222> LOCATION: (1)..(1596)
<223> OTHER INFORMATION: cp4 gene

<400> SEQUENCE: 13

```
atggcgcaag ttagcagaat ctgcaatggt gtgcagaacc catctcttat ctccaatctc      60
tcgaaatcca gtcaacgcaa atctcccttta tcggtttctc tgaagacgca gcagcatcca    120
cgagcttatc cgatttcgtc gtcgtggga ttgaagaaga gtgggatgac gttaattggc      180
tctgagcttc gtcctcttaa ggtcatgtct tctgtttcca cggcgtgcat gcttcacggt     240
gcaagcagcc ggcccgcaac cgcccgcaaa tcctctggcc tttccggaac cgtccgcatt     300
cccggcgaca gtcgatctc ccaccggtcc ttcatgttcg gcggtctcgc gagcggtgaa      360
acgcgcatca ccggccttct ggaaggcgag gacgtcatca atacgggcaa ggccatgcag    420
gccatgggcg ccaggatccg taaggaaggc gacacctgga tcatcgatgg cgtcggcaat    480
ggcggcctcc tggcgcctga ggcgccgctc gatttcggca atgccgccac gggctgccgc    540
ctgaccatgg gcctcgtcgg ggtctacgat ttcgacagca ccttcatcgg cgacgcctcg     600
ctcacaaagc gcccgatggg ccgcgtgttg aacccgctgc gcgaaatggg cgtgcaggtg    660
aaatcggaag acggtgaccg tcttcccgtt accttgcgcg ggccgaagac gccgacgccg     720
atcacctacc gcgtgccgat ggcctccgca caggtgaagt ccgccgtgct gctcgccggc    780
ctcaacacgc ccggcatcac gacggtcatc gagccgatca tgacgcgcga tcatacggaa    840
aagatgctgc agggctttgg cgccaacctt accgtcgaga cggatgcgga cggcgtgcgc    900
accatccgcc tggaaggccg cggcaagctc accggcaagt catcgacgt gccgggcgac    960 ccgtcctcga cggccttccc gctggttgcg gccctgcttg ttccgggctc cgacgtcacc    1020
atcctcaacg tgctgatgaa ccccacccgc accggcctca tcctgacgct gcaggaaatg    1080
ggcgccgaca tcgaagtcat caacccgcgc cttgccggcg gcgaagacgt ggcggacctg    1140
cgcgttcgct cctccacgct gaagggcgtc acggtgccgg aagaccgcgc gccttcgatg    1200
atcgacgaat atccgattct cgctgtcgcc gccgccttcg cggaagggc gaccgtgatg    1260 aacggtctgg aagaactccg cgtcaaggaa agcgaccgcc tctcggccgt cgccaatggc    1320
```

```
ctcaagctca atggcgtgga ttgcgatgag ggcgagacgt cgctcgtcgt gcgcggccgc    1380
cctgacggca aggggctcgg caacgcctcg ggcgccgccg tcgccaccca tctcgatcac    1440
cgcatcgcca tgagcttcct cgtcatgggc ctcgtgtcgg aaaaccctgt cacggtggac    1500
gatgccacga tgatcgccac gagcttcccg gagttcatgg acctgatggc cgggctgggc    1560
gcgaagatcg aactctccga tacgaaggct gcctga                              1596
```

<210> SEQ ID NO 14
<211> LENGTH: 531
<212> TYPE: PRT
<213> ORGANISM: Agrobacterium sp.
<220> FEATURE:
<221> NAME/KEY: MISC_FEATURE
<222> LOCATION: (1)..(531)
<223> OTHER INFORMATION: CP4 protein

<400> SEQUENCE: 14

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Leu His Gly
65                  70                  75                  80

Ala Ser Ser Arg Pro Ala Thr Ala Arg Lys Ser Ser Gly Leu Ser Gly
                85                  90                  95

Thr Val Arg Ile Pro Gly Asp Lys Ser Ile Ser His Arg Ser Phe Met
            100                 105                 110

Phe Gly Gly Leu Ala Ser Gly Glu Thr Arg Ile Thr Gly Leu Leu Glu
        115                 120                 125

Gly Glu Asp Val Ile Asn Thr Gly Lys Ala Met Gln Ala Met Gly Ala
    130                 135                 140

Arg Ile Arg Lys Glu Gly Asp Thr Trp Ile Ile Asp Gly Val Gly Asn
145                 150                 155                 160

Gly Gly Leu Leu Ala Pro Glu Ala Pro Leu Asp Phe Gly Asn Ala Ala
                165                 170                 175

Thr Gly Cys Arg Leu Thr Met Gly Leu Val Gly Val Tyr Asp Phe Asp
            180                 185                 190

Ser Thr Phe Ile Gly Asp Ala Ser Leu Thr Lys Arg Pro Met Gly Arg
        195                 200                 205

Val Leu Asn Pro Leu Arg Glu Met Gly Val Gln Val Lys Ser Glu Asp
    210                 215                 220

Gly Asp Arg Leu Pro Val Thr Leu Arg Gly Pro Lys Thr Pro Thr Pro
225                 230                 235                 240

Ile Thr Tyr Arg Val Pro Met Ala Ser Ala Gln Val Lys Ser Ala Val
                245                 250                 255

Leu Leu Ala Gly Leu Asn Thr Pro Gly Ile Thr Thr Val Ile Glu Pro
            260                 265                 270

Ile Met Thr Arg Asp His Thr Glu Lys Met Leu Gln Gly Phe Gly Ala
        275                 280                 285

Asn Leu Thr Val Glu Thr Asp Ala Asp Gly Val Arg Thr Ile Arg Leu
    290                 295                 300
```

Glu Gly Arg Gly Lys Leu Thr Gly Gln Val Ile Asp Val Pro Gly Asp
305                 310                 315                 320

Pro Ser Ser Thr Ala Phe Pro Leu Val Ala Ala Leu Leu Val Pro Gly
                325                 330                 335

Ser Asp Val Thr Ile Leu Asn Val Leu Met Asn Pro Thr Arg Thr Gly
            340                 345                 350

Leu Ile Leu Thr Leu Gln Glu Met Gly Ala Asp Ile Glu Val Ile Asn
        355                 360                 365

Pro Arg Leu Ala Gly Gly Glu Asp Val Ala Asp Leu Arg Val Arg Ser
    370                 375                 380

Ser Thr Leu Lys Gly Val Thr Val Pro Glu Asp Arg Ala Pro Ser Met
385                 390                 395                 400

Ile Asp Glu Tyr Pro Ile Leu Ala Val Ala Ala Phe Ala Glu Gly
                405                 410                 415

Ala Thr Val Met Asn Gly Leu Glu Glu Leu Arg Val Lys Glu Ser Asp
                420                 425                 430

Arg Leu Ser Ala Val Ala Asn Gly Leu Lys Leu Asn Gly Val Asp Cys
            435                 440                 445

Asp Glu Gly Glu Thr Ser Leu Val Val Arg Gly Arg Pro Asp Gly Lys
            450                 455                 460

Gly Leu Gly Asn Ala Ser Gly Ala Ala Val Ala Thr His Leu Asp His
465                 470                 475                 480

Arg Ile Ala Met Ser Phe Leu Val Met Gly Leu Val Ser Glu Asn Pro
                485                 490                 495

Val Thr Val Asp Asp Ala Thr Met Ile Ala Thr Ser Phe Pro Glu Phe
                500                 505                 510

Met Asp Leu Met Ala Gly Leu Gly Ala Lys Ile Glu Leu Ser Asp Thr
            515                 520                 525

Lys Ala Ala
    530

<210> SEQ ID NO 15
<211> LENGTH: 738
<212> TYPE: DNA
<213> ORGANISM: Aequorea victoria
<220> FEATURE:
<221> NAME/KEY: misc_feature
<222> LOCATION: (1)..(738)
<223> OTHER INFORMATION: GFP-SEKDEL

<400> SEQUENCE: 15
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggcac     420 aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660

```
ctgctggagt tcgtgaccgc cgccgggatc actctcggca tggacgagct gtacaagtct      720
gagaaggatg agctctga                                                    738
```

<210> SEQ ID NO 16
<211> LENGTH: 245
<212> TYPE: PRT
<213> ORGANISM: Aequorea victoria
<220> FEATURE:
<221> NAME/KEY: MISC_FEATURE
<222> LOCATION: (1)..(245)
<223> OTHER INFORMATION: GFP-SEKDEL

<400> SEQUENCE: 16

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Glu Lys Asp Glu Leu
                245
```

<210> SEQ ID NO 17
<211> LENGTH: 11302
<212> TYPE: DNA
<213> ORGANISM: Artificial
<220> FEATURE:
<223> OTHER INFORMATION: synthetic vector sequence
<220> FEATURE:
<221> NAME/KEY: misc_feature
<222> LOCATION: (1)..(11302)
<223> OTHER INFORMATION: 133336 vector

<400> SEQUENCE: 17

```
catgccaacc acagggttcc cctcgggatc aaagtacttt gatccaaccc ctccgctgct    60
atagtgcagt cggcttctga cgttcagtgc agccgtcttc tgaaaacgac atgtcgcaca   120
agtcctaagt tacgcgacag gctgccgccc tgccctttc ctggcgtttt cttgtcgcgt   180
gttttagtcg cataaagtag aatacttgcg actagaaccg agacattac gccatgaaca   240
agagcgccgc cgctggcctg ctgggctatg cccgcgtcag caccgacgac caggacttga   300
ccaaccaacg ggccgaactg cacgcggccg gctgcaccaa gctgttttcc gagaagatca   360
ccggcaccag gcgcgaccgc ccggagctgg ccaggatgct tgaccaccta cgccctggcg   420
acgttgtgac agtgaccagg ctagaccgcc tggcccgcag cacccgcgac ctactggaca   480
ttgccgagcg catccaggag gccggcgcgg gcctgcgtag cctggcagag ccgtgggccg   540
acaccaccac gccggccggc cgcatggtgt tgaccgtgtt cgccggcatt gccgagttcg   600
agcgttccct aatcatcgac cgcacccgga gcgggcgcga ggccgccaag gcccgaggcg   660
tgaagtttgg cccccgccct accctcaccc cggcacagat cgcgcacgcc cgcgagctga   720
tcgaccagga aggccgcacc gtgaaagagg cggctgcact gcttggcgtg catcgctcga   780
ccctgtaccg cgcacttgag cgcagcgagg aagtgacgcc caccgaggcc aggcggcgcg   840
gtgccttccg tgaggacgca ttgaccgagg ccgacgccct ggcggccgcc gagaatgaac   900
gccaagagga acaagcatga aaccgcacca ggacggccag gacgaaccgt ttttcattac   960
cgaagagatc gaggcggaga tgatcgcggc cgggtacgtg ttcgagccgc ccgcgcacgt  1020
ctcaaccgtg cggctgcatg aaatcctggc cggtttgtct gatgccaagc tggcggcctg  1080
gccgccagc ttggccgctg aagaaaccga gcgccgccgt ctaaaaaggt gatgtgtatt  1140
tgagtaaaac agcttgcgtc atgcggtcgc tgcgtatatg atgcgatgag taaataaaca  1200
aatacgcaag gggaacgcat gaaggttatc gctgtactta accagaaagg cgggtcaggc  1260
aagacgacca tcgcaaccca tctagcccgc gccctgcaac tcgccggggc cgatgttctg  1320
ttagtcgatt ccgatcccca gggcagtgcc cgcgattggg cggccgtgcg gaagatcaa  1380
ccgctaaccg ttgtcggcat cgaccgcccg acgattgacc gcgacgtgaa ggccatcggc  1440
cggcgcgact tcgtagtgat cgacggagcg ccccaggcgg cggacttggc tgtgtccgcg  1500
atcaaggcag ccgacttcgt gctgattccg gtgcagccaa gcccttacga catatgggcc  1560
accgccgacc tggtggagct ggttaagcag cgcattgagg tcacggatgg aaggctacaa  1620
gcggcctttg tcgtgtcgcg ggcgatcaaa ggcacgcgca tcggcggtga ggttgccgag  1680
gcgctggccg ggtacgagct gcccattctt gagtcccgta tcacgcagcg cgtgagctac  1740
ccaggcactg ccgccgccgg cacaaccgtt cttgaatcag aacccgaggg cgacgctgcc  1800
cgcgaggtcc aggcgctggc cgctgaaatt aaatcaaaac tcatttgagt taatgaggta  1860
aagagaaaat gagcaaaagc acaaacacgc taagtgccgg ccgtccgagc gcacgcagca  1920
gcaaggctgc aacgttggcc agcctggcag acacgccagc catgaagcgg gtcaactttc  1980
agttgccggc ggaggatcac accaagctga agatgtacgc ggtacgccaa gcaagacca  2040
ttaccgagct gctatctgaa tacatcgcgc agctaccaga gtaaatgagc aaatgaataa  2100
atgagtagat gaattttagc ggctaaagga ggcggcatgg aaaatcaaga caaccaggc  2160
accgacgccg tggaatgccc catgtgtgga ggaacgggcg gttggccagg cgtaagcggc  2220
tgggttgtct gccggccctg caatggcact ggaacccca gcccgagga atcggcgtga  2280
cggtcgcaaa ccatccggcc cggtacaaat cggcgcggcg ctgggtgatg acctggtgga  2340
gaagttgaag gccgcgcagg ccgcccagcg gcaacgcatc gaggcagaag cacgccccgg  2400
```

```
tgaatcgtgg caagcggccg ctgatcgaat ccgcaaagaa tcccggcaac cgccggcagc    2460
cggtgcgccg tcgattagga agccgcccaa gggcgacgag caaccagatt ttttcgttcc    2520
gatgctctat gacgtgggca cccgcgatag tcgcagcatc atggacgtgg ccgttttccg    2580
tctgtcgaag cgtgaccgac gagctggcga ggtgatccgc tacgagcttc cagacgggca    2640
cgtagaggtt tccgcagggc cggccggcat ggccagtgtg tgggattacg acctggtact    2700 gatgcggtt tccatctaa ccgaatccat gaaccgatac cgggaaggga agggagacaa     2760
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccagggtga    2940 agccttgatt agccgctaca agatcgtaaa gagcgaaacc gggcggccgg agtacatcga    3000
gatcgagcta gctgattgga tgtaccgcga gatcacagaa ggcaagaacc cggacgtgct    3060
gacggttcac cccgattact ttttgatcga tcccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240
aaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaggtcga aaggtctct tcctgtgga      3420 tagcacgtac attgggaacc caaagccgta cattgggaac cggaacccgt acattgggaa    3480
cccaaagccg tacattggga accggtcaca catgtaagtg actgatataa aagagaaaaa    3540
aggcgatttt tccgcctaaa actctttaaa acttattaaa actcttaaaa cccgcctggc    3600
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accagggcgc ggacaagccg cgccgtcgcc    3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca gcccgtcag ggcgcgtcag cgggtgttgg cgggtgtcgg ggcgcagcca     3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
```

```
tctgctgaag ccagttacct tcggaaaaag agttggtagc tcttgatccg gcaaacaaac    4800
caccgctggt agcggtggtt tttttgtttg caagcagcag attacgcgca gaaaaaaagg    4860
atctcaagaa gatcctttga tctttttctac ggggtctgac gctcagtgga acgaaaactc   4920
acgttaaggg attttggtca tgcattctag gtactaaaac aattcatcca gtaaaatata    4980
atatttatt ttctcccaat caggcttgat ccccagtaag tcaaaaaata gctcgacata     5040
ctgttcttcc ccgatatcct ccctgatcga ccggacgcag aaggcaatgt cataccactt    5100
gtccgccctg ccgcttctcc caagatcaat aaagccactt actttgccat cttcacaaa    5160
gatgttgctg tctcccaggt cgccgtggga aaagacaagt tcctcttcgg gcttttccgt    5220
ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct ttgttcatct tcatactctt ccgagcaaag    5460
gacgccatcg gcctcactca tgagcagatt gctccagcca tcatgccgtt caaagtgcag    5520
gaccttttgga acaggcagct ttccttccag ccatagcatc atgtcctttt cccgttccac   5580
atcataggtg gtcccttttat accggctgtc cgtcattttt aaatataggt tttcatttttc  5640
tcccaccagc ttatatacct tagcaggaga cattccttcc gtatctttta cgcagcggta    5700
ttttttcgatc agttttttca attccggtga tattctcatt ttagccattt attatttcct   5760
tcctcttttc tacagtattt aaagatacccc caagaagcta attataacaa gacgaactcc   5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctg ttggctggct ggtgacagga    6180
tatattgttg tgttaacaaa ttgacgctta gacaacttaa taacacattg cggacgtttt    6240
taatgtagat ctagtaacat agatgacacc gcgcgcgata atttatccta gtttgcgcgc    6300
tatattttgt tttctatcgc gtattaaatg tataattgcg ggactctaat cataaaaacc    6360
catctcataa ataacgtcat gcattacatg ttaattatta catgcttaac gtaattcaac    6420
agaaattata tgataatcat cgcaagaccg gcaacaggat tcaatcttaa gaaactttat    6480
tgccaaatgt ttgaacgatc tcgactctag ctagaggatc gatccgaacc ccagagtccc    6540
gctcagaaga actcgtcaag aaggcgatag aaggcgatgc gctgcgaatc gggagcggcg    6600
ataccgtaaa gcacgaggaa gcggtcagcc cattcgccgc caagctcttc agcaatatca    6660
cgggtagcca acgctatgtc ctgatagcgg tccgccacac ccagccggcc acagtcgatg    6720
aatccagaaa agcggccatt ttccaccatg atattcggca agcaggcatc gccatgtgtc    6780
acgacgagat cctcgccgtc gggcatgcgc gccttgagcc tggcgaacag ttcggctggc    6840
gcgagcccct gatgctcttc gtccagatca tcctgatcga caagaccggc ttccatccga    6900
gtacgtgctc gctcgatgcg atgtttcgct tggtggtcga atgggcaggt agccggatca    6960
agcgtatgca gccgccgcat tgcatcagcc atgatggata cttttctcggc aggagcaagg   7020
tgagatgaca ggagatcctg ccccggcact tcgcccaata gcagccagtc ccttcccgct    7080
tcagtgacaa cgtcgagcac agctgcgcaa ggaacgcccg tcgtggccag ccacgatagc    7140
```

```
cgcgctgcct cgtcctggag ttcattcagg gcaccggaca ggtcggtctt gacaaaaaga    7200
accgggcgcc cctgcgctga cagccggaac acggcggcat cagagcagcc gattgtctgt    7260
tgtgcccagt catagccgaa tagcctctcc acccaagcgg ccggagaacc tgcgtgcaat    7320
ccatcttgtt caatccccat ggtcgatcga cagatctgcg aaagctcgag ctgttaatca    7380
gaaaaactca gattaatcga caattcgat cgcacaaact agaaactaac accagatcta    7440
gatagaaatc acaaatcgaa gagtaattat tcgacaaaac tcaaattatt tgaacaaatc    7500
ggatgatatc tatgaaaccc taatcgagaa ttaagatgat atctaacgat caaacccaga    7560
aaatcgtctt cgatctaaga ttaacagaat ctaaaccaaa gaacatatac gaaattggga    7620
tcgaacgaaa acaaaatcga agattttgag agaataagga acacagaaat ttaccttgat    7680
cacggtagag agaattgaga gaaagttttt aagattttga gaaattgaaa tctgaattgt    7740
gaagaagaag agctctttgg gtattgtttt atagaagaag aagaagaaaa gacgaggacg    7800
actaggtcac gagaaagcta aggcggtgaa gcaatagcta ataataaaat gacacgtgta    7860
ttgagcgttg tttacacgca aagttgtttt tggctaattg ccttatttttt aggttgagga    7920 aaagtatttg tgctttgagt tgataaacac gactcgtgtg tgccggctgc aaccactttg    7980
acgccgttta ttactgactc gtcgacaacc acaatttcta acggtcgtca taagatccag    8040
ccgttgagat ttaacgatcg ttacgattta tattttttta gcattatcgt tttattttt    8100 aaatatacgg tggagctgaa aattggcaat aattgaaccg tgggtcccac tgcattgaag    8160
cgtatttcgt atttttctaga attcttcgtg ctttatttct tttccttttt gtttttttt    8220 gccatttatc taatgcaagt gggcttataa aatcagtgaa tttcttggaa aagtaacttc    8280
tttatcgtat aacatattgt gaaattatcc attttctttta atttttttagt gttattggat    8340 atttttgtat gattattgat ttgcatagga taatgactttt tgtatcaagt tggtgaacaa    8400
gtctcgttaa aaaaggcaag tggttttggtg actcgattta ttcttgttat ttaattcata    8460
tatcaatgga tcttatttgg ggcctggtcc atatttaaca ctcgtgttca gtccaatgac    8520
caataatatt ttttcattaa taacaatgta acaagaatga tacacaaaac attctttgaa    8580
taagttcgct atgaagaagg gaacttatcc ggtcctagat catcagttca tacaaacctc    8640
catagagttc aacatcttaa acaagaatat cctgattgct ccaccatgtt ggcaagctgc    8700
tctagccaat acgcaaaccg cctctccccg cgcgttggcc gattcattaa tgcagctggc    8760
acgacaggtt tcccgactgg aaagcgggca gtgagcgcaa cgcaattaat gtgagttagc    8820
tcactcatta ggcaccccag gctttacact ttatgcttcc ggctcgtatg ttgtgtggaa    8880
ttgtgagcgg ataacaattt cacacaggaa acagctatga ccatgattac gaattcgagc    8940
tctaactata acggtcctaa ggtagcgagc gatcgcgcgt attggctaga gcagcttgcc    9000
aacatggtgg agcacgacac tctcgtctac tccaagaata tcaaagatac agtctcagaa    9060
gaccaaaggg ctattgagac ttttcaacaa agggtaatat cgggaaaccct cctcggattc    9120 cattgcccag ctatctgtca cttcatcaaa aggacagtag aaaaggaagg tggcacctac    9180
aaatgccatc attgcgataa aggaaaggct atcgttcaag atgcctctgc cgacagtggt    9240
cccaaagatg accccccacc cacgaggagc atcgtggaaa aagaagacgt tccaaccacg    9300
tcttcaaagc aagtggattg atgtgaacat ggtggagcac gacactctcg tctactccaa    9360
gaatatcaaa gatacagtct cagaagacca aagggctatt gagactttc aacaaagggt    9420 aatatcggga aacctcctcg gattccattg cccagctatc tgtcacttca tcaaaaggac    9480
```

```
agtagaaaag gaaggtggca cctacaaatg ccatcattgc gataaaggaa aggctatcgt      9540
tcaagatgcc tctgccgaca gtggtcccaa agatggaccc ccacccacga ggagcatcgt      9600
ggaaaaagaa gacgttccaa ccacgtcttc aaagcaagtg gattgatgtg atatctccac      9660
tgacgtaagg gatgacgcac aatcccacta tccttcgcaa gacccttcct ctatataagg      9720
aagttcattt catttggaga ggacacgctg aaatcaccag tctctctcta caaatctatc      9780
tctgtttaaa catggtgagc aagggcgagg agctgttcac cggggtggtg cccatcctgg      9840
tcgagctgga cggcgacgta aacggccaca agttcagcgt gtccggcgag ggcgagggcg      9900
atgccaccta cggcaagctg accctgaagt tcatctgcac caccggcaag ctgcccgtgc      9960
cctggcccac cctcgtgacc accctgacct acggcgtgca gtgcttcagc cgctacccg      10020 accacatgaa gcagcacgac ttcttcaagt ccgccatgcc cgaaggctac gtccaggagc      10080
gcaccatctt cttcaaggac gacggcaact acaagacccg cgccgaggtg aagttcgagg      10140
gcgacaccct ggtgaaccgc atcgagctga agggcatcga cttcaaggag gacggcaaca      10200
tcctggggca caagctggag tacaactaca acagccacaa cgtctatatc atggccgaca      10260
agcagaagaa cggcatcaag gtgaacttca gatccgcca caacatcgag gacggcagcg      10320
tgcagctcgc cgaccactac cagcagaaca cccccatcgg cgacggcccc gtgctgctgc      10380
ccgacaacca ctacctgagc acccagtccg ccctgagcaa agaccccaac gagaagcgcg      10440
atcacatggt cctgctagag ttcgtgaccg ccgccgggat cactctcggc atggacgagc      10500
tgtacaagtc tgagaaggat gagctctgac ggaccggatc tgtcgatcga caagctcgag      10560
tttctccata ataatgtgtg agtagttccc agataaggga attagggttc ctatagggtt      10620
tcgctcatgt gttgagcata taagaaaccc ttagtatgta tttgtatttg taaaatactt      10680
ctatcaataa aatttctaat tcctaaaacc aaaatccagt actaaaatcc agatccccg      10740 aattagcggc cgcattaccc tgttatccct actttcggat tataacatca catctatgtc      10800
gggtgcggag aaagaggtaa tgaaatggca tgacgatcaa ccataccaga taactatgac      10860
tctcttaagg tagccaaata atacccggtc tgaacgaggt ggcaaacagc tattatgggt      10920
attatgggtg gtacccgggg atcctctaga gtcgacctgc aggcatgcaa gcttggcact      10980
ggccgtcgtt ttacaacgtc gtgactggga aaaccctggc gttacccaac ttaatcgcct      11040
tgcagcacat cccccttcg ccagctggcg taatagcgaa gaggcccgca ccgatcgccc      11100
ttcccaacag ttgcgcagcc tgaatggcga atgctagagc agcttgagct tggatcagat      11160
tgtcgtttcc cgccttcagt ttaaactatc agtgtttgac aggatatatt ggcgggtaaa      11220
cctaagagaa aagagcgttt attagaataa cggatattta aaagggcgtg aaaaggttta      11280
tccgttcgtc catttgtatg tg                                               11302
```

<210> SEQ ID NO 18
<211> LENGTH: 9172
<212> TYPE: DNA
<213> ORGANISM: Artificial
<220> FEATURE:
<223> OTHER INFORMATION: plant transformation vector
<220> FEATURE:
<221> NAME/KEY: misc_feature
<222> LOCATION: (1)..(9172)
<223> OTHER INFORMATION: 133869 vector
<220> FEATURE:
<221> NAME/KEY: misc_feature
<222> LOCATION: (2354)..(6184)
<223> OTHER INFORMATION: Lb6Cpf1

<400> SEQUENCE: 18

-continued

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa agggggatgt     240
gctgcaaggc gattaagttg ggtaacgcca gggttttccc agtcacgacg ttgtaaaacg     300
acggccagtg agcgcgacgt aatacgactc actatagggc gaattggcgg aaggccgtca     360
aggccgcatc ccgggttgta gctccacgcg cttcggcagg ggaagctcta cttaatcgga     420
agtccatatg taactataac ggtcctaagg tagcgagcga tcgcctgcag tgcagcgtga     480
cccggtcgtg cccctctcta gagataatga gcattgcatg tctaagttat aaaaaattac     540
cacatatttt ttttgtcaca cttgtttgaa gtgcagttta tctatcttta tacatatatt     600
taaactttac tctacgaata atataatcta tactactaca ataatatcag tgttttagag     660
aatcatataa atgaacagtt agacatggtc taaaggacaa ttgagtattt tgacaacagg     720
actctacagt tttatctttt tagtgtgcat gtgttctcct ttttttttgc aaatagcttc     780
acctatataa tacttcatcc attttattag tacatccatt tagggtttag ggttaatggt     840
ttttatagac taattttttt agtacatcta ttttattcta ttttagcctc taaattaaga     900
aaactaaaac tctattttag tttttttatt taataattta gatataaaat agaataaaat     960
aaagtgacta aaaattaaac aaataccctt taagaaatta aaaaaactaa ggaaacattt    1020
ttcttgtttc gagtagataa tgccagcctg ttaaacgccg tcgacgagtc taacggacac    1080
caaccagcga accagcagcg tcgcgtcggg ccaagcgaag cagacggcac ggcatctctg    1140
tcgctgcctc tggaccccctc tcgagagttc cgctccaccg ttggacttgc tccgctgtcg    1200
gcatccagaa attgcgtggc ggagcggcag acgtgagccg gcacggcagg cggcctcctc    1260
ctcctctcac ggcacggcag ctacggggga ttccttcccc accgctcctt cgctttccct    1320
tcctcgcccg ccgtaataaa tagacacccc ctccacaccc tctttcccca acctcgtgtt    1380
gttcggagcg cacacacaca caaccagatc tcccccaaat ccacccgtcg gcacctccgc    1440
ttcaaggtac gccgctcgtc ctccccccccc ccccctctct accttctcta gatcggcgtt    1500
ccggtccatg gttagggccc ggtagttcta cttctgttca tgtttgtgtt agatccgtgt    1560
ttgtgttaga tccgtgctgc tagcgttcgt acacggatgc gacctgtacg tcagacacgt    1620
tctgattgct aacttgccag tgtttctctt tggggaatcc tgggatggct ctagccgttc    1680
cgcagacggg atcgatttca tgattttttt tgtttcgttg catagggttt ggtttgccct    1740
tttcctttat ttcaatatat gccgtgcact tgtttgtcgg gtcatctttt catgcttttt    1800
tttgtcttgg ttgtgatgat gtggtctggt tgggcggtcg ttctagatcg gagtagaatt    1860
ctgtttcaaa ctacctggtg gatttattaa ttttggatct gtatgtgtgt gccatacata    1920
ttcatagtta cgaattgaag atgatggatg gaaatatcga tctaggatag gtatacatgt    1980
tgatgcgggt tttactgatg catatacaga gatgcttttt gttcgcttgg ttgtgatgat    2040
gtggtgtggt tgggcggtcg ttcattcgtt ctagatcgga gtagaatact gtttcaaact    2100
acctggtgta tttattaatt ttggaactgt atgtgtgtgt catacatctt catagttacg    2160
agtttaagat ggatggaaat atcgatctag gataggtata catgttgatg tgggttttac    2220
tgatgcatat acatgatggc atatgcagca tctattcata tgctctaacc ttgagtacct    2280
atctattata ataaacaagt atgttttata attattttga tcttgatata ctgattttttt    2340
```

-continued

```
tagccctgcc ttcatggatg atggcatatg cagcagctat atgtgtacgc tatttatttg    2400
cttggtactg tttcttttgt cgatgctcac cctgttgttt ggtgttactt ctgcaggttt    2460
aaacatggcc ccaaagaaaa agcgcaaggt gatgcacgag aacaacggca agatcgccga    2520
taacttcatc ggcatctacc ccgtgtctaa gacccttagg ttcgagctta agccagtggg    2580
aaagacccaa gagtacatcg agaagcacgg aatcctcgat gaggatctta agcgcgctgg    2640
cgattacaag tccgtgaaga agattatcga cgcctaccac aagtacttca tcgacgaggc    2700
tctcaacgga atccagcttg atggactcaa gaactactac gagctgtacg agaagaagcg    2760
cgacaacaac gaagagaaag agttccaaaa gatccgagatg tccctgcgca agcagatcgt    2820
gaagagattc tctgagcacc acagtacaa gtacctcttc aagaaagaac tcatcaagaa    2880
cgtgctcccc gagttcacca aggataacgc tgaggaacag accctcgtga agtccttcca    2940
agagttcact acctacttcg agggcttcca ccagaaccgc aagaacatgt actccgacga    3000
ggaaaagtcc accgctatcg cttacagggt tgtgcatcag aacctgccaa agtacattga    3060
caacatgcgc atcttctcca tgatcctcaa caccgacatc cgctctgatc tcaccgagct    3120
tttcaacaac ctcaagacca agatggacat caccatcgtg aagagtact tcgctatcga    3180
cggcttcaac aaggtggtga accagaaagg catcgacgtg tacaacacca tcctcggagc    3240
tttctccacc gatgacaaca ccaagatcaa gggcctcaac gagtacatca acctctacaa    3300
ccagaagaac aaggctaagc tccccaagct caagccactc ttcaagcaga ttctctccga    3360
ccgcgacaag atctccttca ttccagagca gttcgactcc gataccgagg ttttggaggc    3420
tgtggatatg ttctacaacc gccttctcca gttcgtgatc gagaacgagg acagattac    3480
catctccaag ctcctcacca acttctccgc ttacgacctc aacaagatct acgtgaagaa    3540
cgacaccacc atctccgcca tctctaacga tctcttcgac gactggtcct acatctctaa    3600
ggctgtgaga gagaactacg actccgagaa cgtggacaag aacaagagag ctgctgccta    3660
cgaagaaaag aaagagaagg ccctctccaa gattaagatg tactcaatcg aggaactcaa    3720
cttcttcgtc aagaagtact cctgcaacga gtgccacatc gagggatact tcgagagaag    3780
gatcctcgag attctcgaca agatgaggta cgcctacgag tcctgcaaga tccttcacga    3840
taagggcctg atcaacaaca tcagcctttg ccaagatagg caggccatct ccgagttgaa    3900
ggatttcctc gactccatca agaggtgca gtggcttctt aagccactca tgattggaca    3960
agagcaggcc gacaaagaag aggccttcta cactgagctt ctccgcattt gggaagagtt    4020
ggagccaatc actctgctct acaacaaggt tcgcaactac gtgaccaaga agccctacac    4080
tcttgagaag gtgaagctga acttctacaa gagcaccctc ctcgatggct gggataagaa    4140
caaagaaaag gacaacctcg gatcatcct cctcaaggat ggacagtact acctcggcat    4200
tatgaaccgc cgcaacaaca agattgctga tgatgctcca ctcgccaaga ccgacaacgt    4260
gtacagaaag atggagtaca gttgctcac caaggtgtcc gctaacctgc ctaggatctt    4320
cctgaaggac aagtacaacc cctccgaaga gatgctcgag aagtatgaga agggaaccca    4380
cctcaagggt gagaacttct gcattgatga ctgccgcgag ctgatcgact tcttcaaaaa    4440
gggcatcaag cagtacgagg actggggcca attcgacttc aagttctctg acaccgagtc    4500
ctacgatgac atctccgctt tctacaaaga ggttgagcac cagggctaca agattacctt    4560
cagggatatc gacgagactt acatcgacag ccttgtgaac gagggtaagc tctacctctt    4620
ccagatctat aacaaggact tctcaccata ctccaagggc accaagaacc ttcacaccct    4680
ttactgggag atgctgttct cccagcagaa cctccagaac atcgtgtaca agctcaacgg    4740
```

```
caacgccgag atcttctacc gcaaggcttc tattaaccag aaggacgtcg tcgtccacaa    4800
ggccgatttg cccatcaaaa acaaggaccc acagaactct aagaaagaat ccatgttcga    4860
ctacgacatc atcaaggaca agcgcttcac ttgcgacaag taccagttcc acgtgccaat    4920
caccatgaac ttcaaggctc ttggggagaa ccacttcaac cgtaaggtga acaggctcat    4980
ccacgacgct gagaacatgc acatcatcgg aattgatcgc ggagagcgca accttatcta    5040
cctctgcatg atcgacatga agggcaacat tgtgaagcag atctccctga cgagatcat     5100 ctcctacgac aaaaacaaac tcgagcacaa gcgcaactac caccagttgc ttaagaccag    5160
agaggatgag aacaagtccg ctaggcaatc ctggcagacc atccacacta tcaaagagct    5220
gaaagagggc tacctcagcc aggttatcca tgtgattacc gacctcatgg tcgagtacaa    5280
cgctattgtg gtgcttgagg acctgaactt cggattcaag caaggcaggc aaaagttcga    5340
gaggcaggtc taccagaaat tcgagaagat gttgatcgat aagctcaact acctggtgga    5400
caagtccaaa ggcatggatg aggatggcgg attgcttcac gcttaccaac ttaccgacga    5460
gttcaagtct ttcaagcagc tcggaaagca gtccggcttc ctctattaca ttccagcctg    5520
gaacaccagc aagctcgatc caactactgg attcgtgaac ctcttctaca ccaagtacga    5580
gtccgtcgag aagtctaaag agttcatcaa caacttcacc tccatcctct acaatcaaga    5640
gcgcgagtat ttcgagttcc tcttcgacta ctctgccttc acctctaagg cagagggatc    5700
cagacttaag tggaccgttt gctccaaggg tgaacgcgtt gagacttata ggaaccccaa    5760
gaaaaacaac gagtgggaca cccagaagat cgaccttacc ttcgaactca agaagctgtt    5820
caacgactac tccatttcct tgctcgatgg cgatctcagg gaacagatgg gaaagatcga    5880
caaggctgac ttctataaga aattcatgaa gcttttcgcc ctcatcgtcc agatgaggaa    5940
ctctgatgag cgcgaggaca agctcatttc cccagtgctt aacaagtacg gcgccttctt    6000
cgaaaccgga agaacgagaa gaatgccact cgatgctgat gctaacggcg cttacaacat    6060
tgctaggaaa ggcctctgga tcatcgaaaa gatcaagaac accgacgttg agcagctcga    6120
caaggtcaag ctcaccatca gcaacaaaga gtggttgcag tacgctcaag agcacatcct    6180
ttgacggacc ggtcatgggt cgtttaagct gccgatgtgc ctgcgtcgtc tggtgccctc    6240
tctccatatg gaggttgtca agtatctgc tgttcgtgtc atgagtcgtg tcagtgttgg     6300
tttaataatg gaccggttgt gttgtgtgtg cgtactaccc agaactatga caaatcatga    6360
ataagtttga tgtttgaaat taaagcctgt gctcattatg ttctgtcttt cagttgtctc    6420
ctaatatttg cctgcaggta ctggctatct accgtttctt acttaggagg tgtttgaatg    6480
cactaaaact aatagttagt ggctaaaatt agttaaaaca tccaaacacc atagctaata    6540
gttgaactat tagctatttt tggaaaatta gttaatagtg aggtagttat tgttagcta     6600 gctaattcaa ctaacaattt ttagccaact aacaattagt ttcagtgcat tcaaacaccc    6660
ccttaatgtt aacgtggttc tatctaccgt ctcctaatat atggttgatt gttcggtttg    6720
ttgctatgct attgggttct gattgctgct agttcttgct gaatccagaa gttctcgtag    6780
tatagctcag attcatatta tttatttgag tgatggcgcg cccgagtatc gaattcctgc    6840
aggcatgcaa gcgatccccg atcgttcaaa catttggcaa taaagtttct taagattgaa    6900
tcctgttgcc ggtcttgcga tgattatcat ataatttctg ttgaattacg ttaagcatgt    6960
aataattaac atgtaatgca tgacgttatt tatgagatgg gttttatga ttagagtccc     7020 gcaattatac atttaatacg cgatagaaaa caaaatatag cgcgcaaact aggataaatt    7080
```

```
atcgcgcgcg gtgtcatcta tgttactaga tcggcggccg cattaccctg ttatccctaa    7140
agcttgaatt cagtacatta aaaacgtccg caatgtgtta ttaagttgtc taagcccggg    7200
ctgggcctca tgggccttcc gctcactgcc cgctttccag tcgggaaacc tgtcgtgcca    7260
gctgcattaa catggtcata gctgtttcct tgcgtattgg cgctctccg  cttcctcgct    7320
cactgactcg ctgcgctcgg tcgttcgggt aaagcctggg gtgcctaatg agcaaaaggc    7380
cagcaaaagg ccaggaaccg taaaaaggcc gcgttgctgg cgttttttcca taggctccgc    7440
ccccctgacg agcatcacaa aaatcgacgc tcaagtcaga ggtggcgaaa cccgacagga    7500
ctataaagat accaggcgtt tccccctgga agctccctcg tgcgctctcc tgttccgacc    7560
ctgccgctta ccggatacct gtccgccttt ctcccttcgg gaagcgtggc gctttctcat    7620
agctcacgct gtaggtatct cagttcggtg taggtcgttc gctccaagct gggctgtgtg    7680
cacgaacccc ccgttcagcc cgaccgctgc gccttatccg gtaactatcg tcttgagtcc    7740
aacccggtaa gacacgactt atcgccactg gcagcagcca ctggtaacag gattagcaga    7800
gcgaggtatg taggcggtgc tacagagttc ttgaagtggt ggcctaacta cggctacact    7860
agaagaacag tatttggtat ctgcgctctg ctgaagccag ttaccttcgg aaaaagagtt    7920
ggtagctctt gatccggcaa acaaaccacc gctggtagcg gtggtttttt tgtttgcaag    7980
cagcagatta cgcgcagaaa aaaggatct  caagaagatc ctttgatctt ttctacgggg    8040
tctgacgctc agtggaacga aaactcacgt taagggattt tggtcatgag attatcaaaa    8100
aggatcttca cctagatcct tttaaattaa aaatgaagtt ttaaatcaat ctaaagtata    8160
tatgagtaaa cttggtctga cagttaccaa tgcttaatca gtgaggcacc tatctcagcg    8220
atctgtctat ttcgttcatc catagttgcc tgactccccg tcgtgtagat aactacgata    8280
cgggagggct taccatctgg ccccagtgct gcaatgatac cgcgagaacc acgctcaccg    8340
gctccagatt tatcagcaat aaaccagcca gccggaaggg ccgagcgcag aagtggtcct    8400
gcaactttat ccgcctccat ccagtctatt aattgttgcc gggaagctag agtaagtagt    8460
tcgccagtta atagtttgcg caacgttgtt gccattgcta caggcatcgt ggtgtcacgc    8520
tcgtcgtttg gtatggcttc attcagctcc ggttcccaac gatcaaggcg agttacatga    8580
tcccccatgt tgtgcaaaaa agcggttagc tccttcggtc ctccgatcgt tgtcagaagt    8640
aagttggccg cagtgttatc actcatggtt atggcagcac tgcataattc tcttactgtc    8700
atgccatccg taagatgctt ttctgtgact ggtgagtact caaccaagtc attctgagaa    8760
tagtgtatgc ggcgaccgag ttgctcttgc ccggcgtcaa tacgggataa taccgcgcca    8820
catagcagaa ctttaaaagt gctcatcatt ggaaaacgtt cttcggggcg aaaactctca    8880
aggatcttac cgctgttgag atccagttcg atgtaaccca ctcgtgcacc caactgatct    8940
tcagcatctt ttactttcac cagcgtttct gggtgagcaa aaacaggaag gcaaaatgcc    9000
gcaaaaaagg  gaataagggc gacacggaaa tgttgaatac tcatactctt ccttttccaa    9060
tattattgaa gcatttatca gggttattgt ctcatgagcg gatacatatt tgaatgtatt    9120
tagaaaaata acaaataggg gttccgcgc  acatttcccc gaaaagtgcc ac             9172
```

<210> SEQ ID NO 19
<211> LENGTH: 3095
<212> TYPE: DNA
<213> ORGANISM: Artificial
<220> FEATURE:
<223> OTHER INFORMATION: plant transformation vector
<220> FEATURE:
<221> NAME/KEY: misc_feature
<222> LOCATION: (1)..(3095)
<223> OTHER INFORMATION: vector 133432
<220> FEATURE:
<221> NAME/KEY: misc_feature
<222> LOCATION: (982)..(1024)
<223> OTHER INFORMATION: gRNA

<400> SEQUENCE: 19

| | | | | | |
|---|---|---|---|---|---|
| ctaaattgta | agcgttaata | ttttgttaaa | attcgcgtta | aattttttgtt | aaatcagctc | 60 |
| attttttaac | caataggccg | aaatcggcaa | aatcccttat | aaatcaaaag | aatagaccga | 120 |
| gatagggttg | agtggccgct | acagggcgct | cccattcgcc | attcaggctg | cgcaactgtt | 180 |
| gggaagggcg | tttcggtgcg | ggcctcttcg | ctattacgcc | agctggcgaa | aggggggatgt | 240 |
| gctgcaaggc | gattaagttg | ggtaacgcca | gggttttccc | agtcacgacg | ttgtaaaacg | 300 |
| acggccagtg | agcgcgacgt | aatacgactc | actatagggc | gaattggcgg | aaggccgtca | 360 |
| aggccgcatc | ccgggttgta | gctccacgcg | cttcggcagg | ggaagctcta | cttaatcgga | 420 |
| agtccatatg | taactataac | ggtcctaagg | tagcgagcga | tcgctttgtg | aaagttgaat | 480 |
| tacggcatag | ccgaaggaat | aacagaatcg | tttcacactt | tcgtaacaaa | ggtcttctta | 540 |
| tcatgtttca | gacgatggag | gcaaggctga | tcaaagtgat | caagcacata | aacgcatttt | 600 |
| tttaccatgt | ttcactccat | aagcgtctga | gattatcaca | agtcacgtct | agtagtttga | 660 |
| tggtacacta | gtgacaatca | gttcgtgcag | acagagctca | tacttgacta | cttgagcgat | 720 |
| tacaggcgaa | agtgtgaaac | gcatgtgatg | tgggctggga | ggaggagaat | atatactaat | 780 |
| gggccgtatc | ctgatttggg | ctgcgtcgga | aggtgcagcc | cacgcgcgcc | gtaccgcgcg | 840 |
| ggtggcgctg | ctacccactt | tagtccgttg | gatggggatc | cgatggtttg | cgcggtggcg | 900 |
| ttgcggggga | tgtttagtac | cacatcggaa | accgaaagac | gatggaacca | gcttataaac | 960 |
| ccgcgcgctg | tagtcagctt | gaatttctac | tgttgtagat | aagggaccgc | agcaagctgc | 1020 |
| cgggtttttt | tgttttgcgg | ccgcattacc | ctgttatccc | taaagcttga | attcagtaca | 1080 |
| ttaaaaacgt | ccgcaatgtg | ttattaagtt | gtctaagccc | gggctgggcc | tcatgggcct | 1140 |
| tccgctcact | gcccgctttc | cagtcggaa | acctgtcgtg | ccagctgcat | taacatggtc | 1200 |
| atagctgttt | ccttgcgtat | tgggcgctct | ccgcttcctc | gctcactgac | tcgctgcgct | 1260 |
| cggtcgttcg | ggtaaagcct | ggggtgccta | atgagcaaaa | ggccagcaaa | aggccaggaa | 1320 |
| ccgtaaaaag | gccgcgttgc | tggcgttttt | ccataggctc | cgcccccctg | acgagcatca | 1380 |
| caaaaatcga | cgctcaagtc | agaggtggcg | aaacccgaca | ggactataaa | gataccaggc | 1440 |
| gtttccccct | ggaagctccc | tcgtgcgctc | tcctgttccg | accctgccgc | ttaccggata | 1500 |
| cctgtccgcc | tttctccctt | cgggaagcgt | ggcgctttct | catagctcac | gctgtaggta | 1560 |
| tctcagttcg | gtgtaggtcg | ttcgctccaa | gctgggctgt | gtgcacgaac | cccccgttca | 1620 |
| gcccgaccgc | tgcgccttat | ccggtaacta | tcgtcttgag | tccaacccgg | taagacacga | 1680 |
| cttatcgcca | ctggcagcag | ccactggtaa | caggattagc | agagcgaggt | atgtaggcgg | 1740 |
| tgctacagag | ttcttgaagt | ggtggcctaa | ctacggctac | actagaagaa | cagtatttgg | 1800 |
| tatctgcgct | ctgctgaagc | cagttacctt | cggaaaaaga | gttggtagct | cttgatccgg | 1860 |
| caaacaaacc | accgctggta | gcggtggttt | ttttgtttgc | aagcagcaga | ttacgcgcag | 1920 |
| aaaaaaagga | tctcaagaag | atcctttgat | cttttctacg | gggtctgacg | ctcagtggaa | 1980 |
| cgaaaactca | cgttaaggga | ttttggtcat | gagattatca | aaaaggatct | tcacctagat | 2040 |
| ccttttaaat | taaaaatgaa | gttttaaatc | aatctaaagt | atatatgagt | aaacttggtc | 2100 |

| | |
|---|---|
| tgacagttac caatgcttaa tcagtgaggc acctatctca gcgatctgtc tatttcgttc | 2160 |
| atccatagtt gcctgactcc ccgtcgtgta gataactacg atacgggagg gcttaccatc | 2220 |
| tggcccccagt gctgcaatga taccgcgaga accacgctca ccggctccag atttatcagc | 2280 |
| aataaaccag ccagccggaa gggccgagcg cagaagtggt cctgcaactt tatccgcctc | 2340 |
| catccagtct attaattgtt gccgggaagc tagagtaagt agttcgccag ttaatagttt | 2400 |
| gcgcaacgtt gttgccattg ctacaggcat cgtggtgtca cgctcgtcgt ttggtatggc | 2460 |
| ttcattcagc tccggttccc aacgatcaag gcgagttaca tgatccccca tgttgtgcaa | 2520 |
| aaaagcggtt agctccttcg gtcctccgat cgttgtcaga agtaagttgg ccgcagtgtt | 2580 |
| atcactcatg gttatggcag cactgcataa ttctcttact gtcatgccat ccgtaagatg | 2640 |
| cttttctgtg actggtgagt actcaaccaa gtcattctga aatagtgta tgcggcgacc | 2700 |
| gagttgctct tgcccggcgt caatacggga taataccgcg ccacatagca gaactttaaa | 2760 |
| agtgctcatc attggaaaac gttcttcggg gcgaaaactc tcaaggatct taccgctgtt | 2820 |
| gagatccagt tcgatgtaac ccactcgtgc acccaactga tcttcagcat cttttacttt | 2880 |
| caccagcgtt tctgggtgag caaaaacagg aaggcaaaat gccgcaaaaa agggaataag | 2940 |
| ggcgacacgg aaatgttgaa tactcatact cttcctttt caatattatt gaagcattta | 3000 |
| tcagggttat tgtctcatga gcggatacat atttgaatgt atttagaaaa ataaacaaat | 3060 |
| aggggttccg cgcacatttc cccgaaaagt gccac | 3095 |

```
<210> SEQ ID NO 20
<211> LENGTH: 5846
<212> TYPE: DNA
<213> ORGANISM: Artificial
<220> FEATURE:
<223> OTHER INFORMATION: plant transformation vector
<220> FEATURE:
<221> NAME/KEY: misc_feature
<222> LOCATION: (1)..(5846)
<223> OTHER INFORMATION: vector 131592
<220> FEATURE:
<221> NAME/KEY: misc_feature
<222> LOCATION: (722)..(1754)
<223> OTHER INFORMATION: hygromycin resistance gene

<400> SEQUENCE: 20
```

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |
| aggccgcatc ccgggttgta gctccacgcg cttcggcagg ggaagctcta cttaatcgga | 420 |
| agtccatatg atctatgtcg ggtgcggaga aagaggtaat gaaatggcag cgatcgcagc | 480 |
| tgaattaacg ccgaattaat tcgggggatc tggattttag tactggattt tggttttagg | 540 |
| aattagaaat tttattgata gaagtatttt acaaatacaa atacatacta agggtttctt | 600 |
| atatgctcaa cacatgagcg aaaccctata ggaaccctaa ttcccttatc tgggaactac | 660 |
| tcacacatta ttatggagaa actcgagctt gtcgatcgac agatcccggt cggcatctac | 720 |
| tctatttctt tgccctcgga cgagtgctgg ggcgtcggtt tccactatcg cgagtactt | 780 |
| ctacacagcc atcggtccag acggccgcgc ttctgcgggc gatttgtgta cgcccgacag | 840 |

```
tcccggctcc ggatcggacg attgcgtcgc atcgaccctg cgcccaagct gcatcatcga    900
aattgccgtc aaccaagctc tgatagagtt ggtcaagacc aatgcggagc atatacgccc    960
ggagtcgtgg cgatcctgca agctccggat gcctccgctc gaagtagcgc gtctgctgct   1020
ccatacaagc caaccacggc ctccagaaga agatgttggc gacctcgtat tgggaatccc   1080
cgaacatcgc ctcgctccag tcaatgaccg ctgttatgcg gccattgtcc gtcaggacat   1140
tgttggagcc gaaatccgcg tgcacgaggt gccggacttc ggggcagtcc tcggcccaaa   1200
gcatcagctc atcgagagcc tgcgcgacgg acgcactgac ggtgtcgtcc atcacagttt   1260
gccagtgata cacatgggga tcagcaatcg cgcatatgaa atcacgccat gtagtgtatt   1320
gaccgattcc ttgcggtccg aatgggccga acccgctcgt ctggctaaga tcggccgcag   1380
cgatcgcatc catagcctcc gcgaccggtt gtagaacagc gggcagttcg gtttcaggca   1440
ggtcttgcaa cgtgacaccc tgtgaacggc gggagatgca ataggtcagg ctctcgctaa   1500
actccccaat gtcaagcact tccggaatcg ggagcgcggc cgatgcaaag tgccgataaa   1560
cataacgatc tttgtagaaa ccatcggcgc agctatttac ccgcaggaca tatccacgcc   1620
ctcctacatc gaagctgaaa gcacgagatt cttcgccctc cgagagctgc atcaggtcgg   1680
agacgctgtc gaacttttcg atcagaaact tctcgacaga cgtcgcggtg agttcaggct   1740
ttttcatatc tcattgcccg ggaagcttat cgtctacctg cagaagtaac accaaacaac   1800
agggtgagca tcgacaaaag aaacagtacc aagcaaataa atagcgtatg aaggcagggc   1860
taaaaaaatc cacatatagc tgctgcatat gccatcatcc aagtatatca agatcaaaat   1920
aattataaaa catacttgtt tattataata gataggtact caaggttaga gcatatgaat   1980
agatgctgca tatgccatca tgtatatgca tcagtaaaac ccacatcaac atgtatacct   2040
atcctagatc gatatttcca tccatcttaa actcgtaact atgaagatgt atgacacaca   2100
catacagttc caaaattaat aaatacacca ggtagtttga acagtattc tactccgatc    2160 tagaacgaat gaacgaccgc ccaaccacac cacatcatca caaccaagcg aacaaaaagc   2220
atctctgtat atgcatcagt aaaacccgca tcaacatgta tacctatcct agatcgatat   2280
ttccatccat catcttcaat tcgtaactat gaatatgtat ggcacacaca tacagatcca   2340
aaattaataa atccaccagg tagttttgaaa cagaattcta ctccgatcta gaacgaccgc   2400
ccaaccagac cacatcatca caaccaagac aaaaaaaagc atgaaaagat gacccgacaa   2460
acaagtgcac ggcatatatt gaaataaagg aaaagggcaa accaaaccct atgcaacgaa   2520
acaaaaaaaa tcatgaaatc gatcccgtct gcggaacggc tagagccatc ccaggattcc   2580
ccaaagagaa acactggcaa gttagcaatc agaacgtgtc tgacgtacag gtcgcatccg   2640
tgtacgaacg ctagcagcac ggatctaaca caaacacgga tctaacacaa acatgaacag   2700
aagtagaact accgggccct aaccatggac cggaacgccg atctagagaa ggtagagagg   2760 ggggggggg gaggacgagc ggcgtaccct gaagcggagg tgccgacggg tggatttggg    2820
ggagatctgg ttgtgtgtgt gtgcgctccg aacaacacga ggttggggaa agagggtgtg   2880 gaggggggtgt ctatttatta cggcgggcga ggaagggaaa gcgaaggagc ggtgggaaag   2940
gaatcccccg tagctgccgt gccgtgagag gaggaggagg ccgcctgccg tgccggctca   3000
cgtctgccgc tccgccacgc aatttctgga tgccgacagc ggagcaagtc caacggtgga   3060
gcggaactct cgagagggt ccagaggcag cgacagagat gccgtgccgt ctgcttcgct    3120
tggcccgacg cgacgctgct ggttcgctgg ttggtgtccg ttagactcgt cgacggcgtt   3180
```

```
taacaggctg gcattatcta ctcgaaacaa gaaaaatgtt tccttagttt ttttaatttc    3240
ttaaagggta tttgtttaat ttttagtcac tttattttat tctattttat atctaaatta    3300
ttaaataaaa aaactaaaat agagttttag ttttcttaat ttagaggcta aaatagaata    3360
aaatagatgt actaaaaaaa ttagtctata aaaaccatta accctaaacc ctaaatggat    3420
gtactaataa aatggatgaa gtattatata ggtgaagcta tttgcaaaaa aaaggagaa     3480 cacatgcaca ctaaaaagat aaaactgtag agtcctgttg tcaaaatact caattgtcct    3540
ttagaccatg tctaactgtt catttatatg attctctaaa acactgatat tattgtagta    3600
gtatagatta tattattcgt agagtaaagt ttaaatatat gtaaagat agataaactg     3660 cacttcaaac aagtgtgaca aaaaaatat gtggtaattt tttataactt agacatgcaa     3720
tgctcattat ctctagagag gggcacgacc gggtcacgct gcactgcaga agcttgctgg    3780
cggccgccta tgactctctt aaggtagcca aataagcttg aattcagtac attaaaaacg    3840
tccgcaatgt gttattaagt tgtctaagcc cgggctgggc tcatgggcc ttccgctcac     3900 tgcccgcttt ccagtcggga aacctgtcgt gccagctgca ttaacatggt catagctgtt    3960
tccttgcgta ttgggcgctc tccgcttcct cgctcactga ctcgctgcgc tcggtcgttc    4020
gggtaaagcc tggggtgcct aatgagcaaa aggccagcaa aaggcagga accgtaaaaa     4080 ggccgcgttg ctggcgtttt tccataggct ccgcccccct gacgagcatc acaaaaatcg    4140
acgctcaagt cagaggtggc gaaacccgac aggactataa agataccagg cgtttccccc    4200
tggaagctcc ctcgtgcgct ctcctgttcc gaccctgccg cttaccggat acctgtccgc    4260
ctttctccct tcgggaagcg tggcgctttc tcatagctca cgctgtaggt atctcagttc    4320
ggtgtaggtc gttcgctcca agctgggctg tgtgcacgaa ccccccgttc agcccgaccg    4380
ctgcgcctta tccggtaact atcgtcttga gtccaacccg gtaagacacg acttatcgcc    4440
actggcagca gccactggta acaggattag cagagcgagg tatgtaggcg gtgctacaga    4500
gttcttgaag tggtggccta actacggcta cactagaaga acagtatttg gtatctgcgc    4560
tctgctgaag ccagttacct tcggaaaaag agttggtagc tcttgatccg gcaaacaaac    4620
caccgctggt agcggtggtt ttttttgtttg caagcagcag attacgcgca gaaaaaaagg    4680
atctcaagaa gatcctttga tcttttctac ggggtctgac gctcagtgga acgaaaactc    4740
acgttaaggg attttggtca tgagattatc aaaaaggatc ttcacctaga tccttttaaa    4800
ttaaaaatga gttttaaat caatctaaag tatatatgag taaacttggt ctgacagtta     4860
ccaatgctta atcagtgagg cacctatctc agcgatctgt ctatttcgtt catccatagt    4920
tgcctgactc cccgtcgtgt agataactac gatacgggag ggcttaccat ctggccccag    4980
tgctgcaatg ataccgcgag aaccacgctc accggctcca gatttatcag caataaacca    5040
gccagccgga agggccgagc gcagaagtgg tcctgcaact ttatccgcct ccatccagtc    5100
tattaattgt tgccgggaag ctagagtaag tagttcgcca gttaatagtt tgcgcaacgt    5160
tgttgccatt gctacaggca tcgtggtgtc acgctcgtcg tttggtatgg cttcattcag    5220
ctccggttcc caacgatcaa ggcgagttac atgatccccc atgttgtgca aaaaagcggt    5280
tagctccttc ggtcctccga tcgttgtcag aagtaagttg gccgcagtgt tatcactcat    5340
ggttatggca gcactgcata attctcttac tgtcatgcca tccgtaagat gcttttctgt    5400
gactggtgag tactcaacca agtcattctg agaatagtgt atgcggcgac cgagttgctc    5460
ttgcccggcg tcaatacggg ataataccgc gccacatagc agaactttaa aagtgctcat    5520
cattggaaaa cgttcttcgg ggcgaaaact ctcaaggatc ttaccgctgt tgagatccag    5580
```

```
ttcgatgtaa cccactcgtg cacccaactg atcttcagca tcttttactt tcaccagcgt    5640
ttctgggtga gcaaaaacag gaaggcaaaa tgccgcaaaa aagggaataa gggcgacacg    5700
gaaatgttga atactcatac tcttcctttt tcaatattat tgaagcattt atcagggtta    5760
ttgtctcatg agcggataca tatttgaatg tatttagaaa aataaacaaa taggggttcc    5820
gcgcacattt ccccgaaaag tgccac                                         5846
```

PRE-CONDITIONING TREATMENTS TO IMPROVE PLANT TRANSFORMATION

CROSS-REFERENCE TO RELATED APPLICATIONS

This application is a national stage filing under 35 U.S.C. 371 of PCT/IB2019/061126, filed Dec. 19, 2019, which was published by the International Bureau in English on Jun. 25, 2020, and which claims the benefit of U.S. Provisional Application Nos. 62/782,602, filed Dec. 20, 2018, and 62/807,056, filed Feb. 18, 2019, each of which is hereby incorporated in its entirety by reference in this application.

FIELD OF THE INVENTION

The present invention relates to compositions and methods for treating plant cells in such a way that they are more amenable to genetic transformation than untreated plant cells.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of BHP028P3 sequence listing ST25.txt, a creation date of Dec. 13, 2019, and a size of 127 Kb. The sequence listing filed via EFS-Web is part of the specification and is hereby incorporated in its entirety by reference herein.

BACKGROUND OF THE INVENTION

Plant transformation generally encompasses protocols for the introduction of one or more plant-expressible foreign gene(s) into plant cells. After this introduction, plants may be regenerated from the cell(s) into which foreign gene(s) have been introduced such that fertile progeny plants may be obtained which stably maintain and express the foreign gene. More recently developed plant transformation protocols make use of so-called "genome editing" technologies that allow for the insertion of foreign genetic material at pre-determined genomic loci, precise modification of DNA sequences at pre-determined genomic loci, and/or deletion of DNA sequences from pre-determined genomic loci. Numerous plant species have been transformed using standard transformation techniques and/or genome editing techniques. Transgenic and/or genome edited agronomic crops, as well as fruits and vegetables, are of commercial interest. Such crops include but are not limited to maize, rice, soybeans, canola, sunflower, alfalfa, sorghum, wheat, cotton, peanuts, tomatoes, potatoes, peas, and the like.

Thus, the methods of this disclosure can be used to provide transformed plants with combinations of traits that may provide benefits to growers, processors, and consumers. Methods for increasing plant transformation efficiency are provided.

SUMMARY OF THE INVENTION

Methods for increasing plant cell transformation efficiency are described. These methods include exposing the plant cells to a liquid medium containing a surfactant. Following exposure to the surfactant-containing medium, the cells become more amenable to transformation and may be genetically transformed using methods known in the art. Plant cell transformation following exposure of the cells to the surfactant-containing medium is more efficient than transformation of cells not exposed to the surfactant-containing medium.

DETAILED DESCRIPTION OF THE INVENTION

Methods to increase the transformation frequency and/or efficiency in plant cells by pre-conditioning the plant material to be transformed are described. The methods include exposing plant cells or tissues to a liquid medium containing a surfactant, then removing the surfactant-containing medium, then transforming the plant cells or tissues by methods available in the art. "Pre-conditioning" is the exposure of the plant cells to a surfactant-containing medium for a period lasting between 5 minutes and 90 minutes, followed by removal of the surfactant containing medium prior to transformation of the cells that were exposed to a surfactant-containing medium. The methods result in improved transient expression of introduced genes, enhanced production of stably transformed cells and sectors, and improved recovery of regenerated transformed plants.

"Plant cells or tissues" includes, without limitation, cells, callus, embryos, leaf discs, hypocotyl tissue, hairy roots, cotyledons, immature embryos, flowers, and other plant cells and tissues that are suitable for transformation using the methods of the invention.

Transformation of plant cells requires the introduction of the transforming DNA, for example and without limitation, by contacting the plant cells with a suitable strain of *Agrobacterium* that harbors one or more transformation plasmids. Strains of *Agrobacterium* differ from one another in their ability to transform plant cells of various species. Regardless of the particular combination of *Agrobacterium* strain/host plant considered, *Agrobacterium* acts through attachment to the host cell during transformation. See McCullen and Binns, 2006, Ann. Rev. Cell. Dev. Biol. 22:101-127; and Citovsky et al., 2007, Cell. Microbiol. 9:9-20. For this reason, methods that affect plant cell wall structure and/or the ability of plant cells to take in material such as genetic material including DNA, such as those disclosed herein using surfactants (Buchanan 1965 Iowa State University Dissertation), may produce increases in transformation efficiency.

Without being limited by theory, increases in plant transformation efficiencies by the methods disclosed herein may result from the ability of surfactants to decrease hydrophobic repulsive interactions between *Agrobacterium* cell walls and plant cell walls, and thus allow intimate cell-cell interactions to occur. Without being limited by theory, increases in plant transformation efficiency by the methods disclosed herein may also result from the ability of surfactants to modify plant cell walls, allowing for more efficient introduction of DNA into the plant cells. One may therefore utilize the chemical differences between different surfactant agents to promote plant cell wall modifications so that enhanced transformation efficiencies may be observed.

Surfactants belong to several chemical classes, and one skilled in the field of plant transformation will understand that different chemical classes of surfactants may be used to enhance plant transformation efficiency with different plant hosts. Examples of surfactants from these chemical classes useful with the methods disclosed herein include adjuvants, non-ionic surfactants, anionic surfactants, oil-based surfactants, amphoteric surfactants, and polymeric surfactants. An example of a preferred surfactant useful with the methods described herein is a non-ionic trisiloxane surfactant such as BREAK-THRU® S233 from Evonik Industries (Essen, Germany). Examples of further preferred surfactants useful with the methods described herein include trisiloxane alkoxylates, ethoxylated soybean oils, alcohol ethoxylate C-13s, $C_{12}$-$C_{14}$-alkyldimethyl betaines, and di-sec-butylphenol ethylene oxide-propylene oxide block co-polymers. Additional surfactants of various chemical types that may be used to practice the methods described herein are disclosed in U.S. patent application Ser. No. 13/715,118.

The methods disclosed herein utilize the transformation-enhancing properties of surfactants to dramatically increase transformation efficiency in plants such as immature maize embryos by *Agrobacterium* (e.g., *Agrobacterium tumefaciens*). The surfactants used with the methods described herein are selected, as suggested above, based upon the ability to modify cell wall properties in such a way that will enhance transformation efficiency. The concentration of surfactant in the liquid medium can be 0.001-0.1% (v/v), 0.001-0.09% (v/v), 0.001-0.08% (v/v), 0.001-0.07% (v/v), 0.001-0.06% (v/v), 0.001-0.05% (v/v), 0.01-0.04% (v/v), 0.001-0.03% (v/v), or 0.001-0.2% (v/v).

One or more additional surfactants can also be used with the methods described herein. As indicated, the transformation efficiency is dependent on a variety of factors including plant species and tissue-type and *Agrobacterium* strain. Given the variety of interactions involved, a system of two or more surfactants can provide enhanced transformation efficiency.

In some embodiments, the cells or tissues are exposed to the surfactant containing medium for a length of time between 5 minutes and 90 minutes. In some embodiments, the cells or tissues are exposed to the surfactant containing medium for a length of time between 5 minutes and 60 minutes. After exposure to the surfactant containing medium, the surfactant containing medium is removed by pipetting or other suitable methods that result in the removal of substantially all of the preconditioning medium and the cells or tissues are resuspended in a medium that lacks surfactant.

The methods of the invention can be used with any plant transformation protocol. Many plant transformation methods are known in the art, and for obtaining plants that stably maintain and express the introduced gene. Such techniques include biolistic transformation (e.g., U.S. Pat. Nos. 4,945,050 and 5,141,131), WHISKERS™ technology (see, e.g., U.S. Pat. Nos. 5,302,523 and 5,464,765), electroporation technology (e.g., WO 87/06614, U.S. Pat. Nos. 5,472,869, 5,384,253, WO 92/09696, and WO 93/21335), fusion of plant protoplasts with liposomes containing the DNA to be delivered, direct injection of the DNA, and introduction of foreign DNA through the use of suitable bacteria including *Agrobacterium* sp., *Ensifer* sp., *Ochrobactrum* sp., or other suitable bacterial species, may be employed. Several techniques are known for performing genome editing in plant cells including CRISPR-based genome editing techniques (for example, Cas9, Cpf1/Cas12a, Cms1/Cas12f, C2c1, C2c3, CasX, CasY, or other suitable CRISPR/Cas nuclease systems), meganucleases, TALENs, zinc finger nucleases (ZFNs), and other techniques. In some embodiments a repair donor template may be included along with the nuclease system(s) for genome editing of plant cells.

Once the inserted DNA has been integrated into the plant genome or the desired genome editing has been performed, these DNA sequence changes are usually stable throughout subsequent generations. The transformed cells grow inside the plants in the usual manner. They can form germ cells and transmit the DNA change(s) to progeny plants. Such plants can be grown in the normal manner and may be crossed with plants that have the same transformed hereditary factors or other hereditary factors. The resulting hybrid individuals have the corresponding phenotypic properties, for example, the ability to control the feeding of plant pest insects.

A number of alternative techniques can also be used for inserting DNA into a host plant cell and/or for delivering DNA that encodes nuclease(s) that can be used for genome editing (e.g., meganucleases, ZFNs, TALENs, and/or suitable CRISPR nucleases with guide RNA(s)). Those techniques include, but are not limited to, transformation with T-DNA delivered by *Agrobacterium tumefaciens* or *Agrobacterium rhizogenes* as the transformation agent and/or transformation with suitable species that may include *Rhizobium, Sinorhizobium, Ochrobactrum* and/or *Ensifer* species (see, e.g., U.S. Ser. No. 15/756,023; U.S. Pat. No. 7,888,552; WO2007/137075; WO2014/157541, WO 2006/004914). Plants may be transformed using *Agrobacterium* technology, as described, for example, in U.S. Pat. Nos. 5,177,010, 5,104,310, European Patent Application No. 0131624B1, European Patent Application No. 120516, European Patent Application No. 159418B1, European Patent Application No. 176112, U.S. Pat. Nos. 5,149,645, 5,469,976, 5,464,763, 4,940,838, 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. Nos. 5,231,019, 5,463,174, 4,762,785, 5,004,863, 5,159,135, and U.S. patent application Ser. No. 15/501,916. The use of T-DNA-containing vectors for the transformation of plant cells has been intensively researched and sufficiently described in European Patent Application 120516; An et al., (1985, EMBO J. 4:277-284); Fraley et al., (1986, Crit. Rev. Plant Sci. 4:1-46), and Lee and Gelvin (2008, Plant Physiol. 146:325-332), and is well established in the field.

A critical first step in the transformation of plant cells by *Agrobacterium* spp. or other suitable bacterial species for the transfer of DNA into plant cells is close contact, binding, or adherence of the bacterial cells to the cells of the host plant to be transformed. After cell-cell binding, the biology of T-DNA transfer from *Agrobacterium* to plant cells is known. See, e.g., Gelvin, 2003, Microbiol. Molec. Biol. Rev. 67:16-37; and Gelvin, 2009, Plant Physiol. 150:1665-1676. Without being limited by theory, transfer of T-DNA from other bacterial species may follow similar mechanisms to those understood to occur in *Agrobacterium* sp. At minimum, at least a T-DNA right border repeat, but often both the right border repeat and the left border repeat of the Ti or Ri plasmid will be joined as the flanking region of the gene(s) desired to be inserted into the recipient plant cell's genome. The left and right T-DNA border repeats are crucial cis-acting sequences required for T-DNA transfer. Typically, left and right T-DNA border repeats are derived from naturally occurring plasmids derived from *Agrobacterium* species, but suitable synthetic T-DNA border sequences (sometimes referred to as P-DNA sequences) may also be used (see, e.g., Rommens et al. (2005) Plant Physiol 139:1338-1349; U.S. Pat. Nos. 7,250,554; 7,534,934; 7,601,536; 7,619,138; 7,880,057). Various trans-acting components are encoded within the total *Agrobacterium* genome. Primary amongst these are the proteins encoded by the vir genes, which are normally found as a series of operons on the Ti or Ri plasmids. Various Ti and Ri plasmids differ somewhat in the complement of vir genes, with, for example, virF not always being present. Proteins encoded by vir genes perform many different functions, including recognition and signaling of plant cell/bacteria interaction, induction of vir gene transcription, formation of a Type IV secretion channel, recognition of T-DNA border repeats, formation of T-strands, transfer of T-strands to the plant cell, import of the T-strands into the plant cell nucleus, and integration of T-strands into the plant nuclear chromosome, to name but a few. See, e.g., Tzfira and Citovsky, 2006, Curr. Opin. Biotechnol. 17:147-154.

If *Agrobacterium* strains are used for transformation, the DNA to be inserted into the plant cell can be cloned into special plasmids, for example, either into an intermediate (shuttle) vector or into a binary vector. Intermediate vectors are not capable of independent replication in *Agrobacterium* cells, but can be manipulated and replicated in common *Escherichia coli* molecular cloning strains. It is common that such intermediate vectors comprise sequences, framed by the right and left T-DNA border repeat regions, that may include, e.g., a selectable marker gene functional for the selection of transformed plant cells, a cloning linker, cloning polylinker, or other sequence that can function as an introduction site for genes destined for plant cell transformation. Cloning and manipulation of genes desired to be transferred to plants can thus be easily performed by standard molecular biology techniques in *E. coli* cells, using the shuttle vector as a cloning vector. The shuttle vector can subsequently be introduced into suitable *Agrobacterium* plant transformation strains, or suitable strains of alternative bacterial species that may be used for plant transformation, for further work. The intermediate vector can be transferred into *Agrobacterium* or into the cells of other suitable bacterial species that may be used for plant transformation by means of a helper plasmid (via bacterial conjugation), by electroporation, by chemically mediated direct DNA transformation, or by other methods. Shuttle vectors can be integrated into the Ti or Ri plasmid or derivatives thereof by homologous recombination owing to sequences that are homologous between the Ti or Ri plasmid, or derivatives thereof, and the intermediate plasmid. This homologous recombination (i.e. plasmid integration) event thereby provides a means of stably maintaining the altered shuttle vector in *Agrobacterium*, with an origin of replication and other plasmid maintenance functions provided by the Ti or Ri plasmid portion of the co-integrant plasmid. The Ti or Ri plasmid also comprises the vir regions comprising vir genes necessary for the transfer of the T-DNA. It is common that the plasmid carrying the vir region is a mutated Ti or Ri plasmid (helper plasmid) from which the T-DNA region, including the right and left T-DNA border repeats, have been deleted, though this plasmid may also be fully synthetic. Such pTi-derived plasmids, having functional vir genes and lacking all or substantially all of the T-region and associated elements are descriptively referred to herein as helper plasmids.

The superbinary system is a specialized example of the shuttle vector/homologous recombination system (reviewed by Komari et al., 2006, In: Methods in Molecular Biology (K. Wang, ed.) No. 343: *Agrobacterium* Protocols, pp. 15-41; and Komori et al., 2007, Plant Physiol. 145:1155-1160). Strain LBA4404(pSB1) harbors two independently-replicating plasmids, pAL4404 and pSB1. pAL4404 is a Ti-plasmid-derived helper plasmid which contains an intact set of vir genes (from Ti plasmid pTiACH5), but which has no T-DNA region (and thus no T-DNA left and right border repeat sequences). Plasmid pSB1 supplies an additional partial set of vir genes derived from pTiBo542; this partial vir gene set includes the virB operon and the virC operon, as well as genes virG and virD1. One example of a shuttle vector used in the superbinary system is pSB11, which contains a cloning polylinker that serves as an introduction site for genes destined for plant cell transformation, flanked by Right and Left T-DNA border repeat regions. Shuttle vector pSB11 is not capable of independent replication in *Agrobacterium*, but is stably maintained as a co-integrant plasmid when integrated into pSB1 by means of homologous recombination between common sequences present on pSB1 and pSB11. Thus, the fully modified T-DNA region introduced into LBA4404(pSB1) on a modified pSB11 vector is productively acted upon and transferred into plant cells by Vir proteins derived from two different *Agrobacterium* Ti plasmid sources (pTiACH5 and pTiBo542). The *Agrobacterium tumefaciens* host strain employed with the superbinary system is LBA4404(pSB1). The superbinary system has proven to be particularly useful in transformation of monocot plant species. See Hiei et al., (1994) Plant J. 6:271-282; and Ishida et al., (1996) Nat. Biotechnol. 14:745-750.

In addition to the vir genes harbored by *Agrobacterium* Ti plasmids, other, chromosomally-borne virulence controlling genes (termed chv genes) are known to control certain aspects of the interactions of *Agrobacterium* cells and plant cells, and thus affect the overall plant transformation frequency (Pan et al., 1995, Molec. Microbiol. 17:259-269). Several of the chromosomally-borne genes required for virulence and attachment are grouped together in a chromosomal locus spanning 29 kilobases (Matthysse et al., 2000, Biochim. Biophys. Acta 1490:208-212).

In addition to numerous technologies for transforming plants, the type of tissue which is contacted with the foreign genes may vary as well. Such tissue may include, but is not limited to, embryogenic tissue, callus tissue types I and II, hypocotyl, and meristem tissues. Almost all plant tissues may be transformed during dedifferentiation using appropriate techniques understood by a person of ordinary skill in the art. One of ordinary skill in the field of plant transformation will understand that multiple methodologies are available for the production of transformed plants, and that they may be modified and specialized to accommodate biological differences between various host plant species or plant tissues. Plant explants (for example, pieces of leaf, segments of stalk, meristems, roots, protoplasts and/or suspension-cultivated cells) can advantageously be cultivated with suitable bacterial species, or may be transformed using other technologies (e.g., biolistic transformation, WHISKER-mediated transformation, or other transformation methods) for the transfer of the DNA into the plant cell.

Callus Cultures

Plant tissue cultures may advantageously be cultivated with a suitable bacterial species including, for example, *Agrobacterium tumefaciens* or *Agrobacterium rhizogenes*, for the transfer of the DNA into the plant cell, and are generally initiated from sterile pieces of a whole plant that may consist of pieces of organs, such as leaves or roots, or from specific cell types, such as pollen or endosperm. Many features of the explant are known to affect the efficiency of culture initiation, and the efficiency of culture initiation may also be affected by the composition of tissue culture medium, light intensity, temperature, humidity, or other environmental conditions. It is thought that any plant tissue can be used as an explant, if the correct conditions are found. Generally, younger, more rapidly growing tissue (or tissue at an early stage of development) is most effective for callus initiation. Explants cultured on the appropriate medium can give rise to an unorganized, growing, and dividing mass of cells (callus). In culture, callus can be maintained more or less indefinitely, provided that it is subcultured on to fresh medium periodically. During callus formation, there is some degree of de-differentiation, both in morphology (a callus is usually composed of unspecialized parenchyma cells) and metabolism.

Callus cultures are extremely important in plant biotechnology. Manipulation of the plant hormone ratios in the culture medium can lead to the development of shoots, roots, or somatic embryos from which whole plants can subsequently be produced (regeneration). Callus cultures can also be used to initiate cell suspension cultures that may be used to study plant transformation, gene regulation, and other aspects of plant growth and development.

Cell Suspension Cultures

Callus cultures can typically be classified into one of two categories: compact or friable. In compact callus, the cells are densely aggregated, while in friable callus, the cells are only loosely associated with each other and the callus becomes soft and breaks apart easily. Friable callus provides the inoculum to develop cell-suspension cultures. Explants from some plant species or particular cell types tend not to form friable callus, particularly when cultured under conditions that do not promote the production of friable callus, making it difficult to initiate cell suspension cultures. The friability of the callus can sometimes be improved by manipulating the medium components, by repeated subculturing, and/or by culturing it on semi-solid medium (medium with a low concentration of gelling agent). When friable callus is placed into a liquid medium and agitated, single cells and/or small clumps of cells are released into the medium. Under certain conditions, these released cells continue to grow and divide, eventually producing a cell-suspension culture. Cell suspensions can be maintained relatively simply as batch cultures in conical flasks and can be propagated by repeated subculturing into fresh liquid tissue culture medium. After subculture, the cells continue to divide and the biomass of the culture increases as a result. Cell suspension cultures may advantageously be cultivated with, for example, *Agrobacterium tumefaciens, Agrobacterium rhizogenes*, or other suitable bacterial species capable of transferring DNA into the plant cell, or may be transformed using other suitable techniques.

Shoot Tip and Meristem Culture

The tips of shoots (which contain the shoot apical meristem) can be cultured in vitro, producing clumps of shoots from either axillary or adventitious buds and may advantageously be cultivated with, for example, *Agrobacterium tumefaciens, Agrobacterium rhizogenes*, or other suitable bacterial species that may be used for the transfer of the DNA into the plant cell, or may be transformed using other suitable techniques known in the art. Shoot meristem cultures may used for cereal regeneration; seedlings can be used as donor material.

Embryo Culture

Embryos can be used as explants to generate callus cultures or somatic embryos. Immature or mature embryos may be used as explants for callus generation. Immature, embryo-derived embryogenic callus is a tissue often used in monocotyledon plant tissue culture regeneration and may advantageously be cultivated with, for example, *Agrobacterium tumefaciens, Agrobacterium rhizogenes*, or other suitable bacterial species that may be used for the transfer of the DNA into the plant cell, or may be transformed using other suitable techniques. Immature embryos are an intact tissue that is capable of cell division to give rise to callus cells that can differentiate to produce tissues and organs of a whole plant. Immature embryos can be obtained from the fertilized ears of a mature maize plant, for example, from plants pollinated using the methods of Neuffer et al. (1982, Growing maize for genetic purposes. In: Maize for Biological Research. W. F. Sheridan, Ed. UNIVERSITY PRESS, University of North Dakota, Grand Forks, N. Dak.). Exemplary methods for isolating immature embryos from maize are described by Green and Phillips (Crop Sci. 15:417-421 (1976)). Immature embryos are preferably isolated from the developing ear using aseptic methods and are held in sterile medium until use. The use of *Agrobacterium* in transformation of immature embryos is disclosed by Sidorov & Duncan, (2009, Methods in Molecular Biology: Transgenic Maize, vol. 526 Chapter 4, M. Paul Scott (Ed.)) and in U.S. Pat. No. 5,981,840.

Microspore Culture

Haploid tissue can be cultured in vitro for example by using pollen or anthers as an explant and may advantageously be cultivated with, for example, *Agrobacterium tumefaciens, Agrobacterium rhizogenes*, or other suitable bacterial species that may be used for the transfer of the DNA into the plant cell, or may be transformed using other suitable techniques. Both callus and embryos can be produced from pollen. At least two approaches can be taken to produce cultures in vitro from haploid tissue. In the first, anthers (somatic tissue that surrounds and contains the pollen) are cultured on solid tissue culture medium. Pollen-derived embryos are subsequently produced via dehiscence of the mature anthers. The dehiscence of the anther depends both on its isolation at the correct stage and on the correct culture conditions. In some species, the reliance on natural dehiscence can be circumvented by cutting the wall of the anther. In the second method, anthers are cultured in liquid medium, and pollen released from the anthers can be induced to form embryos. Immature pollen can also be extracted from developing anthers and cultured directly.

Many of the cereals (rice, wheat, barley, and maize) require medium supplemented with plant growth regulators for pollen or anther culture. Regeneration from microspore explants can be obtained by direct embryogenesis, or via a callus stage and subsequent embryogenesis.

Haploid tissue cultures can also be initiated from the female gametophyte (the ovule). In some cases, this may be a more efficient method than using pollen or anthers.

Plants obtained from haploid cultures may not be haploid as a result of chromosome doubling during the culture period. Chromosome doubling (which may be induced by treatment with, for example, chemicals such as colchicine) may be an advantage, as in many cases haploid plants are not the desired outcome of regeneration from haploid tissues. Such plants are often referred to as di-haploids, because they contain two copies of the same haploid genome.

Following transformation of any of the aforementioned plant materials by cultivation with *Agrobacterium tumefaciens* or another suitable bacterial species for the transfer of the DNA into the plant cell, and/or following other transformation methods, whole plants may then be regenerated from the transformed plant material following placement in suitable growth conditions and culture medium. The regeneration medium may contain antibiotics and/or herbicides, as appropriate, for selection of the transformed plant cells, depending on the presence of selectable marker genes that impart resistance or tolerance to such selective agents (i.e., antibiotics and/or herbicides). The plants so obtained can then be tested for the presence of the inserted DNA.

Cell transformation (including plant cell transformation) may involve the construction of an expression vector which will function in a particular cell. Such a vector may comprise DNA that includes a gene under control of, or operatively linked to, a regulatory element (for example, a promoter) that is operable in a plant cell. The expression vector may contain one or more such operably-linked gene/regulatory element combinations. The vector(s) may be in the form of at least one plasmid and can be used alone or in combination with other plasmids to provide transformed cells using transformation methods as described herein to incorporate transgene(s) into the genetic material of a plant cell.

Plant cell expression vectors may include at least one genetic marker (alternately referred to as a "selectable marker gene"), operably linked to a regulatory element (a promoter, for example) that allows transformed cells containing the marker to be recovered either by negative selection (i.e., inhibiting growth of cells that do not contain the selectable marker gene) or by positive selection (i.e., screening for the product encoded by the genetic marker). Many selectable marker genes suitable for plant transformation are well known in the art and include, for example, genes that encode enzymes that metabolically detoxify a selective chemical agent such as, for example, an antibiotic or an herbicide, or genes that encode an altered target which may be insensitive to the inhibitor. Positive selection methods are also known in the art. The individually employed selectable marker gene may accordingly permit the selection of transformed cells while the growth of cells that do not contain the inserted DNA can be suppressed by the selective compound. Different selectable marker gene(s) and selection methods may be employed for the transformation of different plant species, different tissues, or for the purposes of modifying plant transformation efficiencies, for example. Examples of suitable selectable markers include, but are not limited to, resistance or tolerance to Kanamycin, G418, Hygromycin, Bleomycin, Methotrexate, Phosphinothricin (Bialaphos), Glyphosate, Imidazolinones, Sulfonylureas and Triazolopyrimidine herbicides, such as Chlorosulfuron, Bromoxynil, and DALAPON.

In addition to a selectable marker, it may be desirable in some embodiments to use a reporter gene. In some embodiments a reporter gene may be used without a selectable marker (i.e., through visual selection alone by inspection for presence of the reporter gene-encoded product rather than through the use of a positive or negative selection technique). Reporter genes are genes which typically do not provide a growth advantage to the recipient organism or tissue. The reporter gene typically encodes for a protein which provides for some phenotypic change or enzymatic property. Some commonly used suitable reporter genes include, but are not limited to, those that encode beta-glucuronidase (GUS), luciferase, or fluorescent proteins such as green fluorescent protein (GFP), yellow fluorescent protein (YFP, essentially as disclosed in U.S. Pat. No. 7,951,923), or other fluorescent proteins.

Typically, following the introduction of the gene(s) to expressed in the plant cell, three phases may be observed. In the first phase, the inserted gene(s) are transiently expressed, though they may not be stably inserted into the genome of the recipient cell. This transient expression may result from expression of the introduced DNA, though integration of the DNA into the recipient cell genome may not have yet occurred. In some embodiments, this first phase may last for up to 24 hours, up to 48 hours, up to 72 hours, up to 96 hours, or up to one week following transformation. A second phase may be observed on tissue culture medium during which stable sectors of transformed plant cells are formed. These stable sectors comprise dividing cells in which the introduced gene(s) have been stably inserted into the genome. Expression of the introduced gene(s) continues after the introduced DNA has been cleared as a result of the normal replication of the cellular DNA. The stable sectors will continue to divide and grow and may produce shoots. In some embodiments, shoot production may be stimulated for example by the addition of suitable chemicals such as plant hormones. Following shoot production, a third phase begins during which stably transformed plants are regenerated from transformed plant cells. Regenerated plants may be grown on suitable tissue culture medium and may produce roots, leaves, and other organs. Typically, regenerated plants are transferred to soil for continued cultivation in, for example, a greenhouse or other suitable environment.

Regardless of the transformation technique utilized, the gene(s) to be inserted into the genome of the recipient plant cell, and/or to be expressed in the recipient plant cell, can be incorporated into a gene transfer vector adapted to express the foreign gene in the plant cell by including in the vector a promoter that is operable in a plant cell. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), a promoter from sugarcane bacilliform virus, and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters.

Promoters may also contain certain enhancer sequence elements that may improve the transcription efficiency. Typical enhancers include, but are not limited to, alcohol dehydrogenase 1 (ADH1) intron 1 and ADH1-intron 6. Constitutive promoters, which direct continuous gene expression in nearly all cells types and at nearly all times (e.g. actin, ubiquitin, CaMV 35S), may also be used. Tissue specific promoters are responsible for gene expression in specific cell or tissue types, such as the leaves or seeds. Examples of other promoters that may be used include those that are active during a certain stage of the plant's development, as well as active in specific plant tissues and organs. Examples of such promoters include, but are not limited to, promoters that are root specific, pollen-specific, embryo specific, corn silk specific, cotton fiber specific, seed endosperm specific, and phloem specific.

Under certain circumstances, it may be desirable to use an inducible promoter. An inducible promoter is responsible for expression of genes in response to a specific signal, such as physical stimulus (e.g. heat shock genes); light (e.g. Ribulose-bis-phosphate 1,5 carboxylase); hormone (e.g. glucocorticoid) accumulation; antibiotic (e.g. Tetracycline); metabolites; and stress (e.g. drought). Other desirable transcription and translation elements that function in plants also may be used, such as, for example, 5' untranslated leader sequences, and 3' RNA transcription termination and polyadenylate addition signal sequences. Any suitable plant-specific gene transfer vector may be used.

Transgenic crops containing insect resistance (IR) traits are prevalent in commercially grown crop plant species, as are crops containing herbicide tolerance (HT) traits. Commercial transgenic crops combining IR and herbicide tolerance (HT) traits are also widely grown. These include combinations of IR traits conferred by *Bacillus thuringiensis* (B.t.) insecticidal proteins and HT traits such as tolerance to Acetolactate Synthase (ALS) inhibitors such as Sulfonylureas, Imidazolinones, Triazolopyrimidine, Sulfonanilides, and the like, Glutamine Synthetase (GS) inhibitors such as Bialaphos, Glufosinate, and the like, 4-HydroxyPhenylPyruvate Dioxygenase (HPPD) inhibitors such as Mesotrione, Isoxaflutole, and the like, 5-EnolPyruvylShikimate-3-Phosphate Synthase (EPSPS) inhibitors such as Glyphosate and the like, and Acetyl-Coenzyme A Carboxylase (ACCase) inhibitors such as Haloxyfop, Quizalofop, Diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005/107437A1). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein with one or more additional HT traits such as those mentioned above, plus one or more additional input traits (e.g. other insect resistance conferred by B.t.-derived or other insecticidal proteins, insect resistance conferred by mechanisms such as RNAi and the like, disease resistance, stress tolerance, improved nitrogen utilization, and the like), or output traits (e.g. high oils content, healthy oil composition, nutritional improvement, and the like). Such combinations may be obtained through, e.g., conventional breeding (e.g. a breeding stack), and/or jointly as a novel transformation event involving the simultaneous introduction of multiple genes (e.g. a molecular stack), and/or through genome editing methods that allow for the insertion of genes at a pre-determined location in the genome of the target cell or organism. Benefits include the ability to manage insect pests and improved weed control in a crop plant that provides secondary benefits to the producer and/or the consumer.

Genetic modification of crop plants may also be used to provide additional benefits to the plant. Such benefits may include, without limitation, modified flavor profiles, modified amino acid content and/or quality, modified total protein content and/or quality, modified oil content and/or quality, altered color, improved resistance to abiotic stresses such as heat, drought, cold, and/or flooding, improved post-harvest shelf stability, improved digestibility, and/or other desirable traits.

The methods described herein are broadly applicable to a variety of plant species and varieties including monocotyledons and dicotyledons. Crops of interest include but are not limited to corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), pea (*Pisum sativum*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), quinoa (*Chenopodium quinoa*), chicory (*Cichorium intybus*), lettuce (*Lactuca sativa*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers. The methods herein can be used with cells at various stages of development, e.g., immature embryos. Thus, the methods described herein can be used to transform maize immature embryos. The size of immature embryos used in conjunction with the methods described herein can vary. For example, immature embryos can be greater than or equal to 1.5 mm and less than or equal to 2.5 mm in length.

The external environment the cells are maintained in after transformation according to the methods described herein can be controlled. For example, temperature, pH, and the components in the growth medium (e.g., salts and/or plant hormones) the cells are exposed to after transformation according to the methods described herein are varied. One of those variables is the amount of light the cells are exposed to. The methods described herein can include exposing the plant cells to common 18 hour light/6 hour dark protocols or alternatively to continuous light after transformation. For example, cells treated according to the methods described herein can be exposed to 24-hour white fluorescent light conditions for weeks after treatment, e.g., until the regeneration and/or plantlet isolation stages of plant preparation.

An additional method includes preparing a liquid medium containing a surfactant, exposing plant cells to the surfactant-containing medium, and then removing the surfactant-containing medium prior to transformation. The surfactant-treated plant cells are referred to as "pre-conditioned" cells and are more amenable to transformation than cells that are not pre-conditioned.

Protocols and methods for transforming plants include, for example and without limitation, transformation by *Agrobacterium* species (e.g., *A. tumefaciens* or *A. rhizogenes*) or other suitable bacterial species (e.g., *Ensifer* species or Ochrobactrum species), or transformation by biolistic methods or other methods. Any method useful for plant transformation can be employed in conjunction with the methods described herein. The examples below provide embodiments of methods demonstrating the effectiveness of the methods described herein, but are not intended to be limitations on the scope of the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Embodiments of the invention include:
1. A method of improving transformation of plant cells comprising:
    i) pre-conditioning plant cells by exposure to a surfactant containing medium,
    ii) removing said plant cells from said surfactant containing medium, and
    iii) introducing at least one polynucleotide sequence into said plant cells.
2. The method of embodiment 1, wherein said surfactant containing medium comprises a non-ionic surfactant.
3. The method of embodiment 1, wherein said surfactant containing medium comprises a surfactant selected from the group consisting of Break-Thru S233, Break-Thru S240, Break-Thru S279, Break-Thru S301, and Pluronic F-68.
4. The method of embodiment 1, wherein said surfactant containing medium comprises surfactant at a concentration of 0.001-0.1% (v/v).
5. The method of embodiment 1 wherein said exposure to a surfactant containing medium lasts for 5-60 minutes.
6. The method of embodiment 1 wherein said introducing one or more polynucleotide sequence(s) includes the use of *Agrobacterium* cells harboring a plant transformation construct.
7. The method of embodiment 6 wherein said *Agrobacterium* cells harboring a plant transformation construct comprise a binary vector.
8. The method of embodiment 6 wherein said *Agrobacterium* cells harboring a plant transformation construct comprise a superbinary vector.
9. The method of embodiment 1 wherein said improving transformation of plant cells comprises an increased percentage of plant cells exhibiting transient expression of said at least one polynucleotide sequence relative to control plant cells not exposed to said surfactant containing medium.
10. The method of embodiment 1 wherein said improving transformation of plant cells comprises an increased percentage of callus pieces developing stably transformed sectors.
11. The method of embodiment 1 wherein said improving transformation of plant cells comprises an increased number of transformed plants regenerated from transformed tissue.
12. The method of embodiment 1 wherein said plant cells are derived from a monocot.
13. The method of embodiment 12 wherein said plant cells are derived from *Zea mays, Oryza sativa, Setaria viridis, Sorghum bicolor, Triticum aestivum,* or *Saccharum* sp.
14. The method of embodiment 1 wherein said plant cells are derived from a dicot.
15. The method of embodiment 14 wherein said plant cells are derived from *Pisum sativum, Lactuca sativa,* or *Solanum lycopersicum*.
16. The method of embodiment 1 wherein said at least one polynucleotide sequence comprises a polynucleotide sequence that shares at least 80% sequence identity with a sequence selected from the group of sequences consisting of SEQ ID NOs:1 and 15, or that encodes a protein that shares at least 80% sequence identity with a sequence selected from the group of sequences consisting of SEQ ID NOs:2 and 16.
17. The method of embodiment 1 wherein said at least one polynucleotide sequence comprises a polynucleotide sequence that shares at least 80% sequence identity with a sequence selected from the group of sequences consisting of SEQ ID NOs:3, 5, and 7, or that encodes a protein that shares at least 80% sequence identity with a sequence selected from the group of sequences consisting of SEQ ID NO:4, 6, and 8.
18. The method of embodiment 1 wherein said introducing at least one polynucleotide sequence comprises biolistic transformation.
19. The method of embodiment 1 wherein said at least one polynucleotide sequence encodes at least one CRISPR nuclease.
20. The method of embodiment 19 wherein said preconditioning results in improved genome editing relative to control cells not exposed to said surfactant containing medium.

The following examples are offered by way of illustration and not by way of limitation.

EXPERIMENTAL

Example 1—Maize Transformation Materials and Embryo Isolation

Plant Materials and Embryo Isolation

*Zea mays* (B 104) plants were grown in the greenhouse under 50% metal halide, 50% high pressure sodium lights (14 h daylength, 28° C. day/22° C. night, 40-50% minimum relative humidity). The plants were self-pollinated and produced ears suitable for embryo transformation. Ten to thirteen days after pollination, ears were harvested and surface-sterilized in a 20% (v/v) solution of household bleach containing 0.05% (v/v) Tween 20 for 20 minutes while stirring. Following bleach sterilization, the ears were rinsed in sterile water 3-5 times for 5 min/each rinse Immature zygotic embryos (1.8-2.2 mm) were aseptically isolated from each ear and randomly distributed into micro-centrifuge tubes containing liquid infection media (MS salts, 4.33 gm/L; MS modified Vitamin Solution (Phytotechnology M557) [1000×], 1.00 mL/L; L-proline, 700.0 mg/L; sucrose, 68.5 gm/L; glucose, 36.0 gm/L; 2,4-D, 1.50 mg/L) and the pH was adjusted to 5.2.

*Agrobacterium* Culture Initiation

Glycerol stocks of *Agrobacterium* containing the appropriate vectors were stored at −80° C. until ready to use. A loop from the frozen glycerol was streaked on AB minimal medium plates containing appropriate antibiotics for plasmid maintenance and plates were grown at 20-25° C. for 3 days in the dark. A single colony was then picked and streaked onto YEP plate containing the same antibiotics and was incubated at 28° C. for 1-3 days.

*Agrobacterium* Culture

On the day of the experiment, *Agrobacterium* colonies were taken from the YEP plate, suspended in 10-15 mL of infection medium in a 50 mL disposable tube, and the cell density adjusted to OD600=0.2-0.4 nm for AGL1 *Agrobacterium* harboring binary vector 131440 (SEQ ID NO:9) and 0.8-1.1 for LBA4404 *Agrobacterium* harboring superbinary vector 130571 (SEQ ID NO:10). *Agrobacterium* cultures were then placed on a rotary shaker at 120-130 rpm, room temperature, while embryos dissection was performed.

Preconditioning Treatment

For the preconditioning treatment, 0.1-0.5% (v/v) of surfactant was added to infection media. Immature zygotic embryos between 1.8-2.2 mm in size were isolated and pooled from the sterilized maize kernels and placed either in 1.75 mL of the infection medium alone or in infection media comprising the appropriate surfactant ("preconditioning medium"). The preconditioning treatment lasted between 5 min-60 min and was performed at room temperature. After all embryos were isolated and preconditioned, the preconditioning media was removed by pipetting from the embryos and discarded.

Agrobacterium Infection and Co-Cultivation

Following pre-conditioning, 1.75 ml of *Agrobacterium* suspension diluted to the appropriate OD600 concentration was added to each tube. Tubes were then inverted to mix and placed on rocker shaker for 10-15 min at room temperature. Infected embryos were transferred onto co-cultivation media (MS salts, 4.33 gm/L; MS modified Vitamin Solution (Phytotechnology M557) [1000×], 1.00 mL/L; L-proline, 700.0 mg/L; casein enzymatic hydrolysate 100.0 mg/L, Dicamba 3.0 mg/L; sucrose, 30.0 gm/L; Gelzan™, 2.00 gm/L; AgNo$_3$, 15.0 mg/L; Acetosyringone, 200 µM), and pH adjusted to 5.6. Infected embryos were oriented with the scutellum facing up, and incubated for 3-5 days in 24 hr light (50 µmol m$^2$s$^{-1}$) at 25° C.

Callus Selection and Regeneration of Putative Events

Following the co-cultivation period, embryos were transferred to resting media (MS salts, 4.33 gm/L; MS modified Vitamin Solution (Phytotechnology M557) [1000×], 1.00 mL/L; L-proline, 700.0 mg/L; MES, 500.0 mg/L; casein enzymatic hydrolysate 100.0 mg/L; Dicamba, 3.0 mg/L; sucrose. 30.0 gm/L; Gelzan™ 2.0 gm/L; AgNo$_3$, 15.0 mg/L; Cefotaxime, 250.0 mg/L) without selective agent and incubated in the light for 7-10 days at 27° C. Embryos were then transferred onto Selection 1 media (MS salts, 4.33 gm/L; MS modified Vitamin Solution (Phytotechnology M557) [1000×], 1.00 mL/L; L-proline, 700.0 mg/L, MES 500.0 mg/L; casein enzymatic hydrolysate 100.0 mg/L; Dicamba, 3.0 mg/L; sucrose, 30.0 gm/L; Gelzan™ 2.0 gm/L; AgNO$_3$, 15.0 mg/L; Cefotaxime, 250.0 mg/L) containing 3-5 mg/L bialaphos or 100-130 mg/l paramomycin with pH adjusted to 5.8. Plates were incubated under 24 hours light with light intensity of 50 µmol m$^2$s$^{-1}$ for 7-14 days at 27° C.

Embryos with proliferating embryogenic calli were then transferred onto Selection 2 media (MS salts, 4.33 gm/L; MS modified Vitamin Solution (Phytotechnology M557) [1000×], 1.00 mL/L, L-proline, 700.0 mg/L, MES 500.0 mg/L, casein enzymatic hydrolysate 100.0 mg/L; Dicamba, 3.0 mg/L; sucrose, 30.0 gm/L; Gelzan™ 2.0 gm/L; AgNo$_3$, 15.0 mg/L; Cefotaxime, 250.0 mg/L) and containing 3-5 mg/L bialaphos or 100-130 mg/l paramomycin with pH adjusted to 5.8. Plates were incubated under 24 hours light with light intensity of 50 µmol m$^2$s$^{-1}$ for 14 days at 27° C. This selection step allows transgenic callus to further proliferate and differentiate. The callus selection period lasted three to four weeks. Embryogenic callus was transferred onto Regeneration 1 media (MS salts, 4.33 gm/L; MS modified Vitamin Solution (Phytotechnology M557) [1000×], 1.00 mL/L; L-proline, 350.0 mg/L, MES, 250.0 mg/L; casein enzymatic hydrolysate 50.0 mg/L, NAA 0.500 mg/L; ABA 2.00 mg/L; BA 1.50 mg/L; sucrose, 45.0 gm/L; Gelzan™, 2.0 gm/L; AgNo$_3$, 1.00 mg/L; Cefotaxime, 125.0 mg/L) and containing 3-5 mg/L bialaphos or 100-130 mg/l paramomycin with pH adjusted to 5.7, and cultured for 4-7 days at 27° C. under the same light regime Calli with shoot buds were transferred onto Regeneration 2 media in phytatrays (MS salts, 4.33 gm/L; MS modified Vitamin Solution (Phytotechnology M557) [1000×], 1.00 mL/L; sucrose, 60.0 gm/L; Gelzan™ 2.3 gm/L; Cefotaxime, 125.0 mg/L) and containing 3-5 mg/L, bialaphos or 100-130 mg/l paramomycin. The cultures were incubated under 24 hours light with light intensity of 50 µmol m$^2$s$^{-1}$ for 14-21 days at 27° C. Plantlets with roots were transferred to plant robusting media (MS salts, 4.33 gm/L (Sigma-Aldrich, St. Louis, Mo.); MS modified Vitamin Solution (Phytotechnology M557) [1000×], 1.00 mL/L; myo-Inositol 100 mg/L sucrose, 30.0 gm/L; Gelzan™, 2.00 gm/L; Cefotaxime, 100.0 mg/L) and Gelzan™, 2.0 gm/L in phytatrays (Sigma-Aldrich, St. Louis, Mo.), with pH adjusted to 5.7. Cultures were incubated under 16/8 hours light 90-120 µmol m$^2$s$^{-1}$/dark for 7 days at 27° C. DNA was isolated from 30-50 mg leaf tissue from transgenic plantlets for molecular analysis.

Example 2—Methods for Quantifying GFP Expression

Transient GFP expression was observed in transformed tissues 2-5 days after co-cultivation with *Agrobacterium*. The tissues were observed under a stereomicroscope using NIGHTSEA Fluorescence Leica EZ4 Adapter which includes a Royal Blue light source (440-460 nm) and 2 filter sets for GFP (500 nm longpass or 500-560 nm green only bandpass).

GFP transient expression was evaluated using two methods, as described below.

1) PerkinElmer Plate Reader

Randomly selected tissues from different treatments were sampled and placed into a 96 well strip plate. Multiple replicates of each treatment were included in the same plate. The plate was inserted into EnSpire Multimode Plate Reader 2300 (PerkinElmer, Turku, Finland). The plate reader was designed for top fluorescence absorbance and scanning. The protocol was optimized for Monochromator absorbance cutoff 230 The excitation wavelength was set to 488 nm and emission wavelength to 510 nm. The measurement height was at 9.5 mm. The flash power was at 100% and number of flashes and flashes integrated were 100 (Manual for Multimode Detection, PerkinElmer). PerkinElmer EnSpire software converts GFP fluorescence absorbance readings to emission numbers, reported as relative fluorescence units or RFUs.

2) Relative GFP Expression in all Tissues

A visual scoring scale procedure was developed for rating GFP expression in each infected tissue after coculture with *Agrobacterium*. Tissues were scored on a scale from 0-3, with a score of 0 representing no apparent GFP expression and a score of 3 representing the strongest GFP expression. Plates containing transformed tissues were observed under stereomicroscope using a GFP filter as described above.

Example 3—Transient GFP Expression in Maize Following Binary Vector Transformation Transient expression of GFP was measured following co-cultivation of maize tissue with AGL1 *Agrobacterium* cells harboring binary vector 131440. The effect of preconditioning medium comprising 0.01% (v/v) Break-Thru 5233 was tested. Background fluorescence levels were calculated from fluorescence measurements of eight untransformed immature embryos. Twenty-four immature embryos were selected at random from 1) the group of immature embryos that were pre-conditioned with Break-Thru S233 and 2) the group of immature embryos that were not pre-conditioned. Table 1 shows the results of quantification of this transient GFP expression.

TABLE 1

Transient GFP expression after 131440 co-cultivation in experiment ZM2

| | background | untreated | pre-conditioned |
|---|---|---|---|
| | 3207 | 4394 | 61207 |
| | 2834 | 3842 | 58912 |
| | 1712 | 2187 | 49496 |
| | 1062 | 1913 | 30588 |
| | 543 | 1866 | 28044 |
| | 513 | 1713 | 22197 |
| | 314 | 1398 | 20774 |
| | 305 | 1366 | 19936 |
| | | 990 | 19891 |
| | | 987 | 19075 |
| | | 910 | 19013 |
| | | 748 | 12197 |
| | | 667 | 9467 |
| | | 662 | 8689 |
| | | 516 | 8617 |
| | | 485 | 6445 |
| | | 483 | 4390 |
| | | 467 | 2298 |
| | | 428 | 1508 |
| | | 347 | 1109 |
| | | 294 | 585 |
| | | 283 | 576 |
| | | 219 | 552 |
| | | 187 | 469 |
| Average | 1311.2 ± 1156.9 | 1139.6 ± 1089.5 | 16918.1 ± 17962.7 |
| Avg. + 3XStDev | | | 4782.1 |

Immature embryos were scored as positive for GFP expression if a fluorescence value higher than three standard deviations above background values was observed.

Table 1 shows that none of the 24 untreated embryos were scored as positive, while 16 of the 24 pre-conditioned embryos were scored as positive for transient GFP expression. While the standard deviations were quite large for the fluorescence values, this is an expected result because both GFP-expressing and non-expressing immature embryos were assessed as a result of the random choice of embryos for testing. These results show a substantial improvement in transient GFP expression in maize immature embryos resulting from the Break-Thru 5233 pre-conditioning treatment following co-cultivation with *Agrobacterium* harboring a binary vector.

Example 4—Transient GFP Expression in Maize Following Superbinary Vector Transformation Transient expression of GFP was measured following co-cultivation of maize tissue with LBA4404 *Agrobacterium* cells harboring superbinary vector 130571. The effect of pre-conditioning medium comprising 0.01% (v/v) Break-Thru S233 was tested. Background fluorescence levels were calculated from fluorescence measurements of eight untransformed immature embryos. Twenty-four immature embryos were selected at random from 1) the group of immature embryos that were pre-conditioned with Break-Thru 5233 and 2) the group of immature embryos that were not pre-conditioned. Table 2 shows the results of quantification of this transient GFP expression.

TABLE 2

Transient GFP expression after 130571 co-cultivation in experiment ZM1

| | background | untreated | pre-conditioned |
|---|---|---|---|
| | 2935 | 6814 | 129592 |
| | 1439 | 2160 | 77719 |
| | 1005 | 1924 | 30006 |
| | 950 | 1230 | 10001 |
| | 359 | 914 | 7261 |
| | 178 | 781 | 6527 |
| | 142 | 570 | 5695 |
| | 98 | 441 | 5492 |
| | | 441 | 3559 |
| | | 435 | 3378 |
| | | 358 | 3165 |
| | | 335 | 2283 |
| | | 217 | 2057 |
| | | 199 | 1840 |
| | | 192 | 1108 |
| | | 182 | 662 |
| | | 178 | 355 |
| | | 174 | 280 |
| | | 167 | 259 |
| | | 166 | 242 |
| | | 160 | 184 |
| | | 141 | 182 |
| | | 132 | 159 |
| | | 91 | 126 |
| Average | | 888.2 +/− 961.8 | |
| Avg + 3XStDev | | 3773.7 | |

Immature embryos were scored as positive for GFP expression if a fluorescence value higher than three standard deviations above background values was observed.

Table 2 shows that one of the 24 untreated embryos were scored as positive, while 8 of the 24 pre-conditioned embryos were scored as positive for transient GFP expression. While the standard deviations were quite large for the fluorescence values, this is an expected result because both GFP-expressing and non-expressing immature embryos were assessed as a result of the random choice of embryos for testing. These results show a substantial improvement in transient GFP expression in maize immature embryos resulting from the Break-Thru 5233 pre-conditioning treatment following co-cultivation with *Agrobacterium* harboring a superbinary vector.

GFP expression in maize immature embryos in experiment ZM1 were also scored according to the relative GFP expression protocol, scoring each embryo on a scale of 0-3. Table 3 shows the results of this scoring and is in agreement with the data obtained from the plate reader.

TABLE 3

Relative Transient GFP expression after 131440 co-cultivation in experiment ZM1

| | n | GFP0 | GFP1 | GFP2 | GFP3 |
|---|---|---|---|---|---|
| Untreated | 167 | 28.1% | 58.7% | 12.6% | 0.6% |
| S233 Pre-conditioned | 154 | 7.1% | 16.2% | 29.2% | 47.4% |

Example 5—Comparison of Surfactant Pre-Conditioning Treatments on Maize Transient GFP Expression Transient expression of GFP was measured following co-cultivation of maize tissue with LBA4404 *Agrobacte-*

*rium* cells harboring superbinary vector 130571. The effect of pre-conditioning medium comprising 0.01% (v/v) Break-Thru S233 or Break-Thru S301 was tested. Twenty-four embryos each were selected from: 1) untreated embryos, 2) Break-Thru S233 preconditioned embryos, and 3) Break-Thru S301 preconditioned embryos. GFP fluorescence was quantified for these embryos, as summarized in Table 4.

TABLE 4

RFU Values for untreated embryos, S233 pre-conditioned, and S301 pre-conditioned embryos in experiment ZM4

|  | untreated | S233 | S301 |
|---|---|---|---|
| <500 | 11 | 8 | 7 |
| 501-999 | 4 | 0 | 4 |
| 1000-1500 | 1 | 1 | 0 |
| 1501-2000 | 2 | 5 | 0 |
| >2001 | 6 | 10 | 13 |

As Table 4 shows, pre-conditioning with either Break-Thru S233 or Break-Thru S301 resulted in an increased number of highly-expressing immature embryos (embryos with an RFU reading of >2001) relative to untreated embryos that did not receive any preconditioning treatment.

GFP expression in maize immature embryos in experiment ZM4 were also scored according to the relative GFP expression protocol, scoring each embryo on a scale of 0-3. Table 5 shows the results of this scoring which is consistent with the data obtained from the plate reader.

TABLE 5

Relative Transient GFP expression in experiment ZM4

|  | n | GFP0 | GFP1 | GFP2 | GFP3 |
|---|---|---|---|---|---|
| Unconditioned | 80 | 21% | 50% | 24% | 5% |
| S233 | 100 | 9% | 15% | 39% | 37% |
| S301 | 81 | 10% | 15% | 40% | 36% |

The effect of using different surfactants for pre-conditioning was examined further. Transient expression of GFP was measured following co-cultivation of maize tissue with LBA4404 *Agrobacterium* cells harboring superbinary vector 130571. The effect of pre-conditioning medium comprising 0.01% (v/v) Break-Thru 5233, Break-Thru 5240, Break-Thru 5279, or Break-Thru S301 was tested. GFP fluorescence was scored by visual inspection on a scale from 0-3, with 0 indicating no visible fluorescence and 3 indicating a high level of fluorescence. Table 6 summarizes the results of these experiments.

TABLE 6

RFU Values for control and pre-conditioned maize embryos in experiment ZM3

| Preconditioning | n | GFP 0 | GFP 1 | GFP 2 | GFP 3 |
|---|---|---|---|---|---|
| Control | 106 | 18.9% | 51.9% | 21.7% | 7.5% |
| 233 | 87 | 1.1% | 14.9% | 32.2% | 51.7% |
| 240 | 94 | 6.4% | 28.7% | 26.6% | 38.3% |
| 279 | 104 | 5.8% | 43.3% | 19.2% | 31.7% |
| 301 | 85 | 0.0% | 9.4% | 29.4% | 61.2% |

As Table 6 shows, all four of the pre-conditioning treatments led to a decrease in the proportion of embryos that failed to show any visible fluorescence. All of the pre-conditioning treatments also led to an increase in the proportion of embryos scored as '3' indicating very high levels of GFP fluorescence and to an increase in the proportion of embryos scored as '2' or '3' indicating high levels of GFP fluorescence (29.2%, 83.9%, 64.9%, 51.0%, and 90.6%, respectively, for control, S233, 5240, S279, and S301 preconditioning treatments). This data indicates that preconditioning maize immature embryos with Break-Thru S233, Break-Thru 5240, Break-Thru S279, or Break-Thru S301 results in increased levels of transient expression of GFP relative to untreated control embryos.

Example 6—*Setaria viridis* Transformation Materials and Callus Induction

Plant Materials and Callus Induction

Mature seeds of greenhouse grown *Setaria viridis* were stored at for 3-6 months prior to using them for transformation. Seeds were de-coated taking special care not to damage the embryos. Seed coats and chaffe were removed by blowing away the material and separating the clean embryos from the debris. Clean seed was placed into a 50 mL tube for sterilization.

Seeds were sterilized with 70% ethanol for 1 minute, followed by one rinse with Millipore water. Sterilization followed 40 mL 20% (v/v) commercial bleach solution containing 0.17% (v/v) Tween-20, for 8 min, with inversion. Seeds were rinsed with autoclaved Millipore water five times to effectively remove all bleach from the surface.

Sterilized seeds were allowed to air dry in a laminar flow hood on top of sterilized filter paper for a minimum of 20 minutes before plating, embryo side up, onto callus induction media (SKIT) (MS salts 4.33 g/L, MS vitamins 1000×1 mL/L, maltose 40 g/L, $ZnSO_4 \cdot 7H_2O$ 35 mg/L, $CuSO_4$ 0.6 mg/L, 2,4-D 2 mg/L, kinetin 0.5 mg/L, Phytagel 3.5 g/L, pH 5.8). Plates were wrapped with parafilm and incubated in a low light chamber at 26° C. for 4 weeks.

After 4 weeks on callus induction media SVKT, embryogenic callus was selected and transferred to fresh callus media without kinetin SVNKT media (MS salts 4.33 g/L, MS vitamins 1000×1 mL/L, maltose 40 g/L, $ZnSO_4 \cdot 7H_2O$ 35 mg/L, $CuSO_4$ 0.6 mg/L, 2,4-D 2 mg/L, Phytagel 3.5 g/L, pH 5.8). Any non-embryogenic calli were discarded and only white compact callus was transferred. Plates were sealed with parafilm and incubated in a low light chamber at 26'C for 10 days. Callus was then broken down into small pieces and transferred to fresh SVNKT media for bulk up 3 days prior to transformation. Plates were wrapped with parafilm and incubated in a low light chamber at 26° C. for 3 days.

*Agrobacterium* Culture Initiation

Glycerol stocks of *Agrobacterium* containing the appropriate vector were stored at −80° C. until ready to use. A loop from the frozen glycerol stock was streaked on AB minimal medium plates containing appropriate antibiotics and plates were grown at 20-25° C. for 3 days in the dark. A single colony was then picked and streaked onto YEP plates containing the same antibiotics and was incubated at 28° C. for 1-3 days.

*Agrobacterium* Culture

On the day of the experiment, *Agrobacterium* colonies were taken from the YEP plate, suspended in 10 mL of infection medium in a 50 mL disposable tube, and the cell density adjusted to OD600=0.2-0.4 nm for *Agrobacterium* LBA4404 harboring superbinary vector 130836 (SEQ ID NO:11) using a spectrophotometer. *Agrobacterium* cultures were placed on a rotary shaker at 120-130 rpm, room temperature, while embryo dissection was performed.

*Setaria viridis* Pre-Conditioning

Callus from 3-day sub-culture plates was transferred to empty 50 ml conical tubes. One plate of callus should fill one 50 ml tube. The preconditioning treatment lasted between 5 min-60 min at 24° C.

*Agrobacterium* Infection and Co-Cultivation

After all callus was collected and preconditioned, the preconditioning media was removed and discarded. After removal of the preconditioning media, enough *Agrobacterium* suspension was added to each tube to cover the callus. Tubes were then vortexed on high setting for 15-20 seconds and allowed to rest at room temperature in the dark for 5 minutes *Agrobacterium* suspension was then poured out onto a petri dish containing sterile filter paper (2), allowing the filter paper to soak all suspension. Explants were allowed to air dry for 5 minutes in the laminar flow hood before transferring the top filter paper to MS co-culture media MS CC (MS salts 4.33 g/L, MS vitamins (1000×) 1 mL/L, sucrose 20 g/L, glucose 10 g/L, casein 0.1 g/L, L-proline 0.7 g/L, 2,4-D 1.5 mg/L, MES 0.5 g/L, Phytagel 3.5 g/L, pH 5.8). Plates were wrapped with vent tape and incubated at 25° C. in the dark for 72 hours.

Callus Selection and Regeneration of Putative Events

Following the co-cultivation period, calli were transferred to selection 1 media SV Sel 60 (MS salts 4.33 g/L, MS vitamins 1000× 1 mL/L, maltose 40 g/L, $ZnSO_4 \cdot 7H_2O$ 35 mg/L, $CuSO_4$ 0.6 mg/L, 2,4-D 2 mg/L, Timentin 100 mg/L, Hygromycin 60 mg/L, Phytagel 3.5 g/L, pH 5.8). Plates were wrapped with parafilm and incubated in the dark at 26° C. for 14±2 days. Callus was transferred to fresh selection 2 media SV Sel 60, taking care to keep original callus pieces together. Plates were wrapped with parafilm and incubated in the dark at 26° C. for 14±2 days After 14.1.2 days, explants were transferred to selection 3 media SV Sel 60 KT (MS salts 4.33 g/L, MS vitamins 1000×1 mL/L, maltose 40 g/L, $ZnSO_4 \cdot 7H_2O$ 35 mg, $CuS_4$ 0.6 mg/L, 2,4-D 2 mg/L, kinetin 0.5 mg/L, Timentin 100 mg/L, Hygromycin 60 mg/L, Phytagel 3.5 g/L, pH 5.8). Plates were wrapped with parafilm and incubated in the dark at 26° C. for 14±2 days. Callus was then transferred to Regeneration 1 media (MS salts 4.33 g/L, MS vitamins 1000× 1 mL/L, maltose 40 g/L, $ZnSO_4$ $7H_2O$ 35 mg/L, $CuSO_4$ 0.6 mg/L, 2,4-D 2 mg/L, kinetin 0.2 mg/L, Timentin 100 mg/L, Hygromycin 20 mg/L, Phytagel 3.5 g/L, pH 5.8). Once plantlet formation was established, they were transferred to a larger vessel to allow root formation to establish. Plantlets were handed off to greenhouse for acclimation and molecular characterization.

Example 7—Transient GFP Expression in *Setaria viridis* Following Superbinary Vector Transformation Transient expression of GFP was measured following co-cultivation of *S. viridis* tissue with LBA4404 *Agrobacterium* cells harboring superbinary vector 130836. The effect of pre-conditioning medium comprising 0.01% (v/v) Break-Thru 5233 or 0.01% (v/v) Break-Thru S301 was tested. GFP fluorescence was scored based on visual inspection. Table 7 shows the results of quantification of this transient GFP expression.

TABLE 7

Transient GFP expression after 130836 co-cultivation

|  | n | GFP0 | GFP1 | GFP2 | GFP3 |
| --- | --- | --- | --- | --- | --- |
| Unconditioned | 76 | 26% | 59% | 13% | 1% |
| S233 | 85 | 6% | 9% | 19% | 66% |
| S301 | 87 | 13% | 17% | 33% | 37% |

As Table 7 shows, treatment with either Break-Thru S233 or Break-Thru S301 resulted in a shift toward higher expression of GFP in *S. viridis* tissue following infection with the 130836 vector. While 22.0-31.4% of untreated control callus pieces failed to show detectable GFP expression and only 0.0-2.4% of those untreated control callus pieces were scored as '3,' indicating high GFP fluorescence, only 4.7-7.1% and 10.9-14.6% of S233 and S301-treated *S. viridis* callus pieces, respectively, failed to show detectable fluorescence. 64.3-67.4% and 34.1-39.1% of S233 and S301-treated *S. viridis* callus pieces, respectively, were scored as '3,' indicating high GFP fluorescence. Untreated control *S. viridis* callus pieces showed just 11.4-17.1% scored as high GFP expressors (scores of '2' or '3'), while S233 and S301 callus pieces showed 83.7-85.7% and 63.4-76.1%, respectively, that were scored as either '2' or '3.' These results indicate that pre-conditioning of *S. viridis* tissue with Break-Thru S233 or Break-Thru S301 results in increased transient GFP expression measured as the fraction of callus pieces showing visible GFP-derived fluorescence or as the fraction of callus pieces showing high levels of GFP-derived fluorescence.

Example 8—Stable GFP Expression in Maize Following Plant Regeneration

Following co-cultivation with *Agrobacterium* cells harboring appropriate transformation vectors, maize immature embryos were maintained on tissue culture medium comprising appropriate selective agents to prevent growth of untransformed cells and appropriate hormones and other components to promote shoot growth. Following the appearance of shoots, these shoots were transferred to appropriate tissue culture medium for rooting. After root establishment, rooted plantlets were transferred to soil for growth in a greenhouse. Tissue samples may be collected from shoots prior to root establishment or after root establishment, when the plants are maintained on tissue culture medium or in soil. These samples are analyzed for GFP expression by visual inspection and/or by well-known molecular or biochemical methods such as Northern or western blotting or RT-PCR methods to detect RNA and/or protein accumulation of the GFP transcript and/or protein. Alternatively, GFP expression may be assessed in whole plants without collecting any samples through visual inspection. Because *Agrobacterium* has been eliminated from these cultures, detection of GFP expression and/or protein accumulation indicates that the GFP gene is stably inserted in the plant genome.

Tables 8, 9, and 10 summarize the quantification of stable GFP expression in immature embryos in experiments ZM1, ZM3, and ZM4, respectively.

TABLE 8

Stable GFP expression in experiment ZM1

| Treatment | # Transformed embryos | GFP sectors | GFP sectors |
|---|---|---|---|
| Unconditioned | 167 | 23 | 14% |
| S233 conditioned | 154 | 61 | 40% |

TABLE 9

Stable GFP expression in experiment ZM3

| Treatment | # Embryos transformed | GFP sectors | GFP sectors |
|---|---|---|---|
| Unconditioned | 106 | 12 | 11% |
| S233 conditioned | 87 | 50 | 57% |
| S240 conditioned | 94 | 71 | 76% |
| S279 conditioned | 104 | 30 | 29% |
| S301 conditioned | 85 | 39 | 46% |

TABLE 10

Stable GFP expression in experiment ZM4

| Treatment | # Embryos transformed | GFP sectors | GFP sectors (%) |
|---|---|---|---|
| Unconditioned | 80 | 46 | 58% |
| S233 conditioned | 100 | 78 | 78% |
| S301 conditioned | 81 | 74 | 91% |

The data in Tables 8-10 show that pre-conditioning with the tested surfactants led to an increase in the proportion of stably expressing GFP sectors relative to unconditioned maize embryos.

GFP expression was also quantified in regenerated maize plantlets produced from experiments ZM1, ZM3, and ZM4, as summarized in Tables 11-13, respectively.

TABLE 11

GFP expression in regenerated plantlets in experiment ZM1

| Treatment | # Transformed embryos | # GFP-Positive events | Transformation % |
|---|---|---|---|
| Unconditioned | 167 | 15 | 9% |
| S233 conditioned | 154 | 32 | 21% |

TABLE 12

GFP expression in regenerated plantlets in experiment ZM3

| Treatment | # Embryos transformed | # GFP positive events | Transformation % |
|---|---|---|---|
| Unconditioned | 106 | 11 | 10.4% |
| S233 conditioned | 87 | 29 | 33.3% |
| S240 conditioned | 94 | 18 | 19.1% |
| S279 conditioned | 104 | 14 | 13.5% |
| S301 conditioned | 85 | 30 | 35.3% |

TABLE 13

GFP expression in regenerated plantlets in experiment ZM4

| Treatment | # Embryos transformed | # GFP-Positive events | Transformation % |
|---|---|---|---|
| Unconditioned | 80 | 19 | 23.8% |
| S233 conditioned | 100 | 39 | 39.0% |
| S301 conditioned | 81 | 36 | 44.4% |

The data in Tables 11-13 show that pre-conditioning with the tested surfactants led to an increase in the number of GFP-positive regenerated maize plants in each of these experiments.

Following maturation of the T0 generation plants, the plants are pollinated and the resulting seeds may be grown to produce T1 generation plants. These T1 generation plants are similarly analyzed for stable expression of GFP.

Example 9—Stable GFP Expression in *Setaria viridis* Following Plant Regeneration Following co-cultivation with *Agrobacterium* cells harboring appropriate transformation vectors, *S. viridis* callus pieces were maintained on tissue culture medium comprising appropriate selective agents to prevent growth of untransformed cells and appropriate hormones and other components to promote shoot growth. Following the appearance of shoots, these shoots were transferred to appropriate tissue culture medium for rooting. After root establishment, rooted plantlets were transferred to soil for growth in a greenhouse. Tissue samples may be collected from shoots prior to root establishment or after root establishment, when the plants are maintained on tissue culture medium or in soil. These samples are analyzed for GFP expression by visual inspection and/or by well-known molecular or biochemical methods such as Northern or western blotting or RT-PCR methods to detect RNA and/or protein accumulation of the GFP transcript and/or protein. Alternatively, GFP expression may be assessed visually in the plantlets without collecting any tissue samples. Because *Agrobacterium* has been eliminated from these cultures, detection of GFP expression and/or protein accumulation indicates that the GFP gene is stably inserted in the plant genome.

Table 14 summarizes the results of quantifying stable GFP expression in *S. viridis* callus tissues.

TABLE 14

Stable GFP expression in *S. viridis* callus

| Treatment | # Calli transformed | GFP sectors | GFP sectors |
|---|---|---|---|
| Unconditioned | 76 | 6 | 8% |
| S233 conditioned | 85 | 28 | 33% |
| S301 conditioned | 87 | 10 | 11% |

The data in Table 14 show that pre-conditioning *S. viridis* with either of the tested surfactants led to an increase in the proportion of stable sectors relative to unconditioned *S. viridis*.

GFP expression was also quantified in regenerated *S. viridis* plantlets, as summarized in Table 15.

TABLE 15

GFP expression in regenerated *S. viridis* plantlets

| Treatment | # Calli transformed | # GFP-Positive events | Transformation % |
|---|---|---|---|
| Unconditioned | 76 | 2 | 3% |
| S233 conditioned | 85 | 11 | 13% |
| S301 conditioned | 87 | 2 | 2% |

The data in Table 15 show that pre-conditioning with S233, but not with S301, led to an increase in the proportion of GFP-positive regenerated *S. viridis* plantlets relative to unconditioned *S. viridis*.

Following maturation of the T0 generation plants, the plants are pollinated and the resulting seeds may be grown to produce T1 generation plants. These T1 generation plants are similarly analyzed for stable expression of GFP.

Example 10—Pea Transformation Materials and Transformation Protocols

Plant Materials
Seeds Sterilization, Germination and Explant Preparation

Seeds of Yellow Pea (*Pisum sativum* cv. Amigo) were surface sterilized by immersion in a 30% (v/v) solution of bleach containing 0.05% (v/v) Tween-20. The seeds were shaken for 30-45 minutes, followed by three rinses in sterile water. After sterilization, seeds were cultured on MS media (MS salts, 4.33 gm/L; B5 vitamins [1000×] (Gamborg et al. 1968), 1.00 mL/L; sucrose, 30 gm/L; 2,4-D, 1-2 mg/L; pH adjusted to 5.8). Seeds were incubated in the dark for 1-2 days at 25° C. Pre-cultured seeds were then either 1) longitudinally split into two halves with each half containing part of the embryonic leaf/shoot and root targeting competent cells for transformation and regeneration (split seed explants), or 2) the embryo containing shoot and root was removed and used for transformation (meristem tissues).

*Agrobacterium* Culture Initiation

Glycerol stocks of *Agrobacterium* containing a vector 133337 (SEQ ID NO:12), comprising Cp4 (SEQ ID NO:13, encoding SEQ ID NO:14) and GFP with a C-terminal SEKDEL fusion (SEQ ID NO:15, encoding SEQ ID NO:16) genes as selectable and visual marker genes, respectively, were stored at −80° C. until ready to use. A loop from the frozen glycerol was streaked on AB minimal medium plates containing appropriate antibiotics and plates were grown at 20-25° C. for 3 days in the dark. A single colony was then picked and streaked onto YEP plate containing the same antibiotics and was incubated at 28° C. for 1-3 days.

*Agrobacterium* Culture, Infection, and Co-Cultivation

On the day of the experiment, a loop of *Agrobacterium tumefaciens* strain AGL1 harboring vector 133337 was taken from the YEP plate, suspended in 10 mL of infection medium in a 50 mL disposable tube, and the cell density at OD 600 nm was adjusted to 0.2-0.4 using a spectrophotometer. *Agrobacterium* culture was placed on a rotary shaker at 120-130 rpm, room temperature, while explant preparation was performed.

After a 1-2-day pre-culture period, split-seed explants were either collected in 10-15 mL of the infection medium alone or in infection media plus different surfactant agents for preconditioning. The preconditioning treatment lasted between 5 min-60 min. After all explants were transferred preconditioned media and infection media were discarded. Ten to fifteen milliliters of *Agrobacterium* suspension were added to each tube containing the split-seed explants. Tubes were inverted a few times and placed on rocker shaker for 30-45 minutes. After inoculation, the *Agrobacterium* culture was discarded, and explants were then blotted dry on sterile filter paper to remove excess inoculum. Infected split-seeds were then transferred adaxial side up onto co-culture media (MS salts, 4.33 gm/L; B5 vitamins [1000×] (Gamborg et al. 1968), 1.00 mL/L; sucrose, 30 gm/L; 2,4-D, 1 mg/L; Kinetin, 0.5 mg/L; Acetosyringone, 200 µM; Gelzan™ 2.3 gm/L; pH was adjusted to 5.6 prior to autoclaving). The plates were incubated for 3-5 days in the dark at 21-25° C.

Selection and Regeneration of Transgenic Shoots

After 3-5 days of co-cultivation, split-seed explants were blotted onto sterile filter paper and were then transferred onto selection media 1 (MS salts, 4.33 gm/L; B5 vitamins [1000×] (Gamborg et al. 1968), 1.00 mL/L; sucrose, 30 gm/L; BA, 2.0 mg/L; NAA, 0.2 mg/L; Glyphosate 0.1 mM; cefotaxime 250 mg/L; Gelzan™ 2.3 gm/L; pH was adjusted to 5.8 prior to autoclaving). Plates were cultured at 25° C., 16 h photoperiod, 50 µmol $m^2s^{-1}$ light intensity. Explants were sub-cultured onto selection media 2 (MS salts, 4.33 gm/L; B5 vitamins [1000×] (Gamborg et al. 1968), 1.00 mL/L; sucrose, 30 gm/L; Zeatin, 2 mg/L; Kinetin, 0.5 mg/L; Glyphosate 0.1 mM; cefotaxime 250 mg/L; Gelzan™ 2.3 gm/L; pH was adjusted to 5.8 prior to autoclaving). Explants were sub-cultured every two weeks on the same media and incubated at 25° C., 16 h photoperiod, 50 µmol $m^2s^{-1}$ light intensity until shoot regeneration.

Example 11—Transient GFP Expression in Pea

Transient expression of GFP was measured following co-cultivation of *P. sativum* split seed tissue with AGL1 *Agrobacterium* cells harboring the 133337 vector. The effect of pre-conditioning medium comprising 0.01% (v/v) Break-Thru 5233 or 0.01% (v/v) Break-Thru S301 was tested. GFP fluorescence was scored based on visual inspection. Table 16 shows the results of quantification of this transient GFP expression in split *P. sativum* seeds.

TABLE 16

Transient GFP expression in *P. sativum* split seeds after 133337 co-cultivation

| Treatment | n | GFP 0 | GFP 1 | GFP 2 | GFP 3 |
|---|---|---|---|---|---|
| Unconditioned | 40 | 0 | 35.0 | 37.5 | 27.5 |
| S301 | 42 | 0 | 4.8 | 52.4 | 42.9 |
| S233 | 40 | 0 | 12.5 | 50.0 | 37.5 |

As Table 16 shows, treatment with either Break-Thru S233 or Break-Thru S301 resulted in a shift toward higher expression of GFP in split seeds of *P. sativum* tissue following infection with the 133337 vector. While 35.0% of untreated control split seed pieces showed low levels of GFP expression (GFP category 1), only 12.5% and 4.8% of S233 and S301-treated *P. sativum* split seeds, respectively, showed these low levels of GFP fluorescence. Untreated control split seeds of *P. sativum* showed just 65.0% scored as high GFP expressors (scores of '2' or '3'), while S233 and S301 callus pieces showed 87.5% and 95.2%, respectively, that were scored as either '2' or '3.' These results indicate that pre-conditioning of split seeds of *P. sativum* with Break-Thru 5233 or Break-Thru S301 results in increased transient GFP expression measured as the fraction of split seeds showing visible GFP-derived fluorescence or as the fraction of split seeds showing high levels of GFP-derived fluorescence.

Transient expression of GFP was also measured following co-cultivation of *P. sativum* meristem tissue with AGL1 *Agrobacterium* cells harboring the 133337 vector. The effect of pre-conditioning medium comprising 0.01% (v/v) Break-Thru S233 or 0.01% (v/v) Break-Thru S301 was tested. GFP fluorescence was scored based on visual inspection. Table 17 shows the results of quantification of this transient GFP expression in *P. sativum* meristem tissues.

TABLE 17

Transient GFP expression in *P. sativum* meristem tissue after 133337 co-cultivation

| Treatment | n | GFP 0 | GFP 1 | GFP 2 | GFP 3 |
|---|---|---|---|---|---|
| Unconditioned | 19 | 0 | 68.4 | 21.1 | 10.5 |
| S301 | 20 | 0 | 40.0 | 35.0 | 25.0 |
| S233 | 20 | 0 | 35.0 | 45.0 | 20.0 |

As Table 17 shows, treatment with either Break-Thru S233 or Break-Thru S301 resulted in a shift toward higher expression of GFP in meristematic tissue of *P. sativum* following infection with the 133337 vector. While 68.4% of untreated control split seed pieces showed low levels of GFP expression (GFP category 1), only 35.0% and 40.0% of S233 and S301-treated *P. sativum* meristematic tissues, respectively, showed these low levels of GFP fluorescence. Untreated control split seeds of *P. sativum* showed just 31.6% scored as high GFP expressors (scores of '2' or '3'), while S233 and S301 callus pieces scored 65.0% and 60.0%, respectively, that were scored as either '2' or '3.' These results indicate that pre-conditioning of meristematic tissue of *P. sativum* with Break-Thru S233 or Break-Thru S301 results in increased transient GFP expression measured as the fraction of meristematic tissues showing visible GFP-derived fluorescence or as the fraction of meristematic tissue pieces showing high levels of GFP-derived fluorescence.

Transient expression of GFP was measured in a separate set of experiments following co-cultivation of *P. sativum* split seed tissue with AGL1 *Agrobacterium* cells harboring the 133337 vector. The effect of pre-conditioning medium comprising 0.01% (v/v) Break-Thru S301 or 0.01% (v/v) Pluronic™ F-68 was tested. GFP fluorescence was scored based on visual inspection. Table 18 shows the results of quantification of this transient GFP expression in split *P. sativum* seeds.

TABLE 18

Transient GFP expression in *P. sativum* split seeds after 133337 co-cultivation

| Treatment | n | GFP 0 | GFP 1 | GFP 2 | GFP 3 |
|---|---|---|---|---|---|
| Unconditioned | 40 | 0 | 35.0 | 30.0 | 35.0 |
| S301 | 40 | 0 | 5.0 | 45.0 | 50.0 |
| Pluronic | 40 | 0 | 5.0 | 42.5 | 52.5 |

As Table 18 shows, preconditioning with either Break-Thru S301 or with Pluronic resulted in a shift toward higher expression of GFP in split seeds of *P. sativum* tissue following infection with the 133337 vector. Further, the data in Table 8 shows that the effect of preconditioning with Break-Thru S301 is reproducible based on a comparison with the data in Table 6. While 35.0% of untreated control split seed pieces showed low levels of GFP expression (GFP category 1), only 5.0% of S301 or Pluronic-preconditioned *P. sativum* split seeds, respectively, showed these low levels of GFP fluorescence. Unconditioned control split seeds of *P. sativum* showed just 65.0% scored as high GFP expressors (scores of '2' or '3'), while S301 and Pluronic-preconditioned callus pieces showed 95.0% that were scored as either '2' or '3.' These results indicate that pre-conditioning of split seeds of *P. sativum* with Break-Thru S301 or Pluronic results in increased transient GFP expression measured as the fraction of split seeds showing visible GFP-derived fluorescence or as the fraction of split seeds showing high levels of GFP-derived fluorescence.

Transient expression of GFP was also measured in a separate set of experiments following co-cultivation of *P. sativum* meristem tissue with AGL1 *Agrobacterium* cells harboring the 133337 vector. The effect of pre-conditioning medium comprising 0.01% (v/v) Break-Thru S301 or 0.01% (v/v) Pluronic™ F-68 was tested. GFP fluorescence was scored based on visual inspection. Table 19 shows the results of quantification of this transient GFP expression in *P. sativum* meristem tissues.

TABLE 19

Transient GFP expression in *P. sativum* meristem tissue after 133337 co-cultivation

| Treatment | n | GFP 0 | GFP 1 | GFP 2 | GFP 3 |
|---|---|---|---|---|---|
| Unconditioned | 20 | 0 | 60.0 | 30.0 | 10.0 |
| S301 | 20 | 0 | 30.0 | 45.0 | 25.0 |
| Pluronic | 14 | 0 | 35.7 | 35.7 | 28.6 |

As Table 19 shows, preconditioning with either Break-Thru S301 or with Pluronic resulted in a shift toward higher expression of GFP in meristematic tissue of *P. sativum* following infection with the 133337 vector. Comparison of the data in Table 9 with the data in Table 7 also shows that preconditioning with Break-Thru S301 is reproducible. In these experiments, while 60.0% of untreated control split seed pieces showed low levels of GFP expression (GFP category 1), only 30.0% and 35.7% of S301 and Pluronic-preconditioned *P. sativum* meristematic tissues, respectively, showed these low levels of GFP fluorescence. Untreated control split seeds of *P. sativum* showed just 40.0% scored as high GFP expressors (scores of '2' or '3'), while S301 and Pluronic callus pieces showed 70.0% and 64.3%, respectively, that were scored as either '2' or '3.' These results indicate that pre-conditioning of meristematic tissue of *P. sativum* with Break-Thru S301 or Pluronic results in increased transient GFP expression measured as the fraction of meristematic tissues showing visible GFP-derived fluorescence or as the fraction of meristematic tissue pieces showing high levels of GFP-derived fluorescence.

Example 12—Tomato Transformation Materials and Transformation Protocols

Plant Materials
Seeds Sterilization, Germination and Explant Preparation

Seeds of tomato (*Solanum lycopersicum* cv. Rio Grande) were surface sterilized by immersion in a 20% (v/v) solution of household bleach containing 0.25% (v/v) Tween-20. The seeds were shaken for 20 minutes, followed by three rinses in sterile water. After sterilization, seeds were germinated in phytatrays (Sigma-Aldrich, St. Louis, Mo.) containing ½× MS media (½× MS salts, 2.17 gm/L; B5 vitamins [1000×]

(Gamborg et al. 1968), 1.00 mL/L; sucrose, 15 gm/L, pH was adjusted to 5.8). Seeds were incubated in the dark for 2-3 days at 25° C. Germinated seeds were then transferred to a lit chamber (16 h photoperiod, 45 µmol m$^2$s$^1$ light intensity and 60% relative humidity) for 8-13 days. For a given set of experiments, pooled cotyledons from 8-13 day-old seedlings were cut and precultured on MS media (MS salts, 4.33 gm/L; B5 vitamins [1000×] (Gamborg et al. 1968), 1.00 mL/L; sucrose, 30 gm/L; BA, 1.5 mg/L; NAA, 0.1 mg/L; Gelzan™ 2.3 gm/L, pH adjusted to 5.8 prior to autoclaving). Plates were cultured in the dark or a lit chamber (16 h of photoperiod, 45 µmol m$^2$s$^{-1}$ light intensity and 60% relative humidity (RH)) at 25° C.

Agrobacterium Culture Initiation

Glycerol stocks of *Agrobacterium* containing vector 133336 (SEQ ID NO:17), which comprises NptII (SEQ ID NO:3, encoding SEQ ID NO:4) and GFP with a C-terminal SEKDEL fusion (SEQ ID NO:15, encoding SEQ ID NO:16) genes as selectable marker and visual selection genes, respectively were stored at −80° C. until ready to use. A loop from the frozen glycerol stock was streaked on AB minimal medium plates containing appropriate antibiotics and plates were grown at 20-25° C. for 3 days in the dark. A single colony was then picked and streaked onto a YEP plate containing the same antibiotics and was incubated at 28° C. for 1-3 days.

Agrobacterium Culture, Infection, and Co-Cultivation

On the day of the experiment, a loop of *Agrobacterium* AGL1/p133336 was taken from the YEP plate, suspended in 10 mL of infection medium in a 50 mL disposable tube, and the cell density at OD 600 nm was adjusted to 0.2-0.4 for AGL1 using a spectrophotometer. *Agrobacterium* culture was placed on a rotary shaker at 120-130 rpm at room temperature, while explant preparation was performed.

After 2-day pre-culture period, cotyledon explants were either collected in 5-10 mL of the infection medium alone or in infection media comprising the appropriate surfactant agent for preconditioning. The preconditioning treatment lasted between 5 min-60 min. After preconditioning, the preconditioning media and infection media were discarded and ten milliliters of *Agrobacterium* suspension were added to each tube. Tubes were inverted a few times and placed on rocker shaker for 15-30 minutes. After inoculation, *Agrobacterium* culture was discarded, and explants were then blotted dry on sterile filter paper to remove excess inoculum. Infected cotyledons were then transferred abaxial side up onto co-culture media (MS salts, 4.33 gm/L; B5 vitamins [1000×] (Gamborg et al. 1968), 1.00 mL/L; sucrose, 30 gm/L; BA, 1.5 mg/L; NAA, 0.1 mg/L; Acetosyringone, 200 µM; Gelzan™ 2.3 gm/L, pH adjusted to 5.8 prior to autoclaving). The plates were incubated for 2-3 days in the dark at 21-25° C.

Selection and Regeneration of Transgenic Shoots

After 2-3 days of co-cultivation, the explants were washed thoroughly with MS liquid media containing cefotaxime (150 mg/L) to remove excess inoculum. Explants were blotted onto sterile filter paper and were then transferred onto selection media (MS salts, 4.33 gm/L; B5 vitamins [1000×] (Gamborg et al. 1968), 1.00 mL/L; sucrose, 30 gm/L; Zeatin, 2.0 mg/L; IAA, 0.5 mg/L; Kanamycin 50-100 mg/L and cefotaxime 150 mg/L; Gelzan™ 2.3 gm/L, pH adjusted to 5.8 prior to autoclaving). Plates were cultured at 25° C., 16 h photoperiod, 50 µmol m$^2$s$^{-1}$ light intensity and 50% RH. Explants were subcultured onto fresh selection media every two weeks until shoot regeneration.

Example 13—Transient GFP Expression in Tomato

Transient expression of GFP was measured following co-cultivation of *S. lycopersicum* cotyledon tissue with AGL1 *Agrobacterium* cells harboring the 133336 vector. The effect of pre-conditioning medium comprising 0.01% (v/v) Break-Thru S233 or 0.01% (v/v) Break-Thru S301 was tested with the cotyledons of eight day-old seedlings. GFP fluorescence was scored based on visual inspection. Table 20 shows the results of quantification of this transient GFP expression in *S. lycopersicum* cotyledon tissue.

TABLE 20

Transient GFP expression in cotyledon tissue from 8-day old *S. lycopersicum* seedlings after 133336 co-cultivation

| Treatment | n | GFP 0 | GFP 1 | GFP 2 | GFP 3 |
| --- | --- | --- | --- | --- | --- |
| Unconditioned | 50 | 12.0 | 56.0 | 16.0 | 16.0 |
| S233 | 52 | 7.7 | 19.2 | 46.2 | 26.9 |
| S301 | 55 | 5.5 | 12.7 | 52.7 | 29.1 |

As Table 20 shows, preconditioning treatment with either Break-Thru 5233 or Break-Thru S301 resulted in a shift toward higher expression of GFP in cotyledon tissue of *S. lycopersicum* following infection with the 133336 vector. While 12.0% and 56.0% of untreated control cotyledon tissue pieces showed no GFP expression or low levels of GFP expression (GFP category 0 or 1, respectively), respectively, only 7.7% and 5.5% of S233 and S301-treated *S. lycopersicum* cotyledon tissues, respectively, showed undetectable levels of GFP fluorescence, and only 19.2% and 12.7% of S233 and S301-preconditioned *S. lycopersicum* cotyledon tissues, respectively, showed low levels of GFP expression (category 1). Untreated control cotyledon tissue showed just 32.0% scored as high GFP expressors (scores of '2' or '3'), while S233 and S301 callus pieces showed 73.1% and 81.8%, respectively, that were scored as either '2' or '3.' These results indicate that pre-conditioning of cotyledon tissue of *S. lycopersicum* with Break-Thru S233 or Break-Thru S301 results in increased transient GFP expression measured as the fraction of cotyledon tissues showing visible GFP-derived fluorescence or as the fraction of cotyledon tissue pieces showing high levels of GFP-derived fluorescence.

Transient expression of GFP was measured following co-cultivation of *S. lycopersicum* cotyledon tissue with AGL1 *Agrobacterium* cells harboring the 133336 vector. The effect of pre-conditioning medium comprising 0.01% (v/v) Break-Thru S301 or 0.01% (v/v) Pluronic F-68 was tested with the cotyledons of ten day-old seedlings. GFP fluorescence was scored based on visual inspection. Table 21 shows the results of quantification of this transient GFP expression in *S. lycopersicum* cotyledon tissue.

TABLE 21

Transient GFP expression in cotyledon tissue from 10-day old *S. lycopersicum* seedlings after 133336 co-cultivation

| Preconditioning | n | GFP 0 | GFP 1 | GFP 2 | GFP 3 |
| --- | --- | --- | --- | --- | --- |
| Unconditioned | 39 | 10.3 | 51.3 | 30.8 | 7.7 |
| S301 | 41 | 2.4 | 31.7 | 46.3 | 19.5 |
| Pluronic | 45 | 4.4 | 42.2 | 40.0 | 13.3 |

As Table 21 shows, preconditioning treatment with either Break-Thru S301 or Pluronic F-68 resulted in a shift toward higher expression of GFP in cotyledon tissue of *S. lycopersicum* following infection with the 133336 vector. While 10.3% and 51.3% of untreated control cotyledon tissue pieces showed no GFP expression or low levels of GFP expression (GFP category 0 or 1, respectively), respectively, only 2.4% and 31.7% of S301 and Pluronic-preconditioned *S. lycopersicum* cotyledon tissues, respectively, showed undetectable levels of GFP fluorescence, and only 31.7% and 42.2% of S301- and Pluronic-preconditioned *S. lycopersicum* cotyledon tissues, respectively, showed low levels of GFP expression (category 1). Untreated cotyledon tissue showed just 38.5% scored as high GFP expressors (scores of '2' or '3'), while S301 and Pluronic-preconditioned callus pieces showed 65.9% and 53.3%, respectively, that were scored as either '2' or '3.' These results indicate that pre-conditioning of cotyledon tissue of *S. lycopersicum* with Break-Thru S301 or Pluronic F-68 results in increased transient GFP expression measured as the fraction of cotyledon tissues showing visible GFP-derived fluorescence or as the fraction of cotyledon tissue pieces showing high levels of GFP-derived fluorescence.

Example 14—Stable GFP Expression in Pea

As transient GFP expression in pea was shown to be improved by the addition of surfactant pre-conditioning, stable GFP expression in pea transformants was investigated. Table 22 shows the transient GFP expression results from this experiment:

TABLE 22

Transient GFP expression in pea

| Treatment | GFP 0 | GFP 1 | GFP 2 | GFP 3 |
|---|---|---|---|---|
| Unconditioned | 0 | 4 | 8 | 3 |
| S233 | 0 | 3 | 7 | 5 |
| S301 | 0 | 2 | 7 | 6 |
| Pluronic F-68 | 0 | 2 | 6 | 7 |

The results shown in Table 22 show that preconditioning with S233, S301, or Pluronic F-68 results in an increased fraction of split seeds showing high levels of GFP fluorescence. These split seeds were further cultured to produce shoots. Table 23 shows the results of this culturing and production of stably transformed plants.

TABLE 23

Stable GFP expression in pea

| Treatment | GOI + Events | TF % |
|---|---|---|
| Unconditioned | 1 | 6.7 |
| S233 | 2 | 13.3 |
| S301 | 3 | 20 |
| Pluronic F-68 | 5 | 33.3 |

The data in Table 23 shows that preconditioning with S233, S301, or Pluronic F-68 results in an increased transformation frequency relative to unconditioned pea split seeds, with Pluronic F-68 preconditioning leading to the highest observed transformation frequency.

Example 15—Stable GFP Expression in Tomato

As transient GFP expression in tomato was shown to be improved by the addition of surfactant pre-conditioning, stable GFP expression in pea transformants was investigated. Table 24 shows the transient GFP expression results from this experiment.

TABLE 24

Transient GFP expression in tomato

| Treatment | GFP 0 | GFP 1 | GFP 2 | GFP 3 | Total |
|---|---|---|---|---|---|
| Unconditioned | 0 | 61 | 42 | 48 | 151 |
| S301 Pre-conditioned | 0 | 17 | 55 | 70 | 142 |

The data in Table 24 shows that preconditioning with S301 results in a shift toward higher levels of transient GFP expression. This tissue was cultured to generate stably transformed plants. Table 25 summarizes the results of this culturing and plant regeneration.

TABLE 25

Stable GFP expression in tomato

| Treatment | # Confirmed shoots | TF % |
|---|---|---|
| Unconditioned | 34 | 22.5% |
| S301 Pre-conditioned | 54 | 38.0% |

The data in Table 25 shows that S301 preconditioning leads to a substantial increase in tomato transformation efficiency.

Example 16—Preconditioning to Enhance Biolistic Plant Transformation

Maize (*Zea mays* cv. B104) plant tissue was prepared for biolistic transformation essentially as described previously, with modifications (Raji et al (2018) Methods Mol Biol 1676:15-40). Immature maize embryos were transformed without a preconditioning step or with a preconditioning step comprising S301 surfactant (0.01% (v/v), 30 min following osmotic treatment). Following biolistic bombardment of the maize immature embryos with the desired DNA constructs (the "introduced DNA"), the bombarded embryos were maintained on appropriate tissue culture medium to allow for shoot regeneration and event recovery. The number of unique events comprising the introduced genes (i.e., the selectable marker gene and/or additional gene(s) of interest as appropriate) produced from these embryos following bombardment were counted, as were the number of plants. The number of plants produced included both unique events as well as sibling events produced from the same immature embryo. Sibling events may be valuable for example in genome editing experiments where the introduced DNA comprises one or more genome editing nucleases, base editors, or other genes encoding proteins capable of modifying DNA at another site or sites in the targeted genome. In such experiments, sibling plants may comprise the same introduced DNA, but may comprise different genomic modifications as a result of the action of the one or more genome editing nucleases and/or genome editing enzymes. Additionally, for genome editing, events in which one or more components for genome editing are missing but the intended editing is observed can also be useful and desired for downstream applications and would be valuable. Table 26 summarizes the results of these maize biolistic experiments.

TABLE 26

Biolistic maize transformation

|  | # IE | Events | Plants | Event Freq | Plant Freq |
|---|---|---|---|---|---|
| Unconditioned | 1313 | 286 | 958 | 21.8% | 73.0% |
| S301 | 1340 | 424 | 1583 | 31.6% | 118.1% |

The data in table 26 shows that preconditioning with S301 results in substantial increases in both the number of unique events as well as the number of plants. In the absence of preconditioning, 286 events and 958 plants were produced from 1313 immature embryos (3.35 plants per event). Following S301 preconditioning, 424 unique events and 1583 plants were produced from 1340 immature embryos (3.73 plants per event). These results show that preconditioning improves plant transformation and plant regeneration efficiency using the biolistic bombardment method.

Example 17—Preconditioning to Improve Genome Editing Results

Rice (*Oryza sativa*) immature embryos were transformed biolistically with and without a preconditioning treatment. The transformation vectors used in these experiments comprised a Cpf1 genome editing nuclease (vector 133869; SEQ ID NO:18) and a guide RNA (gRNA) (vector 133432; SEQ ID NO:19) along with a third vector comprising a hygromycin resistance gene (vector 131592; SEQ ID NO:20). Immature embryos were either unconditioned prior to bombardment with these vectors or were pre-conditioned with S301 surfactant (0.01% (v/v), 30 min). To test the effect of preconditioning on genome editing, DNA was extracted from the immature embryos following bombardment and the DNA was analyzed by next-generation sequencing (NGS). The immature embryos were either bombarded once (single shot) or twice (double shot). Table 27 shows the results of this NGS analysis.

TABLE 27

Rice genome editing with and without preconditioning

|  | Unconditioned | Preconditioned |
|---|---|---|
| Single Shot | 0.686% | 15.216% |
| Double Shot | 0.839% | 24.177% |
| Double Shot | 11.992% | 25.489% |

The data in Table 27 show that preconditioning of rice immature embryos leads to improved genome editing results, with an increased proportion of cells comprising DNA modifications at the desired loci as indicated by the increased number of sequence reads showing DNA sequence modifications at the predicted Cpf1 cut site.

We claim:

1. A method of improving transformation of plant cells comprising:
   i) pre-conditioning plant cells by exposure to a surfactant containing medium, wherein said surfactant is a non-ionic trisiloxane surfactant,
   ii) removing said plant cells from said surfactant containing medium, and subsequently,
   iii) contacting said plant cells with at least one polynucleotide sequence to introduce said at least one polynucleotide sequence into said plant cells, wherein said contacting occurs in a medium that lacks surfactant.

2. The method of claim 1, wherein said surfactant containing medium comprises a non-ionic surfactant.

3. The method of claim 1, wherein said surfactant containing medium comprises surfactant at a concentration of 0.001-0.1% (v/v).

4. The method of claim 1 wherein said exposure to a surfactant containing medium lasts for 5-60 minutes.

5. The method of claim 1 wherein said introducing one or more polynucleotide sequence(s) includes the use of *Agrobacterium* cells harboring a plant transformation construct.

6. The method of claim 5 wherein said *Agrobacterium* cells harboring a plant transformation construct comprise a binary vector.

7. The method of claim 5 wherein said *Agrobacterium* cells harboring a plant transformation construct comprise a superbinary vector.

8. The method of claim 1 wherein said improving transformation of plant cells comprises an increased percentage of plant cells exhibiting transient expression of said at least one polynucleotide sequence relative to control plant cells not exposed to said surfactant containing medium.

9. The method of claim 1 wherein said improving transformation of plant cells comprises an increased percentage of callus pieces developing stably transformed sectors.

10. The method of claim 1 wherein said improving transformation of plant cells comprises an increased number of transformed plants regenerated from transformed tissue.

11. The method of claim 1 wherein said plant cells are derived from a monocot.

12. The method of claim 11 wherein said plant cells are derived from *Zea mays, Oryza sativa, Setaria viridis, Sorghum bicolor, Triticum aestivum*, or *Saccharum* sp.

13. The method of claim 1 wherein said plant cells are derived from a dicot.

14. The method of claim 13 wherein said plant cells are derived from *Pisum sativum, Lactuca sativa*, or *Solanum lycopersicum*.

15. The method of claim 1 wherein said at least one polynucleotide sequence comprises a polynucleotide sequence that shares at least 80% sequence identity with a sequence selected from the group of sequences consisting of SEQ ID NOs:1 and 15, or that encodes a protein that shares at least 80% sequence identity with a sequence selected from the group of sequences consisting of SEQ ID NOs:2 and 16.

16. The method of claim 1 wherein said at least one polynucleotide sequence comprises a polynucleotide sequence that shares at least 80% sequence identity with a sequence selected from the group of sequences consisting of SEQ ID NOs:3, 5, and 7, or that encodes a protein that shares at least 80% sequence identity with a sequence selected from the group of sequences consisting of SEQ ID NO:4, 6, and 8.

17. The method of claim 1 wherein said introducing at least one polynucleotide sequence comprises biolistic transformation.

18. The method of claim 1 wherein said at least one polynucleotide sequence encodes at least one CRISPR nuclease.

19. The method of claim 18 wherein said pre-conditioning results in improved genome editing relative to control cells not exposed to said surfactant containing medium.

\* \* \* \* \*